United States Patent
Billiald et al.

(10) Patent No.: US 10,842,870 B2
(45) Date of Patent: Nov. 24, 2020

(54) ANTI-HUMAN GPVI ANTIBODIES AND USES THEREOF

(71) Applicants: ACTICOR BIOTECH, Paris (FR); UNIVERSITE DE PARIS, Paris (FR); UNIVERSITÉ PARIS-XIII, Villetaneuse (FR); INSTITUT NATIONAL DE LA SANTÉ ET DE LA RECHERCHE MÉDICALE (INSERM), Paris (FR); UNIVERSITE PARIS-SACLAY, Saint Aubin (FR)

(72) Inventors: Philippe Billiald, Paris (FR); Martine Jandrot-Perrus, Vanves (FR)

(73) Assignees: ACTICOR BIOTECH, Paris; UNIVERSITE DE PARIS, Paris; UNIVERSITÉ PARIS-XIII, Villetaneuse; INSTITUT NATIONAL DE LA SANTÉ ET DE LA RECHERCHE MÉDICALE (INSERM), Paris; UNIVERSITE PARIS-SACLAY, Saint Subin ( * ) Notice: Subject to any disclaimer, the term of this patent is extended or adjusted under 35 U.S.C. 154(b) by 0 days.

(21) Appl. No.: 15/750,082

(22) PCT Filed: Aug. 5, 2016

(86) PCT No.: PCT/EP2016/068778
§ 371 (c)(1),
(2) Date: Feb. 2, 2018

(87) PCT Pub. No.: WO2017/021539
PCT Pub. Date: Feb. 9, 2017

(65) Prior Publication Data
US 2018/0236071 A1    Aug. 23, 2018

(30) Foreign Application Priority Data
Aug. 5, 2015    (EP) .................................... 15179908

(51) Int. Cl.
| | | |
|---|---|---|
| A61K 39/395 | (2006.01) | |
| C07K 16/28 | (2006.01) | |
| A61P 9/10 | (2006.01) | |
| A61K 39/00 | (2006.01) | |

(52) U.S. Cl.
CPC .......... *A61K 39/39533* (2013.01); *A61P 9/10* (2018.01); *C07K 16/28* (2013.01); *C07K 16/2803* (2013.01); *A61K 2039/505* (2013.01); *C07K 2317/24* (2013.01); *C07K 2317/33* (2013.01); *C07K 2317/34* (2013.01); *C07K 2317/55* (2013.01); *C07K 2317/70* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,591,828 A | 1/1997 | Bosslet et al. | |
| 5,892,019 A | 4/1999 | Schlom et al. | |
| 6,245,527 B1 * | 6/2001 | Busfield ............... | C07K 14/705 435/243 |
| 6,998,469 B2 * | 2/2006 | Tandon .................... | A61P 7/02 530/388.25 |
| 7,101,549 B2 * | 9/2006 | Gill ....................... | C07K 14/705 424/130.1 |
| 7,977,461 B2 * | 7/2011 | Takayama .......... | C07K 16/2803 435/328 |
| 9,045,538 B2 * | 6/2015 | Jandrot-Perrus ....... | C07K 16/28 |
| 9,045,540 B2 * | 6/2015 | Jandrot-Perrus .......... | A61P 9/10 |
| 2002/0141992 A1 | 10/2002 | Nieswandt | |
| 2003/0186885 A1 * | 10/2003 | Tandon .................... | A61P 7/02 530/388.25 |
| 2004/0001826 A1 * | 1/2004 | Gill .................... | C07K 16/2803 424/143.1 |
| 2006/0088531 A1 | 4/2006 | Smethurst et al. | |
| 2007/0071744 A1 * | 3/2007 | Munch ............. | C07K 14/70503 424/133.1 |
| 2010/0003244 A1 | 1/2010 | Munch | |

FOREIGN PATENT DOCUMENTS

| | | |
|---|---|---|
| EP | 0 404 097 A2 | 12/1990 |
| EP | 1 224 942 A1 | 7/2002 |
| EP | 1 228 768 A1 | 8/2002 |
| EP | 1 538 165 A1 | 6/2005 |
| EP | 1 876 240 A1 | 1/2008 |
| EP | 2 363 416 A2 | 9/2011 |
| WO | 1993/011161 A1 | 6/1993 |
| WO | 2001/000810 A1 | 1/2001 |
| WO | 2003/008454 A2 | 1/2003 |
| WO | 2005/111083 A2 | 11/2005 |
| WO | 2006/118350 A1 | 11/2006 |
| WO | WO-2006118350 A1 * | 11/2006 ......... C07K 16/2803 |
| WO | 2006/131512 A2 | 12/2006 |
| WO | 2008/049928 A1 | 5/2008 |
| WO | WO-2008049928 A1 * | 5/2008 ............ C07K 16/28 |
| WO | 2011/073954 A1 | 6/2011 |
| WO | 2011/073954 A2 | 6/2011 |
| WO | 2013/032032 A1 | 3/2013 |
| WO | WO 2017/021539 A2 | 2/2017 |

OTHER PUBLICATIONS

Janeway et al., Immunobiology, 3rd edition, 1997 Garland Publishing Inc., pp. 3:1-3:11.*
Rudikoff et al., Proc Natl Acad Sci USA. Mar. 1982;79(6):1979-83.*
Llyod et al., Protein Eng Des Sel. Mar. 2009;22(3):159-68. doi: 10.1093/protein/gzn058. Epub Oct. 29, 2008.*
Goel et al., J Immunol. Dec. 15, 2004; 173(12):7358-67.*
Edwards et al.,J Mol Biol. Nov. 14, 2003;334(1): 103-18.*

(Continued)

*Primary Examiner* — Michael Szperka
(74) *Attorney, Agent, or Firm* — Lathrop GPM LLP; James H. Velema, Esq.

(57) ABSTRACT

The present invention relates to humanized anti-human GPVI antibodies and uses thereof.

17 Claims, 13 Drawing Sheets

Specification includes a Sequence Listing.

(56) References Cited

OTHER PUBLICATIONS

Kanyavuz et al., Nat Rev Immunol. Jun. 2019;19(6):355-368. doi: 10.1038/S41577-019-0126-7.*
Henry et al., Front. Immunol., Jan. 23, 2018 | https://doi.org/10.3389/fimmu.2018.00041.*
Bannas et al., Front. Immunol., Nov. 22, 2017 | https://doi.org/10.3389/fimmu.2017.01603.*
Altschul et al. (1990) "Basic local alignment search tool," J. Mol. Biol. 215:403-410.
Burton (1985) "Immunoglobulin G: functional sites," Mol. Immunol. 22(3)161-206.
Carillo et al. (1988) "The Multiple Sequence Alignment Problem in Biology," Siam J. Applied Math. 48(5):1073-1082.
Caron et al. (1992) "Engineered humanized dimeric forms of IgG are more effective antibodies," J. Exp. Med. 176:1191-1195.
Chothia et al. (1987) "Canonical structures for the hypervariable regions of immunoglobulins," J. Mol. Biol. 196:901-917.
Chothia et al. (1992) "Structural Repertoire of the Human VH Segments," J. Mol. Biol. 227:799-817.
Clackson et al. (1991) "Making antibody fragments using phage display libraries," Nature. 352:624-628.
Delgado et al. (1996) "Enhanced tumour specificity of an anti-carcinoembrionic antigen Fab' fragment by poly (ethylene glycol) (PEG) modification," Br. J. Cancer. 73(2):175-182.
Devereux et al. (1984) "A comprehensive set of sequence analysis programs for the VAX," Nucl. Acid. Res. 12(1 Pt 1):387-95.
Genbank Database [Online] (Apr. 21, 2005) "platelet glycoprotein VI [*Homo sapiens*]," Accession No. BAA89353.1. National Center for Biotechnology Information. Accessible on the Internet at URL: https://www.ncbi.nlm.nih.gov/protein/BAA89353.1, 2 pgs. [Last Accessed Apr. 13, 2018].
Graham et al. (1997) "Characteristics of a human cell line transformed by DNA from human adenovirus type 5," J. Gen. Virol. 36(1):59-74.
Holliger et al. (1993) "'Diabodies': Small bivalent and bispecific antibody fragments," Proc. Natl. Acad. Sci. 90:6444-6448.
Kohler et al. (1975) "Continuous cultures of fused cells secreting antibody of predefined specificity," Nature. 256:495-497.
Lakhrif et al. (Dec. 18, 2015) "A method to confer Protein L binding ability to any antibody fragment," MAbs. 8(2):379-88.
Lefranc et al. (1999) "IMGT, the international ImMunoGeneTics database," Nucleic Acid Res. 27:209-212.
Leong et al. (2001) "Adapting Pharmacokinetic Properties of a Humanized Anti-Interleukin-8 Antibody for Therapeutic Applications Using Site-Specific Pegylation," Cytokines. 16(3):106-119.
Mammadova-Bach et al. (May 14, 2015) "Platelet glycoprotein VI binds to polymerized fibrin and promotes thrombin generation," Blood. 126(5):683-91.
Mangin et al. (2012) "A humanized glycoprotein VI (GPVI) mouse model to assess the antithrombotic efficacies of anti-GPVI agents," J. Pharmacol. Exp. Ther. 341(1):156-63.
Marks et al. (1991) "By-passing immunization. Human antibodies from V-gene libraries displayed on phage," J. Mol. Biol. 222:581-597.
Martin et al. (1996) "Structural Families in Loops of Homologous Proteins: Automatic Classification, Modelling and Application to Antibodies," J. Mol. Biol. 263:800-815.
Mather (1980) "Establishment and characterization of two distinct mouse testicular epithelial cell lines," Biol. Reprod. 23:Mather.
Mather et al. (1982) "Culture of testicular cells in hormone-supplemented serum-free medium," Annals N.Y. Acad. Sci. 383:44-68.
Morea et al. (2000) "Antibody Modeling: Implications for Engineering and Design," Methods. 20:267-279.
Muzard et al. (2009) "Grafting of protein L-binding activity onto recombinant antibody fragments," Analytical Biochemistry. 388:331-338.
O'Connor et al. (2006) "Selective blockade of glycoprotein VI clustering on collagen helices," J. Biol. Chem. 281(44):33505-10.
Ono et al. (1999) "The humanized anti-HM1.24 antibody effectively kills multiple myeloma cells by human effector cell-mediated cytotoxicity," Mol. Immunol. 36:387-395.
Pluckthun (1994) "Antibodies from *Escherichia coli*," In; The Pharmacology of Monoclonal Antibodies. vol. 113. Eds.: Rosenburg et al. Springer-Verlag. New York, New York. pp. 269-315.
Posthumus et al. (1990) "Analysis and simulation of a neutralizing epitope of transmissible gastroenteritis virus," J. Virology. 64:3304-3309.
Qu et al. (1999) "Humanization of Immu31, an alpha-fetoprotein-specific antibody," Clin. Cancer Res. 5:3095s-3100s.
Roux et al. (1998) "Comparisons of the ability of human IgG3 hinge mutants, IgM, IgE, and IgA2, to form small immune complexes: a role for flexibility and geometry," J. Immunol. 161:4083-90.
Scatchard et al. (1949) "The attractions of proteins for small molecules and ions," Ann. NY Acad. Sci. 51:660-672.
Shopes (1992) "A genetically engineered human IgG mutant with enhanced cytolytic activity," J. Immunol. 148:2918-2922.
Smethurst et al. (2004) "Identification of the primary collagen-binding surface on human glycoprotein VI by site-lirected mutagenesis and by a blocking phage antibody," Blood. 103(3):903-11.
Tomlinson et al. (1995) "The structural repertoire of the human V kappa domain," EMBO J. 14:4628-4638.
Tramontano et al. (1989) "Structural determinants of the conformations of medium-sized loops in proteins," Proteins. 6:382-94.
Tramontano et al. (1990) "Framework residue 71 is a major determinant of the position and conformation of the second hypervariable region in the VH domains of immunoglobulins," J. Mol. Biol. 215:175-182.
Uniprot Database [Online] (First Entered Apr. 4, 2006) "UniProtKB—Q9HCN6 (GPVI_HUMAN)," Accession No. D9HCN6. UniProt Consortium. Accessible on the Internet at URL: http://www.uniprot.org/uniprot/Q9HCN6, 11 pgs. [Last Accessed Apr. 13, 2018].
Urlaub et al. (1980) "Isolation of Chinese hamster cell mutants deficient in dihydrofolate reductase activity," Proc. Natl. Acad. Sci. USA. 77:4216-4220.
Wlliams et al. (1996) "Sequence and Evolution of the Human Germline VλRepertoire," J. Mol. Biol. 264:220-232.
Zahid (2011) "Design and Optimization of Recombinant Antibodies Directed Against Platelet Glycoprotein VI with Therapeutic and Diagnostic Potentials," Doctoral Thesis. Human health and pathology. Université Paris Sud—Pads XI. Accessible on the Internet at URL: https://tel.archives-ouvertes.fr/file/index/docid/922980/filename/VA_ZAHID_Muhammad_24112011.pdf, 276 pgs. [Last Accessed Apr. 13, 2018].
International Search Report with Written Opinion corresponding to International Patent Application No. PCT/EP2016/068778, dated Jan. 27, 2017.
Haiquan et al. "The Fab fragment of a novel anti-GPVI monoclonal antibody, OM4, reduces in vivo thrombosis without bleending risk in rats", Arteriosclerosis, Thrombosis, and Vascular Biology, vol. 27, No. 5, May 2007, pp. 1199-1205.
Jandrot-Perrus et al., "Human Platelet glycoprotein VI: identification of residues invovled in the binding to collagen", Blood (ASH Annual Meeting abstracts), abstract 1550, 2004.
Muzard et al. "Design and umanization of a murine scFv that blocks human platelet glycoprotein VI in vitro", FEBS J. Aug. 2009;276(15):4207-22.
Ohlmann et al. "Ex vivo inhibition of thrombus formation by an anti-glycoprotein VI Fab fragment in non-human primates without modification of glycoprotein VI expression", Journal of Thrombosis and Haemostasis, vol. 6, No. 6, Jun. 2008, pp. 1003-1011.
Yutaka et al. "Ex vivo evaluation of anti-GPVI antibody in cynomolgus monkeys: dissociation between anti-platelet aggregatory effect and bleeding time", Thrombosis and Haemostasis, vol. 96, No. 2, Aug. 2006, pp. 167-175.
Zahid. "Design and optimization of recombinant antibodies directed against platelet glycoprotein VI with therapeutic and diagnostic potentials", PhD thesis, Jan. 2014.
Florian et al, "Anti-GPVI Fab SAR264565 effectively blocks GPVI function in ex vivo human platelets under arterial shear in a perfusion chamber", European Journal of Clinical Pharmacology, vol. 73, No. 8, May 18, 2017, pp. 949-956.

(56) References Cited

OTHER PUBLICATIONS

Matsumoto et al., "Ex vivo evaluation of anti-GPVI antibody in cynomolgus monkeys: dissociation between anti-platelet aggregatory effect and bleeding time", Thrombosis and Haemostasis, vol. 96, No. 2, Aug. 1, 2006, pp. 167-175.

\* cited by examiner

SEQUENCE LISTING

```
<160> NUMBER OF SEQ ID NOS: 24

<210> SEQ ID NO 1
<211> LENGTH: 10
<212> TYPE: PRT
<213> ORGANISM: Artificial Sequence
<220> FEATURE:
<223> OTHER INFORMATION: VH-CDR1

<400> SEQUENCE: 1

Gly Tyr Thr Phe Thr Ser Tyr Asn Met His
1               5                   10

<210> SEQ ID NO 2
<211> LENGTH: 17
<212> TYPE: PRT
<213> ORGANISM: Artificial Sequence
```

```
<220> FEATURE:
<223> OTHER INFORMATION: VH-CDR2

<400> SEQUENCE: 2

Gly Ile Tyr Pro Gly Asn Gly Asp Thr Ser Tyr Asn Gln Lys Phe Gln
1               5                   10                  15

Gly

<210> SEQ ID NO 3
<211> LENGTH: 11
<212> TYPE: PRT
<213> ORGANISM: Artificial Sequence
<220> FEATURE:
<223> OTHER INFORMATION: VH-CDR3

<400> SEQUENCE: 3

Gly Thr Val Val Gly Asp Trp Tyr Phe Asp Val
1               5                   10

<210> SEQ ID NO 4
<211> LENGTH: 16
<212> TYPE: PRT
<213> ORGANISM: Artificial Sequence
<220> FEATURE:
<223> OTHER INFORMATION: VL-CDR1

<400> SEQUENCE: 4

Arg Ser Ser Gln Ser Leu Glu Asn Ser Asn Gly Asn Thr Tyr Leu Asn
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: VL-CDR2

<400> SEQUENCE: 5

Arg Val Ser Asn Arg Phe Ser
1               5

<210> SEQ ID NO 6
<211> LENGTH: 9
<212> TYPE: PRT
<213> ORGANISM: Artificial Sequence
<220> FEATURE:
<223> OTHER INFORMATION: VL-CDR3

<400> SEQUENCE: 6

Leu Gln Leu Thr His Val Pro Trp Thr
1               5

<210> SEQ ID NO 7
<211> LENGTH: 120
<212> TYPE: PRT
<213> ORGANISM: Artificial Sequence
<220> FEATURE:
<223> OTHER INFORMATION: Heavy chain variable region

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

```
Asn Met His Trp Val Arg Gln Ala Pro Gly Gln Gly Leu Glu Trp Met
         35                  40                  45

Gly Gly Ile Tyr Pro Gly Asn Gly Asp Thr Ser Tyr Asn Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Thr Val Val Gly Asp Trp Tyr Phe Asp Val Trp Gly Gln
                100                 105                 110

Gly Thr Leu Val Thr Val Ser Ser
        115                 120

<210> SEQ ID NO 8
<211> LENGTH: 113
<212> TYPE: PRT
<213> ORGANISM: Artificial Sequence
<220> FEATURE:
<223> OTHER INFORMATION: Light chain variable region

<400> SEQUENCE: 8

Asp Ile Gln Met Thr Gln Ser Pro Ser Ser Leu Ser Ala Ser Val Gly
 1               5                  10                  15

Asp Arg Val Thr Ile Thr Cys Arg Ser Gln Ser Leu Glu Asn Ser
                 20                  25                  30

Asn Gly Asn Thr Tyr Leu Asn Trp Tyr Gln Gln Lys Pro Gly Lys Ala
         35                  40                  45

Pro Lys Leu Leu Ile Tyr Arg Val Ser Asn Arg Phe Ser Gly Val Pro
 50                  55                  60

Ser Arg Phe Ser Gly Ser Gly Ser Gly Thr Asp Phe Thr Phe Thr Ile
 65                  70                  75                  80

Ser Ser Leu Gln Pro Glu Asp Ile Ala Thr Tyr Tyr Cys Leu Gln Leu
                 85                  90                  95

Thr His Val Pro Trp Thr Phe Gly Gln Gly Thr Lys Val Glu Ile Thr
                100                 105                 110

Arg

<210> SEQ ID NO 9
<211> LENGTH: 113
<212> TYPE: PRT
<213> ORGANISM: Artificial Sequence
<220> FEATURE:
<223> OTHER INFORMATION: Light chain variable region

<400> SEQUENCE: 9

Asp Ile Gln Met Thr Gln Ser Pro Ser Ser Leu Ser Ala Ser Val Gly
 1               5                  10                  15

Asp Arg Val Thr Ile Thr Cys Ser Ala Ser Gln Ser Leu Glu Asn Ser
                 20                  25                  30

Asn Gly Asn Thr Tyr Leu Asn Trp Tyr Gln Gln Lys Pro Gly Lys Ala
         35                  40                  45

Pro Lys Leu Leu Ile Tyr Arg Val Ser Asn Arg Phe Ser Gly Val Pro
 50                  55                  60

Ser Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Tyr Cys Leu Gln Leu
                 85                  90                  95
```

Thr His Val Pro Trp Thr Phe Gly Gln Gly Thr Lys Val Glu Ile Lys
            100                 105                 110

Arg

<210> SEQ ID NO 10
<211> LENGTH: 360
<212> TYPE: DNA
<213> ORGANISM: Artificial Sequence
<220> FEATURE:
<223> OTHER INFORMATION: Heavy chain variable region

<400> SEQUENCE: 10
caggttcagc tggttcagtc aggggctgag gtgaagaagc tggagcctc agtgaaggtg      60 tcctgcaagg cttctggcta cacatttacc agttacaata tgcactgggt aagacaggct    120
cctggacagg gcctggaatg gatgggaggt atttatccag gaaatggtga tacttcctac    180
aatcagaagt tccagggccg agttactatg actcgggaca cttccacctc tacagtgtac    240
atggagctca gcagcctgag atctgaggac accgcggtct attactgtgc aagaggcacc    300
gtggtcggcg actggtactt cgatgtgtgg ggccaaggca ccctggtcac cgtgagcagt    360

<210> SEQ ID NO 11
<211> LENGTH: 339
<212> TYPE: DNA
<213> ORGANISM: Artificial Sequence
<220> FEATURE:
<223> OTHER INFORMATION: Light chain variable region

<400> SEQUENCE: 11
gacatccaga tgacccagag cccaagcagc ctgagcgcca gcgtgggtga cagagtgacc      60
atcacctgta gaagtagtca gagccttgag aacagcaacg gaaacaccta cctgaattgg    120
taccagcaga agccaggtaa ggctccaaag ctgctgatct acagagtttc caaccgattc    180
tctggtgtgc aagcagatt cagcggtagc ggtagcggta ccgacttcac cttcaccatc    240
agcagcctcc agccagagga catcgccacc tactactgcc tccagctgac tcatgtccca    300
tggaccttcg gtcagggcac caaggtggag atcacccgg                            339

<210> SEQ ID NO 12
<211> LENGTH: 339
<212> TYPE: DNA
<213> ORGANISM: Artificial Sequence
<220> FEATURE:
<223> OTHER INFORMATION: Light chain variable region

<400> SEQUENCE: 12
gacatccaga tgacccagag cccaagcagc ctgagcgcca gcgtgggtga cagagtgacc      60
atcacctgta gtgccagtca gagccttgag aacagcaacg gaaacaccta cctgaattgg    120
taccagcaga agccaggtaa ggctccaaag ctgctgatct acagagtttc caaccgattc    180
tctggtgtgc aagcagatt cagcggtagc ggtagcggta ccgacttcac cctcaccatc    240
agcagcctcc agccagagga cttcgccacc tactactgcc tccagctgac tcatgtccca    300
tggaccttcg gtcagggcac caaggtggag atcaaacgc                            339

<210> SEQ ID NO 13
<211> LENGTH: 339
<212> TYPE: PRT
<213> ORGANISM: Homo sapiens

<400> SEQUENCE: 13

Met Ser Pro Ser Pro Thr Ala Leu Phe Cys Leu Gly Leu Cys Leu Gly
1               5                   10                  15

Arg Val Pro Ala Gln Ser Gly Pro Leu Pro Lys Pro Ser Leu Gln Ala
            20                  25                  30

Leu Pro Ser Ser Leu Val Pro Leu Glu Lys Pro Val Thr Leu Arg Cys
        35                  40                  45

Gln Gly Pro Pro Gly Val Asp Leu Tyr Arg Leu Glu Lys Leu Ser Ser
    50                  55                  60

Ser Arg Tyr Gln Asp Gln Ala Val Leu Phe Ile Pro Ala Met Lys Arg
65                  70                  75                  80

Ser Leu Ala Gly Arg Tyr Arg Cys Ser Tyr Gln Asn Gly Ser Leu Trp
                85                  90                  95

Ser Leu Pro Ser Asp Gln Leu Glu Leu Val Ala Thr Gly Val Phe Ala
            100                 105                 110

Lys Pro Ser Leu Ser Ala Gln Pro Gly Pro Ala Val Ser Ser Gly Gly
        115                 120                 125

Asp Val Thr Leu Gln Cys Gln Thr Arg Tyr Gly Phe Asp Gln Phe Ala
    130                 135                 140

Leu Tyr Lys Glu Gly Asp Pro Ala Pro Tyr Lys Asn Pro Glu Arg Trp
145                 150                 155                 160

Tyr Arg Ala Ser Phe Pro Ile Ile Thr Val Thr Ala Ala His Ser Gly
                165                 170                 175

Thr Tyr Arg Cys Tyr Ser Phe Ser Ser Arg Asp Pro Tyr Leu Trp Ser
            180                 185                 190

Ala Pro Ser Asp Pro Leu Glu Leu Val Val Thr Gly Thr Ser Val Thr
        195                 200                 205

Pro Ser Arg Leu Pro Thr Glu Pro Pro Ser Ser Val Ala Glu Phe Ser
    210                 215                 220

Glu Ala Thr Ala Glu Leu Thr Val Ser Phe Thr Asn Lys Val Phe Thr
225                 230                 235                 240

Thr Glu Thr Ser Arg Ser Ile Thr Thr Ser Pro Lys Glu Ser Asp Ser
                245                 250                 255

Pro Ala Gly Pro Ala Arg Gln Tyr Tyr Thr Lys Gly Asn Leu Val Arg
            260                 265                 270

Ile Cys Leu Gly Ala Val Ile Leu Ile Ile Leu Ala Gly Phe Leu Ala
        275                 280                 285

Glu Asp Trp His Ser Arg Arg Lys Arg Leu Arg His Arg Gly Arg Ala
    290                 295                 300

Val Gln Arg Pro Leu Pro Pro Leu Pro Pro Leu Pro Gln Thr Arg Lys
305                 310                 315                 320

Ser His Gly Gly Gln Asp Gly Gly Arg Gln Asp Val His Ser Arg Gly
                325                 330                 335

Leu Cys Ser

<210> SEQ ID NO 14
<211> LENGTH: 321
<212> TYPE: DNA
<213> ORGANISM: Artificial Sequence
<220> FEATURE:
<223> OTHER INFORMATION: Heavy chain constant region

```
<400> SEQUENCE: 14
gcctccacca agggtccctc agtcttccca ctggcaccct cctccaagag cacctctggt      60
ggcacagctg ccctgggctg cctggtcaag gactacttcc cagaaccagt gactgtgtca    120
tggaactcag gcgccctgac cagcggcgtg cacaccttcc ctgctgtctt gcagtcctca    180
ggactctact ccctcagcag cgtggtgacc gtgccctcca gcagcttggg cacccagacc    240
tacatctgca acgtgaatca caagcccagc aacaccaagg tggacaagaa agtcgagcct    300
aagtcatgcg acaagactca c                                              321

<210> SEQ ID NO 15
<211> LENGTH: 318
<212> TYPE: DNA
<213> ORGANISM: Artificial Sequence
<220> FEATURE:
<223> OTHER INFORMATION: Light chain constant region

<400> SEQUENCE: 15
actgtggctg caccaagtgt gttcatcttc ccacctagcg atgagcagtt gaaatctgga     60
actgcctctg tcgtgtgcct cctgaacaac ttctacccac gggaggccaa ggtacagtgg    120
aaggtggata acgccctcca atccggtaac tcccaggaga gtgtcacaga gcaagatagc    180
aaggacagca cctacagcct cagcagcacc ctgactctga gcaaagcaga ctacgagaag    240
cacaaggtct acgcctgcga agtcacccat cagggcctga gttccctgt cacaaagagc     300 ttcaaccggg gagagtgt                                                  318

<210> SEQ ID NO 16
<211> LENGTH: 66
<212> TYPE: DNA
<213> ORGANISM: Artificial Sequence
<220> FEATURE:
<223> OTHER INFORMATION: Signal peptide

<400> SEQUENCE: 16
atggatatgc gtgtaccagc tcaactactt ggacttctat tgctttggct tcgtggtgct     60
agatgt                                                                66

<210> SEQ ID NO 17
<211> LENGTH: 57
<212> TYPE: DNA
<213> ORGANISM: Artificial Sequence
<220> FEATURE:
<223> OTHER INFORMATION: Signal peptide

<400> SEQUENCE: 17
atggactgga cttggagaat cctattcttg gttgctgcag ctacaggtgc tcattca        57

<210> SEQ ID NO 18
<211> LENGTH: 762
<212> TYPE: DNA
<213> ORGANISM: Artificial Sequence
<220> FEATURE:
<223> OTHER INFORMATION: Heavy chain

<400> SEQUENCE: 18
gcggccgcca ccatggactg gacttggaga atcctattct tggttgctgc agctacaggt     60
gctcattcac aggttcagct ggttcagtca ggggctgagg tgaagaagcc tggagcctca    120
gtgaaggtgt cctgcaaggc ttctggctac acatttacca gttacaatat gcactgggta    180
agacaggctc ctggacaggg cctggaatgg atgggaggta tttatccagg aaatggtgat    240
```

| | |
|---|---:|
| acttcctaca atcagaagtt ccagggccga gttactatga ctcgggacac ttccacctct | 300 |
| acagtgtaca tggagctcag cagcctgaga tctgaggaca ccgcggtcta ttactgtgca | 360 |
| agaggcaccg tggtcggcga ctggtacttc gatgtgtggg gccaaggcac cctggtcacc | 420 |
| gtgagcagtg cctccaccaa gggtccctca gtcttccac tggcaccctc ctccaagagc | 480 |
| acctctggtg gcacagctgc cctgggctgc ctggtcaagg actacttccc agaaccagtg | 540 |
| actgtgtcat ggaactcagg cgccctgacc agcggcgtgc acaccttccc tgctgtcttg | 600 |
| cagtcctcag gactctactc cctcagcagc gtggtgaccg tgcctccag cagcttgggc | 660 |
| acccagacct acatctgcaa cgtgaatcac aagcccagca caccaaggt ggacaagaaa | 720 |
| gtcgagccta agtcatgcga caagactcac tgatgaggat cc | 762 |

<210> SEQ ID NO 19
<211> LENGTH: 742
<212> TYPE: DNA
<213> ORGANISM: Artificial Sequence
<220> FEATURE:
<223> OTHER INFORMATION: Light chain

<400> SEQUENCE: 19

| | |
|---|---:|
| gacgtcacca tggatatgcg tgtaccagct caactacttg gacttctatt gctttggctt | 60 |
| cgtggtgcta gatgtgacat ccagatgacc cagagcccaa gcagcctgag cgccagcgtg | 120 |
| ggtgacagag tgaccatcac ctgtagaagt agtcagagcc ttgagaacag caacggaaac | 180 |
| acctacctga attggtacca gcagaagcca ggtaaggctc aaagctgct gatctacaga | 240 |
| gtttccaacc gattctctgg tgtgccaagc agattcagcg gtagcggtag cggtaccgac | 300 |
| ttcaccttca ccatcagcag cctccagcca gaggacatcg ccacctacta ctgcctccag | 360 |
| ctgactcatg tcccatggac cttcggtcag ggcaccaagg tggagatcac ccggactgtg | 420 |
| gctgcaccaa gtgtgttcat cttcccacct agcgatgagc agttgaaatc tggaactgcc | 480 |
| tctgtcgtgt gcctcctgaa caacttctac ccacgggagg ccaaggtaca gtggaaggtg | 540 |
| gataacgccc tccaatccgg taactcccag gagagtgtca cagagcaaga tagcaaggac | 600 |
| agcacctaca gcctcagcag caccctgact ctgagcaaag cagactacga gaagcacaag | 660 |
| gtctacgcct gcgaagtcac ccatcagggc ctgagttccc ctgtcacaaa gagcttcaac | 720 |
| cggggagagt gttgatgata tc | 742 |

<210> SEQ ID NO 20
<211> LENGTH: 742
<212> TYPE: DNA
<213> ORGANISM: Artificial Sequence
<220> FEATURE:
<223> OTHER INFORMATION: Light chain

<400> SEQUENCE: 20

| | |
|---|---:|
| gacgtcacca tggatatgcg tgtaccagct caactacttg gacttctatt gctttggctt | 60 |
| cgtggtgcta gatgtgacat ccagatgacc cagagcccaa gcagcctgag cgccagcgtg | 120 |
| ggtgacagag tgaccatcac ctgtagtgcc agtcagagcc ttgagaacag caacggaaac | 180 |
| acctacctga attggtacca gcagaagcca ggtaaggctc aaagctgct gatctacaga | 240 |
| gtttccaacc gattctctgg tgtgccaagc agattcagcg gtagcggtag cggtaccgac | 300 |
| ttcaccctca ccatcagcag cctccagcca gaggacttcg ccacctacta ctgcctccag | 360 |
| ctgactcatg tcccatggac cttcggtcag ggcaccaagg tggagatcaa acgcactgtg | 420 |

```
gctgcaccaa gtgtgttcat cttcccacct agcgatgagc agttgaaatc tggaactgcc      480
tctgtcgtgt gcctcctgaa caacttctac ccacgggagg ccaaggtaca gtggaaggtg      540
gataacgccc tccaatccgg taactcccag gagagtgtca cagagcaaga tagcaaggac      600
agcacctaca gcctcagcag cacccTgact ctgagcaaag cagactacga aaagcacaag      660
gtctacgcct gcgaagtcac ccatcagggc ctgagttccc ctgtcacaaa gagcttcaac      720
cggggagagt gttgatgata tc                                               742

<210> SEQ ID NO 21
<211> LENGTH: 4
<212> TYPE: PRT
<213> ORGANISM: Artificial Sequence
<220> FEATURE:
<223> OTHER INFORMATION: CDR-L3 - Residues after
<220> FEATURE:
<221> NAME/KEY: SITE
<222> LOCATION: 3
<223> OTHER INFORMATION: X is any amino acid

<400> SEQUENCE: 21

Phe Gly Xaa Gly
1

<210> SEQ ID NO 22
<211> LENGTH: 4
<212> TYPE: PRT
<213> ORGANISM: Artificial Sequence
<220> FEATURE:
<223> OTHER INFORMATION: CDR-H1 - Residues before
<220> FEATURE:
<221> NAME/KEY: SITE
<222> LOCATION: 2
<223> OTHER INFORMATION: X is any amino acid
<220> FEATURE:
<221> NAME/KEY: SITE
<222> LOCATION: 3
<223> OTHER INFORMATION: X is any amino acid
<220> FEATURE:
<221> NAME/KEY: SITE
<222> LOCATION: 4
<223> OTHER INFORMATION: X is any amino acid

<400> SEQUENCE: 22

Cys Xaa Xaa Xaa
1

<210> SEQ ID NO 23
<211> LENGTH: 5
<212> TYPE: PRT
<213> ORGANISM: Artificial Sequence
<220> FEATURE:
<223> OTHER INFORMATION: CDR-H2 - Residues before

<400> SEQUENCE: 23

Leu Glu Trp Ile Gly
1               5

<210> SEQ ID NO 24
<211> LENGTH: 4
<212> TYPE: PRT
<213> ORGANISM: Artificial Sequence
<220> FEATURE:
<223> OTHER INFORMATION: CDR-H3 - Residues after
<220> FEATURE:
<221> NAME/KEY: SITE
<222> LOCATION: 3
<223> OTHER INFORMATION: X is any amino acid
```

```
<400> SEQUENCE: 24

Trp Gly Xaa Gly
1
```

ANTI-HUMAN GPVI ANTIBODIES AND USES THEREOF

RELATED APPLICATIONS

This application is a 35 U.S.C. § 371 filing of International Patent Application No. PCT/EP2016/068778, filed Aug. 5, 2016, which claims priority to European Patent Application No. 15179908.7, filed Aug. 5, 2015, the entire disclosures of which are hereby incorporated herein by reference in their entirety.

FIELD OF INVENTION

The present invention relates to novel anti-human glycoprotein VI antibodies, and to the uses thereof for treating cardiovascular diseases.

BACKGROUND OF INVENTION

Acute coronary and cerebrovascular accidents are currently a major cause of death in the world. In addition, the global incidence of recurrence and death in the 6-month post-treatment period after an acute coronary syndrome is still 8-15%.

In the case of acute coronary syndrome with ST segment elevation, mechanical treatment with coronary angioplasty and introduction of a stent is highly efficient to urgently restore coronary artery flow, but does not prevent morbidity/mortality for about 15% of patients in the next 6 months. Thrombolytic treatments, which are based on long term fibrinolytic, anticoagulant and anti-aggregating drugs associations, give even less encouraging results. Indeed, despite improvements in medical treatment of thrombosis, morbidity/mortality at 6 months is similar to that observed for acute coronary syndrome without ST segment elevation.

Regarding cerebrovascular ischemic accidents, treatments are still very limited due to the generally late caring of most patients and to the hemorrhagic risk of currently available anti-thrombotic treatments.

There is thus still a clinical need for improving treatments for cardiovascular diseases, and especially for new molecules with improved features compared to available molecules. The challenge to face is to obtain molecules with excellent efficiency on the pathological thrombosis but devoid of risk of bleeding.

To answer to this requirement, the target must have a greater role in thrombus formation occurring in a diseased vessel than in physiological hemostasis required to limit the bleeding in a healthy vessel. This is the case of platelet Glycoprotein VI that has been demonstrated in animals to play a role in experimental thrombosis including stroke, vascular remodeling and to be critical in atherothrombosis.

Contrary to αIIbβ3 integrin antagonists, which are currently used in thrombosis treatment and inhibit platelet final activation phase, i.e. platelet aggregation, and to antagonists of platelet recruitment (inhibitors of the P2Y12 ADP receptor and aspirin), GPVI is implicated into several steps of the platelet plug formation: initiation via the interaction with the injured vascular wall, amplification via initial platelet activation leading to the secretion of secondary agonists, the activation of integrins and of platelet procoagulant activity, growth and stabilization via the interaction with fibrin (Mammadova et al., Blood 2015). Thus, GPVI antagonists may prevent not only platelet aggregation, but also secondary agonists liberation as well a growth factors and cytokines secretion resulting into vascular lesions development. Finally, GPVI expression is limited to platelets and megakaryocytes, and thus represents a perfectly specific target for anti-thrombosis treatment.

GPVI antagonists were thus developed for treating cardiovascular diseases.

WO 2001/000810 and WO 2003/008454 both describe a soluble GPVI recombinant protein which is a fusion protein between the GPVI extracellular domain and a human Ig Fc domain. This soluble recombinant GPVI protein competes with platelet GPVI for binding collagen. Encouraging results were first obtained with this soluble GPVI protein in a thrombosis murine model, but these results were not confirmed. In addition, this approach involves structural, functional and pharmacological disadvantages. First, this compound is a high molecular weight chimeric protein (~160 kDa). GPVI-Fc targets the collagen exposed at the site of the vascular injury, the amount and accessibility of which are poorly predictable and, thus, the amount of product to be injected constitutes a potential limitation to the use of GPVI-Fc. Another limitation could be the risk of immunization against neoepitopes potentially exposed on the fusion protein.

Neutralizing monoclonal antibodies directed against human GPVI were also described in the art.

For example, EP 1224942 and EP 1228768 disclose the rat monoclonal anti-GPVI antibody JAQ1, which specifically binds to mouse GPVI, for the treatment of thrombotic disease. JAQ1 antibody induces irreversible internalization of the GPVI receptor on mouse platelets.

EP 1538165 describes another rat monoclonal anti-GPVI antibody (hGP 5C4), which Fab fragment was found to have marked inhibitory effects on the main physiological functions of platelets induced by collagen stimulation: stimulation of collagen-mediated physiological activation markers PAC-I and CD62P-Selectin was completely prevented by hGP 5C4 Fab, and hGP 5C4 Fab potently inhibited human platelet aggregation ex vivo without any intrinsic activity. However, 5C4 is a rat antibody, and therefore only presents a very limited therapeutic potential.

WO 2005/111083 describes 4 mouse monoclonal anti-GPVI antibodies OM1, OM2, OM3 and OM4, that were found to inhibit GPVI binding to collagen, collagen-induced secretion and thromboxane A2 (TXA2) formation in vitro, as well as ex vivo collagen-induced platelet aggregation after intravenous injection to Cynomolgus monkeys. OM4 also appears to inhibit thrombus formation in a rat thrombosis model.

WO 2001/000810 also describes various murine monoclonal anti-GPVI antibodies named 8M14.3, 3F8.1, 9E18.3, 3J24.2, 6E12.3, 1P10.2, 4L7.3, 7H4.6, 9012.2, 7H14.1, and 9E18.2, as well as several human phage antibodies scFv fragments named A9, A10, C9, A4, C10, B4, C3 and D11. Some of these antibodies and scFv fragments were found to inhibit GPVI binding to collagen, including antibodies 8M14.3, 3F8.1, 9E18.3, 3J24.2, 6E12.3, 1P10.2, 4L7.3, 7H4.6, and 9012.2, and scFv fragments A10, A4, C10, B4, C3 and D11. In addition, 9012.2 Fab fragments were found to completely block collagen-induced platelet aggregation and secretion, to block fibrin-induced platelet aggregation, to inhibit the procoagulant activity of collagen-stimulated or fibrin-stimulated platelets and platelet adhesion to collagen or fibrin in static conditions, to impair platelet adhesion and to prevent thrombi formation under arterial flow conditions.

WO 2008/049928 describes a scFv fragment derived from 9012.2, constituted of the VH and VL domains of 9012.2 monoclonal antibody linked via a (Gly$_4$Ser)$_3$ peptide.

However, none of the currently known anti-GPVI antibodies was shown to be efficient in vivo for preventing and/or treating cardiovascular diseases. In particular, the majority of anti-GPVI antibodies that have been reported appeared not fitted for the development of an antithrombotic for medical use in human, especially due to their animal origin.

In particular, some human phage antibodies scFvs directed to human GPVI have been reported to be inhibitory but their affinity appears to be low. Moreover, cross-linking of GPVI at the platelet surface by a divalent or multivalent ligand such as 9O12.2 whole IgG results in platelet activation via GPVI dimerization and via cross-linking of GPVI to the low affinity Fc receptor (FcγRIIA). In contrast, monovalent 9O12.2 Fab and scFv fragments are inhibitory.

However, these fragments could not be used in therapeutic due to their size and to their animal origin which makes them immunogenic in human patients. Moreover, scFv fragments present a short half-life, which limits their therapeutic potentials.

There is thus still a need for neutralizing GPVI antagonists without immunogenicity in human.

US 2006/0088531 describes a human scFv fragment 10B12, presenting a $K_D$ for binding to human GPVI of about $7.9 \cdot 10^{-7}$ M. Smethurst et al., 2004, further describes the epitope bound by 10B12 on the Ig-like C2-type domain 1 (D1) of human GPVI. This epitope comprises residues R58, K61, R66, K79 and R80 of human GPVI (numbering based on UniProtKB accession number Q9HCN6).

O'Connor et al., 2006, also describes a human scFv fragment 1C3, of low affinity for GPVI (5.4 $10^{-7}$ M), which neither blocked collagen-induced platelet aggregation nor GPVI binding to collagen but which potentiated the inhibitory effect of the 10B12 antibody. The 1C3 epitope in GPVI comprises amino acid I168, and it is further postulated that this epitope might encompass a region between residues S164 and S182, a region which is highly conserved from mouse to human.

There is thus a need for a humanized antibody (i.e. an antibody without immunogenicity in human) with improved affinity, efficacy and half-life as compared to the antagonists of the prior art, as a means for efficiently and contentedly preventing and/or treating cardiovascular diseases in human. Moreover, these antagonists should preferably be easily purified.

In the art, anti-GPVI antibodies inducing a GPVI depletion phenotype were described (WO 2006/118350, WO 2011/073954, EP 2363416). In particular, WO 2006/118350 discloses an anti-GPVI antibody directed against all mammalians. The epitope of GPVI bound by this antibody is described and corresponds to the loops 9 and 11 of the Ig-like C2-type domain 2 of GPVI, corresponding to amino acid residues 136-142 and 158-162, respectively.

However, GPVI depletion is undesirable since it cannot be controlled, and is irreversible (i.e. it lasts the lifetime of platelets, or even longer due to GPVI depletion on megakaryocytes).

In therapy, a rapid and safe antiplatelet effect is required. Therefore, antibodies not inducing a GPVI depletion phenotype, and preferably not inducing a decrease in platelet count in vivo (i.e. with a reversible effect) should be developed.

The Applicant developed an antibody anti-GPVI binding to a novel, undescribed, conformational epitope. Said antibody anti-GPVI has a strong affinity for human GPVI, and blocks GPVI interaction with its ligands (including collagen and fibrin), without decreasing the platelet count nor depleting GPVI in vivo. The present invention thus relates to an improved humanized neutralizing antibody specific to human GPVI.

SUMMARY

The present invention relates to an isolated humanized protein binding to human Glycoprotein VI (hGPVI), wherein said protein binds to a conformational epitope comprising:
  at least one amino acid residue from amino acid residues 114 to 142 of hGPVI (SEQ ID NO: 13) or from a sequence sharing at least 60% of identity over amino acid residues 114 to 142 of hGPVI (SEQ ID NO: 13); and
  at least one amino acid residue from amino acid residues 165 to 187 of hGPVI (SEQ ID NO: 13) or from a sequence sharing at least 60% of identity over amino acid residues 165 to 187 of hGPVI (SEQ ID NO: 13).

In one embodiment, the conformational epitope bound by the isolated humanized protein of the invention comprises at least one amino acid residue from amino acid residues 121 to 135 of hGPVI (SEQ ID NO: 13) or from a sequence sharing at least 60% of identity over amino acid residues 121 to 135 of hGPVI (SEQ ID NO: 13); and at least one amino acid residue from amino acid residues 169 to 183 of hGPVI (SEQ ID NO: 13) or from a sequence sharing at least 60% of identity over amino acid residues 169 to 183 of hGPVI (SEQ ID NO: 13).

The present invention also relates to an isolated humanized protein binding to human Glycoprotein VI (hGPVI), wherein said protein has a $K_D$ for binding to hGPVI less than 15 nM, wherein said $K_D$ is measured by surface plasmon resonance using 960 to 1071 RU of soluble human GPVI and using PBS pH 7.4 as running buffer. In one embodiment, the isolated humanized protein of the invention does not induce a GPVI depletion phenotype in vivo.

In one embodiment, the protein of the invention is an antibody molecule selected from the group consisting of a whole antibody, a humanized antibody, a single chain antibody, a Fv, a Fab; or an antibody fragment selected from the group consisting of a unibody, a domain antibody, and a nanobody; or a monomeric antibody mimetic selected from the group consisting of an affibody, an affilin, an affitin, an adnectin, an atrimer, an evasin, a DARPin, an anticalin, an avimer, a fynomer, and a versabody.

In one embodiment, the antibody of the invention is monovalent.

In one embodiment, the variable region of the heavy chain comprises at least one of the following CDRs:

```
VH-CDR1:
                                    (SEQ ID NO: 1)
GYTFTSYNMH;

VH-CDR2:
                                    (SEQ ID NO: 2)
GIYPGNGDTSYNQKFQG;
and

VH-CDR3:
                                    (SEQ ID NO: 3)
GTVVGDWYFDV,
``` or any CDR having an amino acid sequence that shares at least 60% of identity with SEQ ID NO: 1-3, In one embodiment, the variable region of the light chain comprises at least one of the following CDRs:

VL-CDR1:
(SEQ ID NO: 4)
RSSQSLENSNGNTYLN;

VL-CDR2:
(SEQ ID NO: 5)
RVSNRFS;
and

VL-CDR3:
(SEQ ID NO: 6)
LQLTHVPWT, or any CDR having an amino acid sequence that shares at least 60% of identity with SEQ ID NO: 4-6.

In one embodiment, the variable region of the heavy chain comprises at least one of the CDRs as defined hereinabove and the variable region of the light chain comprises at least one of the CDRs as defined hereinabove.

In one embodiment, the variable region of the heavy chain comprises the following CDRs: GYTFTSYNMH (SEQ ID NO: 1), GIYPGNGDTSYNQKFQG (SEQ ID NO: 2) and GTVVGDWYFDV (SEQ ID NO: 3) and the variable region of the light chain comprises the following CDRs: RSSQSLENSNGNTYLN (SEQ ID NO: 4), RVSNRFS (SEQ ID NO: 5) and LQLTHVPWT (SEQ ID NO: 6) or any CDR having an amino acid sequence that shares at least 60% of identity with said SEQ ID NO: 1-6.

In one embodiment, the amino acid sequence encoding the heavy chain variable region is SEQ ID NO: 7 and the amino acid sequence encoding the light variable region is SEQ ID NO: 8, or any sequence having an amino acid sequence that shares at least 60% of identity with said SEQ ID NO: 7 or 8.

In one embodiment, the amino acid sequence encoding the heavy chain variable region is SEQ ID NO: 7 and the amino acid sequence encoding the light variable region is SEQ ID NO: 9, or any sequence having an amino acid sequence that shares at least 60% of identity with said SEQ ID NO: 7 or 9.

The present invention further relates to a composition comprising the protein binding to human GPVI as defined hereinabove.

The present invention further relates to a pharmaceutical composition comprising the protein binding to human GPVI as defined hereinabove and at least one pharmaceutically acceptable excipient.

In one embodiment, the pharmaceutical composition of the invention is for treating, or for use in treating, a GPVI-related condition.

In one embodiment, said GPVI-related condition is a cardiovascular disease selected from arterial and venous thrombosis, restenosis, acute coronary syndrome and ischemic cerebrovascular accidents.

The present invention further relates to the use of the antibody against human GPVI of the invention for detecting GPVI in a biological sample.

Another object of the invention is an expression vector comprising at least one of SEQ ID NO: 10, SEQ ID NO: 11, and SEQ ID NO: 12 or any sequence having a nucleic acid sequence that shares at least 60% of identity with said SEQ ID NO: 10-12.

DETAILED DESCRIPTION

"Glycoprotein VI (GPVI)" is a platelet membrane glycoprotein that is involved in platelet-collagen interactions. GPVI is a transmembrane collagen receptor expressed on the surface of platelets. In one embodiment, the amino acid sequence of human GPVI is SEQ ID NO: 13 (accession number: BAA89353.1) or any amino acid sequence presenting at least about 90% identity with SEQ ID NO: 13, preferably at least about 91, 92, 93, 94, 95, 96, 97, 98, 99% identity or more with SEQ ID NO: 13.

(SEQ ID NO: 13)
MSPSPTALFCLGLCLGRVPA (Signal peptide)

QSGPLPKPSLQALPSSLVPLEKPVTLRCQGPPGVDLYRLEKLSSSRYQD

QAVLFIPAMKRSLAGRYRCSYQNGSLWSLPSDQLELVATGVFAKPSLSA

QPGPAVSSGGDVTLQCQTRYGFDQFALYKEGDPAPYKNPERWYRASFPI

ITVTAAHSGTYRCYSFSSRDPYLWSAPSDPLELVVTGTSVTPSRLPTEP

PSSVAEFSEATAELTVSFTNKVFTTETSRSITTSPKESDSPAGPARQYY

TKGN (Extracellular domain)

LVRICLGAVILIILAGFLAEDWHSRRKRLRHRGRAVQRPLPPLPPLPQT
RKSHGGQDGGRQDVHSRGLCS (Transmembrane and cytoplasmic domains)

The extracellular domain of GPVI is composed of two Ig-like C2-type domains, namely D1 and D2, linked by a hinge interdomain. In one embodiment, D1 comprises amino acid residues 21 to 109 of SEQ ID NO: 13. In one embodiment, the hinge interdomain between D1 and D2 comprises amino acid residues 110 to 113 of SEQ ID NO: 13. In one embodiment, D2 comprises amino acid residues 114 to 207 of SEQ ID NO: 13.

"About" preceding a figure means plus or less 10% of the value of said figure.

"Antibody" or "Immunoglobulin"—As used herein, the term "immunoglobulin" includes a protein having a combination of two heavy and two light chains whether or not it possesses any relevant specific immunoreactivity. "Antibodies" refers to such assemblies which have significant known specific immunoreactive activity to an antigen of interest (e.g. human GPVI). The term "anti-GPVI antibodies" is used herein to refer to antibodies which exhibit immunological specificity for human GPVI protein. As explained elsewhere herein, "specificity" for human GPVI does not exclude cross-reaction with species homologues of GPVI. Antibodies and immunoglobulins comprise light and heavy chains, with or without an interchain covalent linkage between them. Basic immunoglobulin structures in vertebrate systems are relatively well understood. The generic term "immunoglobulin" comprises five distinct classes of antibody that can be distinguished biochemically. All five classes of antibodies are within the scope of the present invention; the following discussion will generally be directed to the IgG class of immunoglobulin molecules. With regard to IgG, immunoglobulins comprise two identical light polypeptide chains of molecular weight of about 23,000 Daltons, and two identical heavy chains of molecular weight of about 53,000-70,000 Daltons. The four chains are joined by disulfide bonds in a "Y" configuration wherein the light chains bracket the heavy chains starting at the mouth of the "Y" and continuing through the variable region. The light chains of an antibody are classified as either kappa or lambda ([K], RD. Each heavy chain class may be bonded with either a kappa or lambda light chain. In general, the light and heavy chains are covalently bonded to each other, and the "tail" regions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon (γ, μ, α, δ, ε) with some subclasses among them (e.g., γ1-γ4). It is the nature of this chain that determines the "class" of the antibody as IgG, IgM, IgA IgD, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention. As indicated above, the variable region of an antibody allows the antibody to selectively recognize and specifically bind epitopes on antigens. That is, the light chain variable domain (VL domain) and heavy chain variable domain (VH domain) of an antibody combine to form the variable region that defines a three-dimensional antigen binding site. This quaternary antibody structure forms the antigen binding site presents at the end of each arm of the "Y". More specifically, the antigen binding site is defined by three complementarity determining regions (CDRs) on each of the VH and VL chains.

"An isolated antibody"—As used herein, an "isolated antibody" is one that has been separated and/or recovered from a component of its natural environment. Contaminant components of its natural environment are materials that would interfere with diagnostic or therapeutic uses of the antibody, and may include enzymes, hormones, and other proteinaceous or non-proteinaceous components. In preferred embodiments, the antibody is purified: (1) to greater than 80, 85, 90, 91, 92, 93, 94, 95% or more by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity as shown by SDS-PAGE under reducing or non-reducing conditions and using Coomassie blue or, preferably, silver staining. Isolated antibody includes the antibody in situ within recombinant cells since at least one component of the antibody's natural environment will not be present. Ordinarily, however, isolated antibody will be prepared by at least one purification step.

"Affinity variants"—As used herein, the term "affinity variant" refers to a variant antibody which exhibits one or more changes in amino acid sequence compared to a reference anti-GPVI antibody, wherein the affinity variant exhibits an altered affinity for the human GPVI protein in comparison to the reference antibody. Typically, affinity variants will exhibit an improved affinity for human GPVI, as compared to the reference anti-GPVI antibody. The improvement may be either a lower $K_D$ for human GPVI, a higher $K_A$ for human GPVI, a faster on-rate for human GPVI or a slower off-rate for human GPVI or an alteration in the pattern of cross-reactivity with non-human GPVI homologues. Affinity variants typically exhibit one or more changes in amino acid sequence in the CDRs, as compared to the reference anti-GPVI antibody. Such substitutions may result in replacement of the original amino acid present at a given position in the CDRs with a different amino acid residue, which may be a naturally occurring amino acid residue or a non-naturally occurring amino acid residue. The amino acid substitutions may be conservative or non-conservative.

"Binding Site"—As used herein, the term "binding site" comprises a region of a protein which is responsible for selectively binding to a target antigen of interest (e.g. human GPVI). Binding domains or binding regions comprise at least one binding site. Exemplary binding domains include an antibody variable domain. The protein of the invention may comprise a single antigen binding site or multiple (e.g., two, three or four) antigen binding sites. Preferably, however, the protein of the invention comprises a single antigen binding site.

"Conservative amino acid substitution"—As used herein, a "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide may be replaced with another amino acid residue from the same side chain family. In another embodiment, a string of amino acids can be replaced with a structurally similar string that differs in order and/or composition of side chain family members.

"Chimeric"—As used herein, a "chimeric" protein comprises a first amino acid sequence linked to a second amino acid sequence with which it is not naturally linked in nature. The amino acid sequences may normally exist in separate proteins that are brought together in the fusion protein or they may normally exist in the same protein but are placed in a new arrangement in the fusion protein. A chimeric protein may be created, for example, by chemical synthesis, or by creating and translating a polynucleotide in which the peptide regions are encoded in the desired relationship.

"CDR"—As used herein, the term "CDR" or "complementarity determining region" means the non-contiguous antigen combining sites found within the variable region of both heavy and light chain polypeptides. CDRs were identified according to the following rules as deduced from Kabat et al. (1991) and Chotia and Lesk (1987):

CDR-L1:
Start—Approx residue 24
Residue before is always a Cys
Residue after is always a Trp. Typically TRP-TYR-GLN, but also, TRP-LEU-GLN, TRP-PHE-GLN, TRP-TYR-LEU
Length 10 to 17 residues CDR-L2:
Start—always 16 residues after the end of L1
Residues before generally ILE-TYR, but also, VAL-TYR, ILE-LYS, ILE-PHE
Length always 7 residues.

CDR-L3:
Start—always 33 residues after end of L2
Residue before is always Cys
Residues after always PHE-GLY-XXX-GLY (SEQ ID NO: 21)
Length 7 to 11 residues CDR-H1:
Start—Approx residue 26 (always 4 after a CYS) [Chothia/AbM definition] Kabat definition starts 5 residues later Residues before always CYS-XXX-XXX-XXX (SEQ ID NO: 22)
Residues after always a TRP. Typically TRP-VAL, but also, TRP-ILE, TRP-ALA
Length 10 to 12 residues (AbM definition) Chothia definition excludes the last 4 residues
CDR-H2:
Start—always 15 residues after the end of Kabat/AbM definition) of CDR-H1 Residues before typically LEU-GLU-TRP-ILE-GLY (SEQ ID NO: 23), but a number of variations
Residues after LYS/ARG-LEU/ILE/VAL/PHE/THR/ALA-THR/SER/ILE/ALA Length Kabat definition 16 to 19 residues (AbM definition ends 7 residues earlier)
CDR-H3:
Start—always 33 residues after end of CDR-H2 (always 2 after a CYS)
Residues before always CYS-XXX-XXX (typically CYS-ALA-ARG)
Residues after always TRP-GLY-XXX-GLY (SEQ ID NO: 24)
Length 3 to 25 residues "CH2 domain"—As used herein, the term "CH2 domain" includes the region of a heavy chain molecule that usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain (Burton, Molec. Immunol. 22 (1985) 161-206).

"Derived from"—As used herein, the term "derived from" a designated protein (e.g. an anti-GPVI antibody or antigen-binding fragment thereof) refers to the origin of the protein. In an embodiment, the protein or amino acid sequence which is derived from a particular starting protein is a CDR sequence or sequence related thereto. In an embodiment, the amino acid sequence which is derived from a particular starting protein is not contiguous. For example, in an embodiment, one, two, three, four, five, or six CDRs are derived from a starting antibody. In an embodiment, the protein or amino acid sequence which is derived from a particular starting protein or amino acid sequence has an amino acid sequence that is essentially identical to that of the starting sequence, or a region thereof wherein the region consists of at least 3-5 amino acids, at least 5-10 amino acids, at least 10-20 amino acids, at least 20-30 amino acids, or at least 30-50 amino acids, or which is otherwise identifiable to one of ordinary skill in the art as having its origin in the starting sequence. In an embodiment, the one or more CDR sequences derived from the starting antibody are altered to produce variant CDR sequences, e.g. affinity variants, wherein the variant CDR sequences maintain GPVI binding activity.

"Diabodies"—As used herein, the term "diabodies" refers to small antibody fragments prepared by constructing sFv fragments (see sFv paragraph) with short linkers (about 5-10 residues) between the VH and VL domains such that interchain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 0404097; WO 1993/011161; and Holliger et al., Proc. Natl. Acad. Sci., 90:6444-6448 (1993).

"Engineered"—As used herein, the term "engineered" includes manipulation of nucleic acid or polypeptide molecules by synthetic means (e.g. by recombinant techniques, in vitro peptide synthesis, by enzymatic or chemical coupling of peptides or some combination of these techniques). Preferably, the antibodies of the invention are engineered, including for example, humanized and/or chimeric antibodies, and antibodies which have been engineered to improve one or more properties, such as antigen binding, stability/half-life or effector function.

"Epitope"—As used herein, the term "epitope" refers to a specific arrangement of amino acids located on a protein or proteins to which an antibody binds. Epitopes often consist of a chemically active surface grouping of molecules such as amino acids or sugar side chains, and have specific three dimensional structural characteristics as well as specific charge characteristics. Epitopes can be linear or conformational, i.e., involving two or more sequences of amino acids in various regions of the antigen that may not necessarily be contiguous.

"Framework region"—As used herein, the term "framework region" or "FR region" includes the amino acid residues that are part of the variable region, but are not part of the CDRs (e.g., using the Kabat/Chothia definition of CDRs). Therefore, a variable region framework is between about 100-120 amino acids in length but includes only those amino acids outside of the CDRs. For the specific example of a heavy chain variable region and for the CDRs as defined by Kabat/Chothia, framework region 1 may correspond to the domain of the variable region encompassing amino acids 1-25; framework region 2 may correspond to the domain of the variable region encompassing amino acids 36-49; framework region 3 may correspond to the domain of the variable region encompassing amino acids 67-98, and framework region 4 may correspond to the domain of the variable region from amino acids 110 to the end of the variable region. The framework regions for the light chain are similarly separated by each of the light chain variable region CDRs. In naturally occurring antibodies, the six CDRs present on each monomeric antibody are short, non-contiguous sequences of amino acids that are specifically positioned to form the antigen binding site as the antibody assumes its three dimensional configuration in an aqueous environment. The remainders of the heavy and light variable domains show less inter-molecular variability in amino acid sequence and are termed the framework regions. The framework regions largely adopt a [beta]-sheet conformation and the CDRs form loops which connect, and in some cases form part of, the [beta]-sheet structure. Thus, these framework regions act to form a scaffold that provides for positioning the six CDRs in correct orientation by inter-chain, non-covalent interactions. The antigen binding site formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

"Fragment"—As used herein, the term "fragment" refers to a part or region of an antibody or antibody chain comprising fewer amino acid residues than an intact or complete antibody or antibody chain. The term "antigen-binding fragment" refers to a protein fragment of an immunoglobulin or antibody that binds antigen or competes with intact antibody (i.e., with the intact antibody from which they were derived)

for antigen binding (i.e., specific binding to human GPVI). As used herein, the term "fragment" of an antibody molecule includes antigen-binding fragments of antibodies, for example, an antibody light chain variable domain (VL), an antibody heavy chain variable domain (VH), a single chain antibody (scFv), a F(ab')2 fragment, a Fab fragment, an Fd fragment, an Fv fragment, a single domain antibody fragment (DAb), a one-armed (monovalent) antibody, diabodies or any antigen-binding molecule formed by combination, assembly or conjugation of such antigen binding fragments. Fragments can be obtained, e.g., via chemical or enzymatic treatment of an intact or complete antibody or antibody chain or by recombinant means.

"Fv"—As used herein, the term "Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (three loops each from the H and L chain) that contribute to antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Heavy chain region"—As used herein, the term "heavy chain region" includes amino acid sequences derived from the constant domains of an immunoglobulin heavy chain. A protein comprising a heavy chain region comprises at least one of: a CH1 domain, a hinge (e.g., upper, middle, and/or lower hinge region) domain, a CH2 domain, a CH3 domain, or a variant or fragment thereof. In an embodiment, a binding molecule of the invention may comprise the Fc region of an immunoglobulin heavy chain (e.g., a hinge portion, a CH2 domain, and a CH3 domain). In another embodiment, a binding molecule of the invention lacks at least a region of a constant domain (e.g., all or part of a CH2 domain). In certain embodiments, at least one, and preferably all, of the constant domains are derived from a human immunoglobulin heavy chain. For example, in one preferred embodiment, the heavy chain region comprises a fully human hinge domain. In other preferred embodiments, the heavy chain region comprising a fully human Fc region (e.g., hinge, CH2 and CH3 domain sequences from a human immunoglobulin). In certain embodiments, the constituent constant domains of the heavy chain region are from different immunoglobulin molecules. For example, a heavy chain region of a protein may comprise a CH2 domain derived from an IgG1 molecule and a hinge region derived from an IgG3 or IgG4 molecule. In other embodiments, the constant domains are chimeric domains comprising regions of different immunoglobulin molecules. For example, a hinge may comprise a first region from an IgG1 molecule and a second region from an IgG3 or IgG4 molecule. As set forth above, it will be understood by one of ordinary skill in the art that the constant domains of the heavy chain region may be modified such that they vary in amino acid sequence from the naturally occurring (wild-type) immunoglobulin molecule. That is, the proteins of the invention disclosed herein may comprise alterations or modifications to one or more of the heavy chain constant domains (CH1, hinge, CH2 or CH3) and/or to the light chain constant domain (CL). Exemplary modifications include additions, deletions or substitutions of one or more amino acids in one or more domains.

"Hinge region"—As used herein, the term "hinge region" includes the region of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al., J. Immunol. 1998 161:4083).

The terms "hypervariable loop" and "complementarity determining region" are not strictly synonymous, since the hypervariable loops (HVs) are defined on the basis of structure, whereas complementarity determining regions (CDRs) are defined based on sequence variability (Kabat et al., Sequences of Proteins of Immunological Interest, 5th Ed. Public Health Service, National Institutes of Health, Bethesda, Md., 1983) and the limits of the HVs and the CDRs may be different in some VH and VL domains. The CDRs of the VL and VH domains can typically be defined by the Kabat/Chothia definition (see above). In one embodiment, the CDRs of the VL and VH domains may comprise the following amino acids: residues 24-39 (CDRL1), 55-61 (CDRL2) and 94-102 (CDRL3) in the light chain variable domain, and residues 26-35 (CDRH1), 50-66 (CDRH2) and 99-109 (CDRH3) in the heavy chain variable domain. Thus, the HVs may be comprised within the corresponding CDRs and references herein to the "hypervariable loops" of VH and VL domains should be interpreted as also encompassing the corresponding CDRs, and vice versa, unless otherwise indicated. The more highly conserved regions of variable domains are called the framework region (FR), as defined below. The variable domains of native heavy and light chains each comprise four FRs (FR1, FR2, FR3 and FR4, respectively), largely adopting a [beta]-sheet configuration, connected by the three hypervariable loops. The hypervariable loops in each chain are held together in close proximity by the FRs and, with the hypervariable loops from the other chain, contribute to the formation of the antigen-binding site of antibodies. Structural analysis of antibodies revealed the relationship between the sequence and the shape of the binding site formed by the complementarity determining regions (Chothia et al., J. Mol. Biol. 227: 799-817 (1992)); Tramontano et al., J. Mol. Biol, 215: 175-182 (1990)). Despite their high sequence variability, five of the six loops adopt just a small repertoire of main-chain conformations, called "canonical structures". These conformations are first of all determined by the length of the loops and secondly by the presence of key residues at certain positions in the loops and in the framework regions that determine the conformation through their packing, hydrogen bonding or the ability to assume unusual main-chain conformations.

"Humanized"—As used herein, the term "humanized" refers to chimeric immunoglobulins, immunoglobulin chains or fragments thereof (such as Fv, Fab, Fab', or other antigen-binding subsequences of antibodies) which contain minimal sequence derived from a murine immunoglobulin. For example, humanized antibodies are human immunoglobulins (recipient antibody) in which residues from a complementary-determining region (CDR) of the recipient are replaced by residues from a CDR of the original antibody (donor antibody) while maintaining the desired specificity, affinity, and capacity of the original antibody.

"Humanizing substitutions"—As used herein, the term "humanizing substitutions" refers to amino acid substitutions in which the amino acid residue present at a particular position in the VH or VL domain of a non-human anti-GPVI antibody (for example a murine anti-GPVI antibody) is replaced with an amino acid residue which occurs at an equivalent position in a reference human VH or VL domain. The reference human VH or VL domain may be a VH or VL domain encoded by the human germline, in which case the substituted residues may be referred to as "germlining substitutions". Humanizing/germlining substitutions may be made in the framework regions and/or the CDRs of an anti-GPVI antibody, defined herein.

"High human homology"—An antibody comprising a heavy chain variable domain (VH) and a light chain variable domain (VL) will be considered as having high human homology if the VH domains and the VL domains, taken together, exhibit at least 70, 75, 80, 85, 90, 95% or more amino acid sequence identity to the closest matching human germline VH and VL sequences. Antibodies having high human homology may include antibodies comprising VH and VL domains of native non-human antibodies which exhibit sufficiently high % sequence identity human germline sequences, as well as engineered, especially humanized, variants of such antibodies and also "fully human" antibodies. In an embodiment the VH domain of the antibody with high human homology may exhibit an amino acid sequence identity or sequence homology of 75%, 80% or greater with one or more human VH domains across the framework regions FR1, FR2, FR3 and FR4. In other embodiments the amino acid sequence identity or sequence homology between the VH domain of the protein of the invention and the closest matching human germline VH domain sequence may be 85% or greater, 90% or greater, 95% or greater, 97% or greater, or up to 99% or even 100%. In an embodiment the VH domain of the antibody with high human homology may contain one or more (e.g. 1 to 20) amino acid sequence mismatches across the framework regions FR1, FR2, FR3 and FR4, in comparison to the closest matched human VH sequence. In another embodiment the VL domain of the antibody with high human homology may exhibit a sequence identity or sequence homology of 80% or greater with one or more human VL domains across the framework regions FR1, FR2, FR3 and FR4. In other embodiments the amino acid sequence identity or sequence homology between the VL domain of the protein of the invention and the closest matching human germline VL domain sequence may be 85% or greater 90% or greater, 95% or greater, 97% or greater, or up to 99% or even 100%.

In an embodiment the VL domain of the antibody with high human homology may contain one or more (e.g. 1 to 20, preferably 1 to 10 and more preferably 1 to 5) amino acid sequence mismatches across the framework regions FR1, FR2, FR3 and FR4, in comparison to the closest matched human VL sequence. Before analyzing the percentage sequence identity between the antibody with high human homology and human germline VH and VL, the canonical folds may be determined, which allow the identification of the family of human germline segments with the identical combination of canonical folds for H1 and H2 or L1 and L2 (and L3). Subsequently the human germline family member that has the highest degree of sequence homology with the variable region of the antibody of interest is chosen for scoring the sequence homology. The determination of Chothia canonical classes of hypervariable loops L1, L2, L3, H1 and H2 can be performed with the bioinformatics tools publicly available on webpage www.bioinf.org.uk/abs/chothia.html.page. The output of the program shows the key residue requirements in a data file. In these data files, the key residue positions are shown with the allowed amino acids at each position. The sequence of the variable region of the antibody of interest is given as input and is first aligned with a consensus antibody sequence to assign the Kabat/Chothia numbering scheme. The analysis of the canonical folds uses a set of key residue templates derived by an automated method developed by Martin and Thornton (Martin et al., J. Mol. Biol. 263:800-815 (1996)). With the particular human germline V segment known, which uses the same combination of canonical folds for H1 and H2 or L1 and L2 (and L3), the best matching family member in terms of sequence homology can be determined. With bioinformatics tools the percentage sequence identity between the VH and VL domain framework amino acid sequences of the antibody of interest and corresponding sequences encoded by the human germline can be determined, but actually manual alignment of the sequences can be applied as well. Human immunoglobulin sequences can be identified from several protein data bases, such as VBase (vbase.mrc-cpe.cam.ac.uk/) or the Pluckthun/Honegger database (www.bioc.unizh.ch/antibody/Sequences/Germlines). To compare the human sequences to the V regions of VH or VL domains in an antibody of interest a sequence alignment algorithm such as available via websites like www.expasy.ch/tools/#align can be used, but also manual alignment with the limited set of sequences can be performed. Human germline light and heavy chain sequences of the families with the same combinations of canonical folds and with the highest degree of homology with the framework regions 1, 2, and 3 of each chain are selected and compared with the variable region of interest; also the FR4 is checked against the human germline JH and JK or JL regions. Note that in the calculation of overall percent sequence homology the residues of FR1, FR2 and FR3 are evaluated using the closest match sequence from the human germline family with the identical combination of canonical folds. Only residues different from the closest match or other members of the same family with the same combination of canonical folds are scored (NB—excluding any primer-encoded differences). However, for the purposes of humanization, residues in framework regions identical to members of other human germline families, which do not have the same combination of canonical folds, can be considered "human", despite the fact that these are scored "negative" according to the stringent conditions described above. This assumption is based on the "mix and match" approach for humanization, in which each of FR1, FR2, FR3 and FR4 is separately compared to its closest matching human germline sequence and the humanized molecule therefore contains a combination of different FRs as was done by Qu and colleagues (Qu et al., Clin. Cancer Res. 5:3095-3100 (1999)) and Ono and colleagues (Ono et al., Mol. Immunol. 36:387-395 (1999)). The boundaries of the individual framework regions may be assigned using the IMGT numbering scheme, which is an adaptation of the numbering scheme of Chothia (Lefranc et al., Nucleic acid res 27: 209-212 (1999); im.gt.cines.fr). Antibodies with high human homology may comprise hypervariable loops or CDRs having human or human-like canonical folds, as discussed in detail below. In an embodiment at least one hypervariable loop or CDR in either the VH domain or the VL domain of the antibody with high human homology may be obtained or derived from a VH or VL domain of a non-human antibody, yet exhibit a predicted or actual canonical fold structure which is substantially identical to a canonical fold structure which occurs in human antibodies. It is well established in the art that although the primary amino acid sequences of hypervariable loops present in both VH domains and VL domains encoded by the human germline are, by definition, highly variable, all hypervariable loops, except CDR H3 of the VH domain, adopt only a few distinct structural conformations, termed canonical folds (Chothia et al., J. Mol. Biol. 196:901-917 (1987); Tramontano et al., Proteins 6:382-94 (1989)), which depend on both the length of the hypervariable loop and presence of the so-called canonical amino acid residues (Chothia et al., J. Mol. Biol. 196:901-917 (1987)). Actual canonical structures of the hypervariable loops in intact VH or VL domains can be determined by structural analysis (e.g. X-ray crystallography), but it is also possible to predict canonical structure on the basis of key amino acid residues which are characteristic of a particular structure (discussed further below). In essence, the specific pattern of residues that determines each canonical structure forms a "signature" which enables the canonical structure to be recognized in hypervariable loops of a VH or VL domain of unknown structure; canonical structures can therefore be predicted on the basis of primary amino acid sequence alone. The predicted canonical fold structures for the hypervariable loops of any given VH or VL sequence in an antibody with high human homology can be analyzed using algorithms which are publicly available from www.bioinforg.uk/abs/chothia.html, www.biochem.ucl.ac.uk/~martin/antibodies.html and www.bioc.unizh.ch/antibody/Sequences/GermlinesN-base_hVk.html. These tools permit query VH or VL sequences to be aligned against human VH or VL domain sequences of known canonical structure, and a prediction of canonical structure made for the hypervariable loops of the query sequence. In the case of the VH domain, H1 and H2 loops may be scored as having a canonical fold structure "substantially identical" to a canonical fold structure known to occur in human antibodies if at least the first, and preferable both, of the following criteria are fulfilled:

1. An identical length, determined by the number of residues, to the closest matching human canonical structural class.

2. At least 33% identity, preferably at least 50% identity with the key amino acid residues described for the corresponding human H1 and H2 canonical structural classes (note for the purposes of the foregoing analysis the H1 and H2 loops are treated separately and each compared against its closest matching human canonical structural class). The foregoing analysis relies on prediction of the canonical structure of the H1 and H2 loops of the antibody of interest. If the actual structures of the H1 and H2 loops in the antibody of interest are known, for example based on X-ray crystallography, then the H1 and H2 loops in the antibody of interest may also be scored as having a canonical fold structure "substantially identical" to a canonical fold structure known to occur in human antibodies if the length of the loop differs from that of the closest matching human canonical structural class (typically by +1 or +2 amino acids) but the actual structure of the H1 and H2 loops in the antibody of interest matches the structure of a human canonical fold. Key amino acid residues found in the human canonical structural classes for the first and second hypervariable loops of human VH domains (H1 and H2) are described by Chothia et al., J. Mol. Biol. 227:799-817 (1992), the contents of which are incorporated herein in their entirety by reference. In particular, Table 3 on page 802 of Chothia et al., which is specifically incorporated herein by reference, lists preferred amino acid residues at key sites for H1 canonical structures found in the human germline, whereas Table 4 on page 803, also specifically incorporated by reference, lists preferred amino acid residues at key sites for CDR H2 canonical structures found in the human germline. In an embodiment, both HI and H2 in the VH domain of the antibody with high human homology exhibit a predicted or actual canonical fold structure which is substantially identical to a canonical fold structure which occurs in human antibodies. Antibodies with high human homology may comprise a VH domain in which the hypervariable loops H1 and H2 form a combination of canonical fold structures which is identical to a combination of canonical structures known to occur in at least one human germline VH domain. It has been observed that only certain combinations of canonical fold structures at H1 and H2 actually occur in VH domains encoded by the human germline. In an embodiment H1 and H2 in the VH domain of the antibody with high human homology may be obtained from a VH domain of a non-human species, yet form a combination of predicted or actual canonical fold structures which is identical to a combination of canonical fold structures known to occur in a human germline or somatically mutated VH domain. In non-limiting embodiments H1 and H2 in the VH domain of the antibody with high human homology may be obtained from a VH domain of a non-human species, and form one of the following canonical fold combinations: 1-1, 1-2, 1-3, 1-6, 1-4, 2-1, 3-1 and 3-5. An antibody with high human homology may contain a VH domain which exhibits both high sequence identity/sequence homology with human VH, and which contains hypervariable loops exhibiting structural homology with human VH. It may be advantageous for the canonical folds present at H1 and H2 in the VH domain of the antibody with high human homology, and the combination thereof, to be "correct" for the human VH germline sequence which represents the closest match with the VH domain of the antibody with high human homology in terms of overall primary amino acid sequence identity. By way of example, if the closest sequence match is with a human germline VH3 domain, then it may be advantageous for H1 and H2 to form a combination of canonical folds which also occurs naturally in a human VH3 domain. This may be particularly important in the case of antibodies with high human homology which are derived from non-human species, e.g. antibodies containing VH and VL domains which are derived from camelid conventional antibodies, especially antibodies containing humanized camelid VH and VL domains. Thus, in an embodiment the VH domain of the anti-GPVI antibody with high human homology may exhibit a sequence identity or sequence homology of 70% or greater, 80% or greater, 85% or greater, 90% or greater, 95% or greater, 97% or greater, or up to 99% or even 100% with a human VH domain across the framework regions FR1, FR2, FR3 and FR4, and in addition H1 and H2 in the same antibody are obtained from a non-human VH domain, but form a combination of predicted or actual canonical fold structures which is the same as a canonical fold combination known to occur naturally in the same human VH domain. In other embodiments, L1 and L2 in the VL domain of the antibody with high human homology are each obtained from a VL domain of a non-human species, and each exhibits a predicted or actual canonical fold structure which is substantially identical to a canonical fold structure which occurs in human antibodies. As with the VH domains, the hypervariable loops of VL domains of both VLambda and VKappa types can adopt a limited number of conformations or canonical structures, determined in part by length and also by the presence of key amino acid residues at certain canonical positions. Within an antibody of interest having high human homology, L1, L2 and L3 loops obtained from a VL domain of a non-human species, e.g. a Camelidae species, may be scored as having a canonical fold structure "substantially identical" to a canonical fold structure known to occur in human antibodies if at least the first, and preferable both, of the following criteria are fulfilled:

1. An identical length, determined by the number of residues, to the closest matching human structural class.

2. At least 33% identity, preferably at least 50% identity with the key amino acid residues described for the corresponding human L1 or L2 canonical structural classes, from either the VLambda or the VKappa repertoire (note for the purposes of the foregoing analysis the L1 and L2 loops are treated separately and each compared against its closest matching human canonical structural class). The foregoing analysis relies on prediction of the canonical structure of the L1, L2 and L3 loops in the VL domain of the antibody of interest. If the actual structure of the L1, L2 and L3 loops is known, for example based on X-ray crystallography, then L1, L2 or L3 loops derived from the antibody of interest may also be scored as having a canonical fold structure "substantially identical" to a canonical fold structure known to occur in human antibodies if the length of the loop differs from that of the closest matching human canonical structural class (typically by +1 or +2 amino acids) but the actual structure of the loops in the antibody of interest matches a human canonical fold. Key amino acid residues found in the human canonical structural classes for the CDRs of human VLambda and VKappa domains are described by Morea et al., Methods, 20: 267-279 (2000) and Martin et al., J. Mol. Biol., 263:800-815 (1996). The structural repertoire of the human VKappa domain is also described by Tomlinson et al., EMBO J. 14:4628-4638 (1995), and that of the VLambda domain by Williams et al., J. Mol. Biol., 264: 220-232 (1996). The contents of all these documents are to be incorporated herein by reference. L1 and L2 in the VL domain of an antibody with high human homology may form a combination of predicted or actual canonical fold structures which is identical to a combination of canonical fold structures known to occur in a human germline VL domain. In non-limiting embodiments LI and L2 in the VLambda domain of an antibody with high human homology may form one of the following canonical fold combinations: 11-7, 13-7(A,B,C), 14-7(A,B), 12-11, 14-11 and 12-12 (as defined in Williams et al., J. Mol. Biol. 264:220-32 (1996) and as shown on www.bioc.uzh.ch/antibody/Sequences/GermlinesNBase_hVL.html). In non-limiting embodiments L1 and L2 in the VKappa domain may form one of the following canonical fold combinations: 2-1, 3-1, 4-1 and 6-1 (as defined in Tomlinson et al., EMBO J. 14:4628-38 (1995) and as shown on www.bioc.uzh.ch/antibody/Sequences/GermlinesNBase_hVK.html).

In a further embodiment, all three of L1, L2 and L3 in the VL domain of an antibody with high human homology may exhibit a substantially human structure. It is preferred that the VL domain of the antibody with high human homology exhibit both high sequence identity/sequence homology with human VL, and also that the hypervariable loops in the VL domain exhibit structural homology with human VL.

In an embodiment, the VL domain of the anti-GPVI antibody with high human homology may exhibit a sequence identity of 70% or greater, 80% or greater, 85% or greater, 90% or greater, 95% or greater, 97% or greater, or up to 99% or even 100% with a human VL domain across the framework regions FR1, FR2, FR3 and FR4, and in addition hypervariable loop L1 and hypervariable loop L2 may form a combination of predicted or actual canonical fold structures which is the same as a canonical fold combination known to occur naturally in the same human VL domain. It is, of course, envisaged that VH domains exhibiting high sequence identity/sequence homology with human VH, and also structural homology with hypervariable loops of human VH will be combined with VL domains exhibiting high sequence identity/sequence homology with human VL, and also structural homology with hypervariable loops of human VL to provide antibodies with high human homology containing VH/VL pairings with maximal sequence and structural homology to human-encoded VH/VL pairings.

"Immunospecific", "specific for" or to "specifically bind"—As used herein, an antibody is said to be "immunospecific", "specific for" or to "specifically bind" an antigen if it reacts at a detectable level with the antigen, preferably with an affinity constant, $K_A$, of greater than or equal to about $10^6$ $M^{-1}$, greater than or equal to about $10^7$ $M^{-1}$, or greater than or equal to $10^8$ $M^{-1}$, or greater than or equal to $1.5\ 10^8$ $M^{-1}$, or greater than or equal to $10^9$ $M^{-1}$ or greater than or equal to $5\ 10^9$ $M^{-1}$. Affinity of an antibody for its cognate antigen is also commonly expressed as a dissociation constant $K_D$, and in certain embodiments, an antibody specifically binds to antigen if it binds with a $K_D$ of less than or equal to $10^{-6}$ M, less than or equal to $10^{-7}$ M, or less than or equal to $1.5\ 10^{-8}$ M, or less than or equal to $10^{-8}$ M, or less than or equal to $5\ 10^{-9}$ M or less than or equal to $10^{-9}$ M. Affinities of antibodies can be readily determined using conventional techniques, for example, those described by Scatchard G et al. (The attractions of proteins for small molecules and ions. *Ann NY Acad Sci* 1949; 51: 660-672). Binding properties of an antibody to antigens, cells or tissues thereof may generally be determined and assessed using immunodetection methods including, for example, ELISA, immunofluorescence-based assays, such as immuno-histochemistry (IHC) and/or fluorescence-activated cell sorting (FACS) or by surface plasmon resonance (SPR, BIAcore).

"Isolated nucleic acid"—As used herein, an "isolated nucleic acid" is a nucleic acid that is substantially separated from other genome DNA sequences as well as proteins or complexes such as ribosomes and polymerases, which naturally accompany a native sequence. The term embraces a nucleic acid sequence that has been removed from its naturally occurring environment, and includes recombinant or cloned DNA isolates and chemically synthesized analogues or analogues biologically synthesized by heterologous systems. A substantially pure nucleic acid includes isolated forms of the nucleic acid. Of course, this refers to the nucleic acid as originally isolated and does not exclude genes or sequences later added to the isolated nucleic acid by the hand of man.

The term "polypeptide" is used in its conventional meaning, i.e., as a sequence of less than 100 amino acids. A polypeptide usually refers to a monomeric entity. The term "protein" refers to a sequence of more than 100 amino acids and/or to a multimeric entity. The proteins of the invention are not limited to a specific length of the product. This term does not refer to or exclude post-expression modifications of the protein, for example, glycosylation, acetylation, phosphorylation and the like, as well as other modifications known in the art, both naturally occurring and non-naturally occurring. A protein may be an entire protein, or a subsequence thereof. Particular proteins of interest in the context of this invention are amino acid subsequences comprising CDRs and being capable of binding an antigen. An "isolated protein" is one that has been identified and separated and/or recovered from a component of its natural environment. In preferred embodiments, the isolated protein will be purified (1) to greater than 80, 85, 90, 95% by weight of protein as determined by the Lowry method, and most preferably more than 96, 97, 98, or 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver staining. Isolated protein includes the protein in situ within recombinant cells since at least one component of the protein's natural environment will not be present. Ordinarily, however, isolated protein will be prepared by at least one purification step.

"Identity" or "identical"—As used herein, the term "identity" or "identical", when used in a relationship between the sequences of two or more amino acid sequences, refers to the degree of sequence relatedness between amino acid sequences, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related amino acid sequences can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988). Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. \2, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al., NCB/NLM/NIH Bethesda, Md. 20894; Altschul et al., supra). The well-known Smith Waterman algorithm may also be used to determine identity.

"Modified antibody"—As used herein, the term "modified antibody" includes synthetic forms of antibodies which are altered such that they are not naturally occurring, e.g., antibodies that comprise at least two heavy chain regions but not two complete heavy chains (such as, domain deleted antibodies or minibodies); multispecific forms of antibodies (e.g., bispecific, trispecific, etc.) altered to bind to two or more different antigens or to different epitopes on a single antigen; heavy chain molecules joined to scFv molecules and the like. ScFv molecules are known in the art and are described, e.g., in U.S. Pat. No. 5,892,019. In addition, the term "modified antibody" includes multivalent forms of antibodies (e.g., trivalent, tetravalent, etc., antibodies that bind to three or more copies of the same antigen). In another embodiment, a modified antibody of the invention is a fusion protein comprising at least one heavy chain region lacking a CH2 domain and comprising a binding domain of a protein comprising the binding region of one member of a receptor ligand pair.

"Mammal"—As used herein, the term "mammal" refers to any mammal, including humans, domestic and farm animals, and zoo, sports, or pet animals, such as dogs, cats, cattle, horses, sheep, pigs, goats, rabbits, etc. Preferably, the mammal is a primate, more preferably a human.

"Monoclonal antibody"—As used herein, the term "monoclonal antibody" refers to an antibody obtained from a population of substantially homogeneous antibodies, i.e., the individual antibodies comprised in the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

"Native sequence"—As used herein, the term "native sequence" nucleotide refers to a polynucleotide that has the same nucleotide sequence as a polynucleotide derived from nature. Accordingly, a "native sequence" protein is one that has the same amino acid sequence as a protein (e.g., antibody) derived from nature (e.g., from any species). Such native sequence polynucleotides and proteins can be isolated from nature or can be produced by recombinant or synthetic means. A polynucleotide "variant", as the term is used herein, is a polynucleotide that typically differs from a polynucleotide specifically disclosed herein in one or more substitutions, deletions, additions and/or insertions. Such variants may be naturally occurring or may be synthetically generated, for example, by modifying one or more of the polynucleotide sequences of the invention and evaluating one or more biological activities of the encoded proteins as described herein and/or using any of a number of techniques well known in the art. A protein "variant", as the term is used herein, is a protein that typically differs from a protein specifically disclosed herein in one or more substitutions, deletions, additions and/or insertions. Such variants may be naturally occurring or may be synthetically generated, for example, by modifying one or more of the above protein sequences of the invention and evaluating one or more biological activities of the protein as described herein and/or using any of a number of techniques well known in the art. Modifications may be made in the structure of the polynucleotides and proteins of the present invention and still obtain a functional molecule that encodes a variant or derivative protein with desirable characteristics. When it is desired to alter the amino acid sequence of a protein to create an equivalent, or even an improved, variant or region of a protein of the invention, one skilled in the art will typically change one or more of the codons of the encoding DNA sequence. For example, certain amino acids may be substituted for other amino acids in a protein structure without appreciable loss of its ability to bind other proteins (e.g., antigens) or cells. Since it is the binding capacity and nature of a protein that defines that protein's biological functional activity, certain amino acid sequence substitutions can be made in a protein sequence, and of course, its underlying DNA coding sequence, and nevertheless obtain a protein with similar properties. It is thus contemplated that various changes may be made in the amino acid sequences of the disclosed compositions, or corresponding DNA sequences that encode said proteins without appreciable loss of their biological utility or activity. In many instances, a protein variant will contain one or more conservative substitutions. A "conservative substitution" is one in which an amino acid is substituted for another amino acid that has similar properties, such that one skilled in the art of peptide chemistry would expect the secondary structure and hydropathic nature of the protein to be substantially unchanged. As outlined above, amino acid substitutions are generally therefore based on the relative similarity of the amino acid side-chain substituents, for example, their hydrophobicity, hydrophilicity, charge, size, and the like. Exemplary substitutions that take several of the foregoing characteristics into consideration are well known to those of skill in the art and include: arginine and lysine; glutamate and aspartate; serine and threonine; glutamine and asparagine; and valine, leucine and isoleucine. Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain non-conservative changes. In a preferred embodiment, variant proteins differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the protein.

"Pharmaceutically acceptable excipient"—As used herein, the term "pharmaceutically acceptable excipient" includes any and all solvents, dispersion media, coatings, antibacterial and antifungal agents, isotonic and absorption delaying agents and the like. Said excipient does not produce an adverse, allergic or other untoward reaction when administered to an animal, preferably a human. For human administration, preparations should meet sterility, pyrogenicity, and general safety and purity standards as required by regulatory offices, such as, for example, FDA Office or EMA.

"Specificity"—As used herein, the term "specificity" refers to the ability to specifically bind (e.g., immunoreact with) a given target, e.g., GPVI. A protein may be monospecific and contain one or more binding sites which specifically bind a target, or a protein may be multispecific and contain two or more binding sites which specifically bind the same or different targets. In an embodiment, an antibody of the invention is specific for more than one target. For example, in an embodiment, a multispecific binding molecule of the invention binds to GPVI and a second molecule.

"Single-chain Fv" also abbreviated as "sFv" or "scFv"—As used herein, the terms "Single-chain Fv", "sFv" or "scFv" are antibody fragments that comprise the VH and VL antibody domains connected into a single amino acid chain. Preferably, the sFv amino acid sequence further comprises a peptidic linker between the VH and VL domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

"Subject"—As used herein, the term "subject" refers to a mammal, preferably a human. In one embodiment, a subject may be a "patient", i.e. a warm-blooded animal, more preferably a human, who/which is awaiting the receipt of, or is receiving medical care or was/is/will be the object of a medical procedure, or is monitored for the development of a disease.

"Synthetic"—As used herein, the term "synthetic" with respect to proteins includes proteins which comprise an amino acid sequence that is not naturally occurring. For example, non-naturally occurring proteins are modified forms of naturally occurring proteins (e.g., comprising a mutation such as an addition, substitution or deletion) or proteins which comprise a first amino acid sequence (which may or may not be naturally occurring) that is linked in a linear sequence of amino acids to a second amino acid sequence (which may or may not be naturally occurring) to which it is not naturally linked in nature.

"Therapeutically effective amount" means level or amount of agent that is aimed at, without causing significant negative or adverse side effects to the target, (1) delaying or preventing the onset of GPVI-related disease; (2) slowing down or stopping the progression, aggravation, or deterioration of one or more symptoms of the GPVI-related disease; (3) bringing about ameliorations of the symptoms of the GPVI-related disease; (4) reducing the severity or incidence of the GPVI-related disease; or (5) curing the GPVI-related disease. A therapeutically effective amount may be administered prior to the onset of the GPVI-related disease, for a prophylactic or preventive action. Alternatively or additionally, the therapeutically effective amount may be administered after initiation of the GPVI-related disease, for a therapeutic action.

"Variable region" or "variable domain"—As used herein, the term "variable" refers to the fact that certain regions of the variable domains VH and VL differ extensively in sequence among antibodies and are used in the binding and specificity of each particular antibody for its target antigen. However, the variability is not evenly distributed throughout the variable domains of antibodies. It is concentrated in three segments called "hypervariable loops" in each of the VL domain and the VH domain which form part of the antigen binding site. The first, second and third hypervariable loops of the VLambda light chain domain are referred to herein as L1 (λ), L2 (λ) and L3 (λ) and may be defined as comprising residues 24-33 (L1(λ), consisting of 9, 10 or 11 amino acid residues), 49-53 L2 (λ), consisting of 3 residues) and 90-96 (L3(λ), consisting of 6 residues) in the VL domain (Morea et al., Methods 20:267-279 (2000)). The first, second and third hypervariable loops of the VKappa light chain domain are referred to herein as L1(κ), L2(κ) and L3(κ) and may be defined as comprising residues 25-33 (L1(κ), consisting of 6, 7, 8, 11, 12 or 13 residues), 49-53 (L2(κ), consisting of 3 residues) and 90-97 (L300, consisting of 6 residues) in the VL domain (Morea et al., Methods 20:267-279 (2000)). The first, second and third hypervariable loops of the VH domain are referred to herein as H1, H2 and H3 and may be defined as comprising residues 25-33 (HI, consisting of 7, 8 or 9 residues), 52-56 (H2, consisting of 3 or 4 residues) and 91-105 (H3, highly variable in length) in the VH domain (Morea et al., Methods 20:267-279 (2000)). Unless otherwise indicated, the terms L1, L2 and L3 respectively refer to the first, second and third hypervariable loops of a VL domain, and encompass hypervariable loops obtained from both VKappa and VLambda isotypes. The terms H1, H2 and H3 respectively refer to the first, second and third hypervariable loops of the VH domain, and encompass hypervariable loops obtained from any of the known heavy chain isotypes, including [gamma], [epsilon], [delta], [alpha] or [mu]. The hypervariable loops L1, L2, L3, H1, H2 and H3 may each comprise part of a "complementarity determining region" or "CDR", as defined hereinabove.

"Valency"—As used herein, the term "valency" refers to the number of potential target binding sites in a protein. Each target binding site specifically binds one target molecule or specific site on a target molecule. When a protein comprises more than one target binding site, each target binding site may specifically bind the same or different molecules (e.g., may bind to different ligands or different antigens, or different epitopes on the same antigen). The subject binding molecules preferably have at least one binding site specific for a human GPVI molecule. Preferably, the proteins provided herein are monovalent.

"Treating" or "treatment" or "alleviation"—As used herein, the terms "treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for the targeted pathologic condition or disorder if, after receiving a therapeutic amount of a protein according to the present invention, the patient shows observable and/or measurable reduction in or absence of one or more of the following: reduction in the number of pathogenic cells; reduction in the percent of total cells that are pathogenic; and/or relief to some extent, of one or more of the symptoms associated with the specific disease or condition; reduced morbidity and mortality, and improvement in quality of life issues. The above parameters for assessing successful treatment and improvement in the disease are readily measurable by routine procedures familiar to a physician.

The present invention relates to isolated humanized proteins binding to human GPVI, preferably to isolated humanized antibodies against human GPVI. In one embodiment, the isolated protein of the invention is purified.

In one embodiment, the protein of the invention binds to the extracellular domain of GPVI.

In one embodiment, the protein of the invention binds to the Ig-like C2-type domain 2 (D2) of human GPVI.

Thus, in one embodiment, the protein of the invention binds to an epitope comprising at least one amino acid residue from amino acid residues 114 to 207 of human GPVI (SEQ ID NO: 13) or from a sequence sharing at least 60%, 70%, 75%, 80%, 90%, 95%, 96%, 97%, 98%, 99% of identity over amino acid residues 114 to 207 of human GPVI (SEQ ID NO: 13).

In one embodiment, said epitope comprises at least one amino acid residue from amino acid residues 114 to 187, preferably from 115 to 187, more preferably from 116 to 187, more preferably from 117 to 187, more preferably from 118 to 186, more preferably from 119 to 185, more preferably from 120 to 184, even more preferably from 121 to 183 of human GPVI (SEQ ID NO: 13), or from a sequence sharing at least 60%, 70%, 75%, 80%, 90%, 95%, 96%, 97%, 98%, 99% of identity over amino acid residues 114 to 187, preferably from 115 to 187, more preferably from 116 to 187, more preferably from 117 to 187, more preferably from 118 to 186, more preferably from 119 to 185, more preferably from 120 to 184, even more preferably from 121 to 183 of human GPVI (SEQ ID NO: 13).

In one embodiment, said epitope comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more amino acid residues from amino acid residues 114 to 187, preferably from 115 to 187, more preferably from 116 to 187, more preferably from 117 to 187, more preferably from 118 to 186, more preferably from 119 to 185, more preferably from 120 to 184, even more preferably from 121 to 183 of human GPVI (SEQ ID NO: 13), or from a sequence sharing at least 60%, 70%, 75%, 80%, 90%, 95%, 96%, 97%, 98%, 99% of identity over amino acid residues 114 to 187, preferably from 115 to 187, more preferably from 116 to 187, more preferably from 117 to 187, more preferably from 118 to 186, more preferably from 119 to 185, more preferably from 120 to 184, even more preferably from 121 to 183 of human GPVI (SEQ ID NO: 13).

In one embodiment, said epitope comprises at least one amino acid residue from amino acid residues 114 to 142, preferably from 115 to 141, more preferably from 116 to 140, more preferably from 117 to 139, more preferably from 118 to 138, more preferably from 119 to 137, more preferably from 120 to 136, even more preferably from 121 to 135 of human GPVI (SEQ ID NO: 13), or from a sequence sharing at least 60%, 70%, 75%, 80%, 90%, 95%, 96%, 97%, 98%, 99% of identity over amino acid residues 114 to 142, preferably from 115 to 141, more preferably from 116 to 140, more preferably from 117 to 139, more preferably from 118 to 138, more preferably from 119 to 137, more preferably from 120 to 136, even more preferably from 121 to 135 of human GPVI (SEQ ID NO: 13).

In one embodiment, said epitope comprises at least 1, 2, 3, 4, 5, 6, 7, 8, 9, 10, 11, 12, 13, 14, 15, 16, 17, 18, 19, 20, 21, 22, 23, 24, 25, 26, 27, 28 of amino acid residues from 114 to 142, preferably from 115 to 141, more preferably from 116 to 140, more preferably from 117 to 139, more preferably from 118 to 138, more preferably from 119 to 137, more preferably from 120 to 136, even more preferably from 121 to 135 of human GPVI (SEQ ID NO: 13), or from a sequence sharing at least 60%, 70%, 75%, 80%, 90%, 95%, 96%, 97%, 98%, 99% of identity over amino acid residues 114 to 142, preferably from 115 to 141, more preferably from 116 to 140, more preferably from 117 to 139, more preferably from 118 to 138, more preferably from 119 to 137, more preferably from 120 to 136, even more preferably from 121 to 135 of human GPVI (SEQ ID NO: 13).

In one embodiment, said epitope comprises at least one amino acid residue from amino acid residues 114 to 135, preferably from 115 to 135, more preferably from 116 to 135, more preferably from 117 to 135, more preferably from 118 to 135, more preferably from 119 to 135, more preferably from 120 to 135, even more preferably from 121 to 135 of human GPVI (SEQ ID NO: 13), or from a sequence sharing at least 60%, 70%, 75%, 80%, 90%, 95%, 96%, 97%, 98%, 99% of identity over amino acid residues 114 to 135, preferably from 115 to 135, more preferably from 116 to 135, more preferably from 117 to 135, more preferably from 118 to 135, more preferably from 119 to 135, more preferably from 120 to 135, even more preferably from 121 to 135 of human GPVI (SEQ ID NO: 13).

In one embodiment, said epitope comprises at least 1, 2, 3, 4, 5, 6, 7, 8, 9, 10, 11, 12, 13, 14, 15, 16, 17, 18, 19, 20, 21 of amino acid residues from 114 to 135, preferably from 115 to 135, more preferably from 116 to 135, more preferably from 117 to 135, more preferably from 118 to 135, more preferably from 119 to 135, more preferably from 120 to 135, even more preferably from 121 to 135 of human GPVI (SEQ ID NO: 13), or from a sequence sharing at least 60%, 70%, 75%, 80%, 90%, 95%, 96%, 97%, 98%, 99% of identity over amino acid residues 114 to 135, preferably from 115 to 135, more preferably from 116 to 135, more preferably from 117 to 135, more preferably from 118 to 135, more preferably from 119 to 135, more preferably from 120 to 135, even more preferably from 121 to 135 of human GPVI (SEQ ID NO: 13).

In one embodiment, said epitope comprises at least one amino acid residue from amino acid residues 165 to 187, preferably from 166 to 186, more preferably from 167 to 185, more preferably from 168 to 184, even more preferably from 169 to 183 of human GPVI (SEQ ID NO: 13), or from a sequence sharing at least 60%, 70%, 75%, 80%, 90%, 95%, 96%, 97%, 98%, 99% of identity over amino acid residues 165 to 187, preferably from 166 to 186, more preferably from 167 to 185, more preferably from 168 to 184, even more preferably from 169 to 183 of human GPVI (SEQ ID NO: 13).

In one embodiment, said epitope comprises at least 1, 2, 3, 4, 5, 6, 7, 8, 9, 10, 11, 12, 13, 14, 15, 16, 17, 18, 19, 20, 21, 22 of amino acid residues from 165 to 187, preferably from 166 to 186, more preferably from 167 to 185, more preferably from 168 to 184, even more preferably from 169 to 183 of human GPVI (SEQ ID NO: 13), or from a sequence sharing at least 60%, 70%, 75%, 80%, 90%, 95%, 96%, 97%, 98%, 99% of identity over amino acid residues 165 to 187, preferably from 166 to 186, more preferably from 167 to 185, more preferably from 168 to 184, even more preferably from 169 to 183 of human GPVI (SEQ ID NO: 13).

In one embodiment, the isolated protein of the invention binds to a conformational epitope.

In one embodiment, said conformational epitope comprises at least one amino acid residue of human GPVI.

In one embodiment, said conformational epitope comprises at least one amino acid residue of the Ig-like C2-type domain 2 (D2) of human GPVI.

In one embodiment, said conformational epitope comprises at least one amino acid residue from 114 to 207 of human GPVI (SEQ ID NO: 13).

In one embodiment, said conformational epitope comprises at least one amino acid residue from amino acid residues 114 to 187, preferably from 115 to 187, more preferably from 116 to 187, more preferably from 117 to 187, more preferably from 118 to 186, more preferably from 119 to 185, more preferably from 120 to 184, even more preferably from 121 to 183 of human GPVI (SEQ ID NO: 13), or from a sequence sharing at least 60%, 70%, 75%, 80%, 90%, 95%, 96%, 97%, 98%, 99% of identity over amino acid residues 114 to 187, preferably from 115 to 187, more preferably from 116 to 187, more preferably from 117 to 187, more preferably from 118 to 186, more preferably from 119 to 185, more preferably from 120 to 184, even more preferably from 121 to 183 of human GPVI (SEQ ID NO: 13).

In one embodiment, said conformational epitope comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more amino acid residues from amino acid residues 114 to 187, preferably from 115 to 187, more preferably from 116 to 187, more preferably from 117 to 187, more preferably from 118 to 186, more preferably from 119 to 185, more preferably from 120 to 184, even more preferably from 121 to 183 of human GPVI (SEQ ID NO: 13), or from a sequence sharing at least 60%, 70%, 75%, 80%, 90%, 95%, 96%, 97%, 98%, 99% of identity over amino acid residues 114 to 187, preferably from 115 to 187, more preferably from 116 to 187, more preferably from 117 to 187, more preferably from 118 to 186, more preferably from 119 to 185, more preferably from 120 to 184, even more preferably from 121 to 183 of human GPVI (SEQ ID NO: 13).

In one embodiment, said conformational epitope comprises at least one amino acid residue from amino acid residues 114 to 142, preferably from 115 to 141, more preferably from 116 to 140, more preferably from 117 to 139, more preferably from 118 to 138, more preferably from 119 to 137, more preferably from 120 to 136, even more preferably from 121 to 135 of human GPVI (SEQ ID NO: 13), or from a sequence sharing at least 60%, 70%, 75%, 80%, 90%, 95%, 96%, 97%, 98%, 99% of identity over amino acid residues 114 to 142, preferably from 115 to 141, more preferably from 116 to 140, more preferably from 117 to 139, more preferably from 118 to 138, more preferably from 119 to 137, more preferably from 120 to 136, even more preferably from 121 to 135 of human GPVI (SEQ ID NO: 13).

In one embodiment, said conformational epitope comprises at least 1, 2, 3, 4, 5, 6, 7, 8, 9, 10, 11, 12, 13, 14, 15, 16, 17, 18, 19, 20, 21, 22, 23, 24, 25, 26, 27, 28 amino acid residues from amino acid residues 114 to 142, preferably from 115 to 141, more preferably from 116 to 140, more preferably from 117 to 139, more preferably from 118 to 138, more preferably from 119 to 137, more preferably from 120 to 136, even more preferably from 121 to 135 of human GPVI (SEQ ID NO: 13), or from a sequence sharing at least 60%, 70%, 75%, 80%, 90%, 95%, 96%, 97%, 98%, 99% of identity over amino acid residues 114 to 142, preferably from 115 to 141, more preferably from 116 to 140, more preferably from 117 to 139, more preferably from 118 to 138, more preferably from 119 to 137, more preferably from 120 to 136, even more preferably from 121 to 135 of human GPVI (SEQ ID NO: 13).

In one embodiment, said conformational epitope comprises at least one amino acid residue from amino acid residues 114 to 135, preferably from 115 to 135, more preferably from 116 to 135, more preferably from 117 to 135, more preferably from 118 to 135, more preferably from 119 to 135, more preferably from 120 to 135, even more preferably from 121 to 135 of human GPVI (SEQ ID NO: 13), or from a sequence sharing at least 60%, 70%, 75%, 80%, 90%, 95%, 96%, 97%, 98%, 99% of identity over amino acid residues 114 to 135, preferably from 115 to 135, more preferably from 116 to 135, more preferably from 117 to 135, more preferably from 118 to 135, more preferably from 119 to 135, more preferably from 120 to 135, even more preferably from 121 to 135 of human GPVI (SEQ ID NO: 13).

In one embodiment, said conformational epitope comprises at least 1, 2, 3, 4, 5, 6, 7, 8, 9, 10, 11, 12, 13, 14, 15, 16, 17, 18, 19, 20, 21 amino acid residues from amino acid residues 114 to 135, preferably from 115 to 135, more preferably from 116 to 135, more preferably from 117 to 135, more preferably from 118 to 135, more preferably from 119 to 135, more preferably from 120 to 135, even more preferably from 121 to 135 of human GPVI (SEQ ID NO: 13), or from a sequence sharing at least 60%, 70%, 75%, 80%, 90%, 95%, 96%, 97%, 98%, 99% of identity over amino acid residues 114 to 135, preferably from 115 to 135, more preferably from 116 to 135, more preferably from 117 to 135, more preferably from 118 to 135, more preferably from 119 to 135, more preferably from 120 to 135, even more preferably from 121 to 135 of human GPVI (SEQ ID NO: 13).

In one embodiment, said conformational epitope comprises at least one amino acid residue from amino acid residues 165 to 187, preferably from 166 to 186, more preferably from 167 to 185, more preferably from 168 to 184, even more preferably from 169 to 183 of human GPVI (SEQ ID NO: 13) or from a sequence sharing at least 60%, 70%, 75%, 80%, 90%, 95%, 96%, 97%, 98%, 99% of identity over amino acid residues 165 to 187, preferably from 166 to 186, more preferably from 167 to 185, more preferably from 168 to 184, even more preferably from 169 to 183 of human GPVI (SEQ ID NO: 13).

In one embodiment, said conformational epitope comprises at least 1, 2, 3, 4, 5, 6, 7, 8, 9, 10, 11, 12, 13, 14, 15, 16, 17, 18, 19, 20, 21, 22 amino acid residues from amino acid residues 165 to 187, preferably from 166 to 186, more preferably from 167 to 185, more preferably from 168 to 184, even more preferably from 169 to 183 of human GPVI (SEQ ID NO: 13) or from a sequence sharing at least 60%, 70%, 75%, 80%, 90%, 95%, 96%, 97%, 98%, 99% of identity over amino acid residues 165 to 187, preferably from 166 to 186, more preferably from 167 to 185, more preferably from 168 to 184, even more preferably from 169 to 183 of human GPVI (SEQ ID NO: 13).

In one embodiment, said conformational epitope comprises:
- at least one amino acid residue from amino acid residues 114 to 142, preferably from 115 to 141, more preferably from 116 to 140, more preferably from 117 to 139, more preferably from 118 to 138, more preferably from 119 to 137, more preferably from 120 to 136, even more preferably from 121 to 135 of human GPVI (SEQ ID NO: 13) or from a sequence sharing at least 60%, 70%, 75%, 80%, 90%, 95%, 96%, 97%, 98%, 99% of identity over amino acid residues 114 to 142, preferably from 115 to 141, more preferably from 116 to 140, more preferably from 117 to 139, more preferably from 118 to 138, more preferably from 119 to 137, more preferably from 120 to 136, even more preferably from 121 to 135 of human GPVI (SEQ ID NO: 13); and
- at least one amino acid residue from amino acid residues 165 to 187, preferably from 166 to 186, more preferably from 167 to 185, more preferably from 168 to 184, even more preferably from 169 to 183 of human GPVI (SEQ ID NO: 13) or from a sequence sharing at least 60%, 70%, 75%, 80%, 90%, 95%, 96%, 97%, 98%, 99% of identity over amino acid residues 165 to 187, preferably from 166 to 186, more preferably from 167 to 185, more preferably from 168 to 184, even more preferably from 169 to 183 of human GPVI (SEQ ID NO: 13).

In one embodiment, said conformational epitope comprises:
- at least 1, 2, 3, 4, 5, 6, 7, 8, 9, 10, 11, 12, 13, 14, 15, 16, 17, 18, 19, 20, 21, 22, 23, 24, 25, 26, 27, 28 amino acid residues from amino acid residues 114 to 142, preferably from 115 to 141, more preferably from 116 to 140, more preferably from 117 to 139, more preferably from 118 to 138, more preferably from 119 to 137, more preferably from 120 to 136, even more preferably from 121 to 135 of human GPVI (SEQ ID NO: 13) or from a sequence sharing at least 60%, 70%, 75%, 80%, 90%, 95%, 96%, 97%, 98%, 99% of identity over amino acid residues 114 to 142, preferably from 115 to 141, more preferably from 116 to 140, more preferably from 117 to 139, more preferably from 118 to 138, more preferably from 119 to 137, more preferably from 120 to 136, even more preferably from 121 to 135 of human GPVI (SEQ ID NO: 13); and
- at least 1, 2, 3, 4, 5, 6, 7, 8, 9, 10, 11, 12, 13, 14, 15, 16, 17, 18, 19, 20, 21, 22 amino acid residues from amino acid residues 165 to 187, preferably from 166 to 186, more preferably from 167 to 185, more preferably from 168 to 184, even more preferably from 169 to 183 of human GPVI (SEQ ID NO: 13) or from a sequence sharing at least 60%, 70%, 75%, 80%, 90%, 95%, 96%, 97%, 98%, 99% of identity over amino acid residues 165 to 187, preferably from 166 to 186, more preferably from 167 to 185, more preferably from 168 to 184, even more preferably from 169 to 183 of human GPVI (SEQ ID NO: 13).

In one embodiment, said conformational epitope comprises:
- at least one amino acid residue from amino acid residues 114 to 135, preferably from 115 to 135, more preferably from 116 to 135, more preferably from 117 to 135, more preferably from 118 to 135, more preferably from 119 to 135, more preferably from 120 to 135, even more preferably from 121 to 135 of human GPVI (SEQ ID NO: 13) or from a sequence sharing at least 60%, 70%, 75%, 80%, 90%, 95%, 96%, 97%, 98%, 99% of identity over amino acid residues 114 to 135, preferably from 115 to 135, more preferably from 116 to 135, more preferably from 117 to 135, more preferably from 118 to 135, more preferably from 119 to 135, more preferably from 120 to 135, even more preferably from 121 to 135 of human GPVI (SEQ ID NO: 13); and
- at least one amino acid residue from amino acid residues 165 to 187, preferably from 166 to 186, more preferably from 167 to 185, more preferably from 168 to 184, even more preferably from 169 to 183 of human GPVI (SEQ ID NO: 13) or from a sequence sharing at least 60%, 70%, 75%, 80%, 90%, 95%, 96%, 97%, 98%, 99% of identity over amino acid residues 165 to 187, preferably from 166 to 186, more preferably from 167 to 185, more preferably from 168 to 184, even more preferably from 169 to 183 of human GPVI (SEQ ID NO: 13).

In one embodiment, said conformational epitope comprises:
- at least 1, 2, 3, 4, 5, 6, 7, 8, 9, 10, 11, 12, 13, 14, 15, 16, 17, 18, 19, 20, 21 amino acid residues from amino acid residues 114 to 135, preferably from 115 to 135, more preferably from 116 to 135, more preferably from 117 to 135, more preferably from 118 to 135, more preferably from 119 to 135, more preferably from 120 to 135, even more preferably from 121 to 135 of human GPVI (SEQ ID NO: 13) or from a sequence sharing at least 60%, 70%, 75%, 80%, 90%, 95%, 96%, 97%, 98%, 99% of identity over amino acid residues 114 to 135, preferably from 115 to 135, more preferably from 116 to 135, more preferably from 117 to 135, more preferably from 118 to 135, more preferably from 119 to 135, more preferably from 120 to 135, even more preferably from 121 to 135 of human GPVI (SEQ ID NO: 13); and
- at least 1, 2, 3, 4, 5, 6, 7, 8, 9, 10, 11, 12, 13, 14, 15, 16, 17, 18, 19, 20, 21, 22 amino acid residues from amino acid residues 165 to 187, preferably from 166 to 186, more preferably from 167 to 185, more preferably from 168 to 184, even more preferably from 169 to 183 of human GPVI (SEQ ID NO: 13) or from a sequence sharing at least 60%, 70%, 75%, 80%, 90%, 95%, 96%, 97%, 98%, 99% of identity over amino acid residues 165 to 187, preferably from 166 to 186, more preferably from 167 to 185, more preferably from 168 to 184, even more preferably from 169 to 183 of human GPVI (SEQ ID NO: 13).

In one embodiment, said conformational epitope comprises at least one amino acid residue from amino acid residues 121 to 135 of human GPVI (SEQ ID NO: 13) or from a sequence sharing at least 60%, 70%, 75%, 80%, 90%, 95%, 96%, 97%, 98%, 99% of identity over amino acid residues 121 to 135 of human GPVI (SEQ ID NO: 13); and at least one amino acid residue from amino acid residues 169 to 183 of human GPVI (SEQ ID NO: 13) or from a sequence sharing at least 60%, 70%, 75%, 80%, 90%, 95%, 96%, 97%, 98%, 99% of identity over amino acid residues 169 to 183 of human GPVI (SEQ ID NO: 13).

Thus, in one embodiment, the protein of the invention binds to a conformational epitope comprising at least one amino acid residue from amino acid residues 121 to 135 of human GPVI (SEQ ID NO: 13) or from a sequence sharing at least 60%, 70%, 75%, 80%, 90%, 95%, 96%, 97%, 98%, 99% of identity over amino acid residues 121 to 135 of human GPVI (SEQ ID NO: 13); and at least one amino acid residue from amino acid residues 169 to 183 of human GPVI (SEQ ID NO: 13) or from a sequence sharing at least 60%, 70%, 75%, 80%, 90%, 95%, 96%, 97%, 98%, 99% of identity over amino acid residues 169 to 183 of human GPVI (SEQ ID NO: 13).

In one embodiment, said conformational epitope comprises at least one amino acid residue from amino acid residues 121 to 135 of human GPVI (SEQ ID NO: 13) or from a sequence sharing at least 60%, 70%, 75%, 80%, 90%, 95%, 96%, 97%, 98%, 99% of identity over amino acid residues 121 to 135 of human GPVI (SEQ ID NO: 13); and at least one amino acid residue from amino acid residues 169 to 180 of human GPVI (SEQ ID NO: 13) or from a sequence sharing at least 60%, 70%, 75%, 80%, 90%, 95%, 96%, 97%, 98%, 99% of identity over amino acid residues 169 to 180 of human GPVI (SEQ ID NO: 13).

Thus, in one embodiment, the protein of the invention binds to a conformational epitope comprising at least one amino acid residue from amino acid residues 121 to 135 of human GPVI (SEQ ID NO: 13) or from a sequence sharing at least 60%, 70%, 75%, 80%, 90%, 95%, 96%, 97%, 98%, 99% of identity over amino acid residues 121 to 135 of human GPVI (SEQ ID NO: 13); and at least one amino acid residue from amino acid residues 169 to 180 of human GPVI (SEQ ID NO: 13) or from a sequence sharing at least 60%, 70%, 75%, 80%, 90%, 95%, 96%, 97%, 98%, 99% of identity over amino acid residues 169 to 180 of human GPVI (SEQ ID NO: 13).

In one embodiment, said conformational epitope consists of:
amino acid residues 121 to 135 of human GPVI (SEQ ID NO: 13) or of a sequence sharing at least 60%, 70%, 75%, 80%, 90%, 95%, 96%, 97%, 98%, 99% of identity over amino acid residues 121 to 135 of human GPVI (SEQ ID NO: 13); and
amino acid residues 169 to 183 of human GPVI (SEQ ID NO: 13) or of a sequence sharing at least 60%, 70%, 75%, 80%, 90%, 95%, 96%, 97%, 98%, 99% of identity over amino acid residues 169 to 183 of human GPVI (SEQ ID NO: 13).

Thus, in one embodiment, the protein of the invention binds to a conformational epitope consisting of:
amino acid residues 121 to 135 of human GPVI (SEQ ID NO: 13) or of a sequence sharing at least 60%, 70%, 75%, 80%, 90%, 95%, 96%, 97%, 98%, 99% of identity over amino acid residues 121 to 135 of human GPVI (SEQ ID NO: 13); and
amino acid residues 169 to 183 of human GPVI (SEQ ID NO: 13) or of a sequence sharing at least 60%, 70%, 75%, 80%, 90%, 95%, 96%, 97%, 98%, 99% of identity over amino acid residues 169 to 183 of human GPVI (SEQ ID NO: 13).

In one embodiment, said conformational epitope consists of:
amino acid residues 121 to 135 of human GPVI (SEQ ID NO: 13) or of a sequence sharing at least 60%, 70%, 75%, 80%, 90%, 95%, 96%, 97%, 98%, 99% of identity over amino acid residues 121 to 135 of human GPVI (SEQ ID NO: 13); and
amino acid residues 169 to 180 of human GPVI (SEQ ID NO: 13) or of a sequence sharing at least 60%, 70%, 75%, 80%, 90%, 95%, 96%, 97%, 98%, 99% of identity over amino acid residues 169 to 180 of human GPVI (SEQ ID NO: 13).

Thus, in one embodiment, the protein of the invention binds to a conformational epitope consisting of:
amino acid residues 121 to 135 of human GPVI (SEQ ID NO: 13) or of a sequence sharing at least 60%, 70%, 75%, 80%, 90%, 95%, 96%, 97%, 98%, 99% of identity over amino acid residues 121 to 135 of human GPVI (SEQ ID NO: 13); and
amino acid residues 169 to 180 of human GPVI (SEQ ID NO: 13) or of a sequence sharing at least 60%, 70%, 75%, 80%, 90%, 95%, 96%, 97%, 98%, 99% of identity over amino acid residues 169 to 180 of human GPVI (SEQ ID NO: 13).

Another object of the invention is an isolated protein binding to human GPVI, wherein said protein has a $K_D$ for binding to human GPVI, preferably soluble human GPVI, less than or equal to 15 nM, preferably less than or equal to 10 nM and more preferably less than or equal to 5 nM.

In one embodiment, the isolated protein of the invention has a $k_{off}$ for binding to human GPVI of less than or equal to about $8 \cdot 10^{-4}$ sec$^{-1}$, preferably less than or equal to about $6 \cdot 10^{-4}$ sec$^{-1}$, and more preferably less than or equal to about $4 \cdot 10^{-4}$ sec$^{-1}$.

In one embodiment, the isolated protein of the invention has a $k_{on}$, for binding to human GPVI of at least about $5 \cdot 10^4$ M$^{-1}$sec$^{-1}$, preferably at least about $5.5 \cdot 10^4$ M$^{-1}$sec$^{-1}$, and more preferably at least about $5.9 \cdot 10^4$ M$^{-1}$sec$^{-1}$ and more preferably at least about $6 \cdot 10^{-4}$ sec$^{-1}$.

In one embodiment, the $K_D$ may be determined by Surface plasmon resonance (SPR, BIAcore), using immobilized soluble GPVI at a dose ranging from about 700 to about 1600 resonance units (RU) (corresponding to about 8.5 to about 11.3 fmol/mm$^2$), preferably from about 850 to about 1200 RU, more preferably from about 950 to about 1075 RU and/or using PBS pH 7.4 as running buffer, and/or using BIAevaluation version 3.0 software for analyzing data. In one embodiment, soluble GPVI corresponds to the extracellular domain of GPVI fused at its C-terminus via a linker (such as, for example, via a Gly-Gly-Arg linker) to a hFc sequence. This soluble GPVI may be referred to as soluble GPVI-Fc.

A method for determining the affinity of the protein of the invention for soluble GPVI is shown below:

Binding of the protein of the invention to soluble human GPVI is analyzed with surface plasmon resonance using a BIAcore 2000 system (Uppsala, Sweden).

Soluble GPVI-Fc is immobilized at a dose ranging from about 700 to about 1600 RU (corresponding to about 8.5 to about 11.3 fmol/mm$^2$), preferably from about 850 to about 1200 RU, more preferably from about 950 to about 1075 RU, and even more preferably from about 960 to about 1071 RU onto a Carboxy-Methyl Dextran CMS sensor chip using the amine coupling method (Wizard procedure). The protein is then passed over the immobilized GPVI-Fc in PBS pH 7.4 (10 mM phosphate, 138 mM NaCl, 2.7 mM KCl, pH 7.42 at 25.4° C.) at a flow rate of 20 μL/min at 25° C. Kinetic constants ($k_{on}$, $k_{off}$) and affinity are determined using BIAevaluation version 3.0 software, by fitting data to binding model. PBS pH 7.4 is the running buffer.

In an embodiment, said protein is an antibody molecule selected from the group consisting of a whole antibody, a humanized antibody, a single chain antibody, a dimeric single chain antibody, a Fv, a Fab, a F(ab)'2, a defucosylated antibody, a bi-specific antibody, a diabody, a triabody and a tetrabody.

In another embodiment, said protein is an antibody fragment selected from the group consisting of a unibody, a domain antibody, and a nanobody.

In another embodiment, said protein is an antibody mimetic selected from the group consisting of an affibody, an affilin, an affitin, an adnectin, an atrimer, an evasin, a DARPin, an anticalin, an avimer, a fynomer, a versabody and a duocalin.

A domain antibody is well known in the art and refers to the smallest functional binding units of antibodies, corresponding to the variable regions of either the heavy or light chains of antibodies.

A nanobody is well known in the art and refers to an antibody-derived therapeutic protein that contains the unique structural and functional properties of naturally-occurring heavy chain antibodies. These heavy chain antibodies may contain a single variable domain (VHH) and two constant domains (CH2 and CH3).

A unibody is well known in the art and refers to an antibody fragment lacking the hinge region of IgG4 antibodies. The deletion of the hinge region results in a molecule that is essentially half the size of traditional IgG4 antibodies and has a univalent binding region rather than the bivalent biding region of IgG4 antibodies.

An affibody is well known in the art and refers to affinity proteins based on a 58 amino acid residue protein domain, derived from one of the IgG binding domain of staphylococcal protein A.

DARPins (Designed Ankyrin Repeat Proteins) are well known in the art and refer to an antibody mimetic DRP (designed repeat protein) technology developed to exploit the binding abilities of non-antibody proteins.

Anticalins are well known in the art and refer to another antibody mimetic technology, wherein the binding specificity is derived from lipocalins. Anticalins may also be formatted as dual targeting protein, called Duocalins.

Avimers are well known in the art and refer to another antibody mimetic technology.

Versabodies are well known in the art and refer to another antibody mimetic technology. They are small proteins of 3-5 kDa with >15% cysteines, which form a high disulfide density scaffold, replacing the hydrophobic core the typical proteins have.

In one embodiment, the protein of the invention is monovalent, and is preferably selected from a whole monovalent antibody, a humanized monovalent antibody, a single chain antibody, a Fv, a Fab, or an antibody fragment selected from the group consisting of a unibody, a domain antibody, and a nanobody; or a monomeric antibody mimetic selected from the group consisting of an affibody, an affilin, an affitin, an adnectin, an atrimer, an evasin, a DARPin, an anticalin, an avimer, a fynomer, and a versabody.

In another embodiment, said protein is an immunoconjugate comprising an antibody or fragment thereof conjugated to a therapeutic agent.

In another embodiment, said protein is a conjugate comprising the protein of the invention conjugated to an imaging agent. Said protein could be used for example for imaging applications.

In an embodiment, said protein is a monoclonal antibody.

In another embodiment, said protein is a polyclonal antibody.

Another object of the invention is an anti-hGPVI antibody or antigen binding fragment thereof wherein the variable region of the heavy chain comprises at least one of the followings CDRs:

```
VH-CDR1:
                                      (SEQ ID NO: 1)
GYTFTSYNMH;

VH-CDR2:
                                      (SEQ ID NO: 2)
GIYPGNGDTSYNQKFQG;
and

VH-CDR3:
                                      (SEQ ID NO: 3)
GTVVGDWYFDV.
```

CDR numbering and definition are according to the Kabat/Chothia definition.

Another object of the invention is an anti-hGPVI antibody or antigen binding fragment thereof wherein the variable region of the light chain comprises at least one of the followings CDRs:

```
VL-CDR1:
                                      (SEQ ID NO: 4)
RSSQSLENSNGNTYLN;

VL-CDR2:
                                      (SEQ ID NO: 5)
RVSNRFS;
and

VL-CDR3:
                                      (SEQ ID NO: 6)
LQLTHVPWT.
```

CDR numbering and definition are according to the Kabat/Chothia definition.

In one embodiment, the anti-hGPVI antibody or antigen binding fragment thereof of the invention comprises:
  in the heavy chain, at least one of the following CDR: GYTFTSYNMH (SEQ ID NO: 1), GIYPGNGDTSYNQKFQG (SEQ ID NO: 2) and GTVVGDWYFDV (SEQ ID NO: 3), and/or
  in the light chain, at least one of the following CDR: RSSQSLENSNGNTYLN (SEQ ID NO: 4), RVSNRFS (SEQ ID NO: 5), and LQLTHVPWT (SEQ ID NO: 6).

In another embodiment of the invention, the anti-hGPVI antibody or antigen binding fragment thereof comprises in its heavy chain the 3 CDRs SEQ ID NO: 1, SEQ ID NO: 2 and SEQ ID NO: 3.

In another embodiment of the invention, the anti-hGPVI antibody or antigen binding fragment thereof comprises in its light chain the 3 CDRs SEQ ID NO: 4, SEQ ID NO: 5 and SEQ ID NO: 6.

In another embodiment of the invention, the anti-hGPVI antibody or antigen binding fragment thereof comprises in its heavy chain the 3 CDRs SEQ ID NO: 1, SEQ ID NO: 2 and SEQ ID NO: 3, and in its light chain the 3 CDRs SEQ ID NO: 4, SEQ ID NO: 5 and SEQ ID NO: 6.

In another embodiment of the invention, the anti-hGPVI antibody or antigen binding fragment thereof comprises in its heavy chain the 3 CDRs SEQ ID NO: 1, SEQ ID NO: 2 and SEQ ID NO: 3, and in its light chain the 3 CDRs SEQ ID NO: 4, SEQ ID NO: 5 and SEQ ID NO: 6, optionally wherein one, two, three or more of the amino acids in any of said sequences may be substituted by a different amino acid.

According to the invention, any of the CDRs 1, 2 and 3 of the heavy and light chains may be characterized as having an amino acid sequence that shares at least 60%, 70%, 75%, 80%, 90%, 95%, 96%, 97%, 98%, 99% of identity with the particular CDR or sets of CDRs listed in the corresponding SEQ ID NO.

In another embodiment of the invention, the anti-hGPVI antibody or antigen binding fragment thereof is selected from the group consisting of an antibody having:
  (i) the heavy chain CDR 1, 2 and 3 (VH-CDR1, VH-CDR2, VH-CDR3) amino acid sequences as shown in SEQ ID NO: 1, 2 and 3 respectively; and
  (ii) the light chain CDR 1, 2 and 3 (VL-CDR1, VL-CDR2, VL-CDR3) amino acid sequences as shown in SEQ ID NO: 4, 5 and 6 respectively;
optionally wherein one, two, three or more of the amino acids in any of said sequences may be substituted by a different amino acid.

In one embodiment, the anti-GPVI antibody or antigen binding fragment thereof of the invention comprises a heavy chain variable region comprising or consisting of the sequence SEQ ID NO: 7.

```
                                               (SEQ ID NO: 7)
QVQLVQSGAEVKKPGASVKVSCKASGYTFTSYNMHWVRQAPGQGLEWMGG

IYPGNGDTSYNQKFQGRVTMTRDTSTSTVYMELSSLRSEDTAVYYCARGT

VVGDWYFDVWGQGTLVTVSS
```

In one embodiment, the anti-GPVI antibody or antigen binding fragment thereof of the invention comprises a light chain variable region comprising or consisting of the sequence SEQ ID NO: 8.

```
                                               (SEQ ID NO: 8)
DIQMTQSPSSLSASVGDRVTITCRSSQSLENSNGNTYLNWYQQKPGKAPK

LLIYRVSNRFSGVPSRFSGSGSGTDFTFTISSLQPEDIATYYCLQLTHVP

WTFGQGTKVEITR
```

In one embodiment, the anti-GPVI antibody or antigen binding fragment thereof of the invention comprises a light chain variable region comprising or consisting of the sequence SEQ ID NO: 9.

```
                                               (SEQ ID NO: 9)
DIQMTQSPSSLSASVGDRVTITCSASQSLENSNGNTYLNWYQQKPGKAPK

LLIYRVSNRFSGVPSRFSGSGSGTDFTLTISSLQPEDFATYYCLQLTHVP

WTFGQGTKVEIKR
```

In another embodiment of the invention, the anti-GPVI antibody (ACT017 antibody) or antigen binding fragment thereof comprises a heavy chain variable region comprising or consisting of the sequence SEQ ID NO: 7 and the light chain variable region comprising or consisting of the sequence SEQ ID NO: 8.

In another embodiment of the invention, the anti-GPVI antibody (ACT006 antibody) or antigen binding fragment thereof comprises the heavy chain variable region comprising or consisting of the sequence SEQ ID NO: 7 and the light chain variable region comprising or consisting of the sequence SEQ ID NO: 9.

According to the invention, one, two, three or more of the amino acids of the heavy chain or light chain variable regions as described hereinabove may be substituted by a different amino acid.

In another embodiment, an antibody of the invention comprises heavy and light chain variable regions comprising amino acid sequences that are homologous to the amino acid sequences of the ACT017 antibody described herein, and wherein the antibodies retain the desired functional properties of the protein of the invention.

In another embodiment, an antibody of the invention comprises heavy and light chain variable regions comprising amino acid sequences that are homologous to the amino acid sequences of the ACT006 antibody described herein, and wherein the antibodies retain the desired functional properties of the protein of the invention.

According to the invention, the heavy chain variable region encompasses sequences that have 60%, 70%, 75%, 80%, 90%, 95%, 96%, 97%, 98%, 99% or more of identity with SEQ ID NO: 7.

According to the invention, the light chain variable region encompasses sequences that have 60%, 70%, 75%, 80%, 90%, 95%, 96%, 97%, 98%, 99% or more of identity with SEQ ID NO: 8 or SEQ ID NO: 9.

In any of the antibodies of the invention, e.g. ACT017 or ACT006, the specified variable region and CDR sequences may comprise conservative sequence modifications. Conservative sequence modifications refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are typically those in which an amino acid residue is replaced with an amino acid residue having a side chain with similar physicochemical properties. Specified variable region and CDR sequences may comprise one, two, three, four or more amino acid insertions, deletions or substitutions. Where substitutions are made, preferred substitutions will be conservative modifications. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g. threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the properties set forth herein) using the assays described herein.

In one embodiment, the invention also provides an antibody that binds essentially the same epitope as ACT017 or ACT006 antibodies. In the present invention, an antibody that binds essentially the same epitope as ACT017 or ACT006 antibodies will be referred as an ACT017-like or ACT006-like antibody, respectively.

In some embodiments of this invention, anti-hGPVI antibodies comprising VH and VL domains, or CDRs thereof may comprise CH1 domains and/or CL domains, the amino acid sequence of which is fully or substantially human. Where the antigen binding protein of the invention is an antibody intended for human therapeutic use, it is typical for the entire constant region of the antibody, or at least a part thereof, to have a fully or substantially human amino acid sequence. Therefore, one or more or any combination of the CH1 domain, hinge region, CH2 domain, CH3 domain and CL domain (and CH4 domain if present) may be fully or substantially human with respect to its amino acid sequence. Advantageously, the CH1 domain, hinge region, CH2 domain, CH3 domain and CL domain (and CH4 domain if present) may all have a fully or substantially human amino acid sequence. In the context of the constant region of a humanized or chimeric antibody, or an antibody fragment, the term "substantially human" refers to an amino acid sequence identity of at least 70%, or at least 80%, or at least 90%, or at least 95%, or at least 97%, or at least 99% with a human constant region. The term "human amino acid sequence" in this context refers to an amino acid sequence which is encoded by a human immunoglobulin gene, which includes germline, rearranged and somatically mutated genes. The invention also contemplates proteins comprising constant domains of "human" sequence which have been altered, by one or more amino acid additions, deletions or substitutions with respect to the human sequence, excepting those embodiments where the presence of a "fully human" hinge region is expressly required. The presence of a "fully human" hinge region in the anti-hGPVI antibodies of the invention may be beneficial both to minimize immunogenicity and to optimize stability of the antibody. It is considered that one or more amino acid substitutions, insertions or deletions may be made within the constant region of the heavy and/or the light chain, particularly within the Fc region. Amino acid substitutions may result in replacement of the substituted amino acid with a different naturally occurring amino acid, or with a non-natural or modified amino acid. Other structural modifications are also permitted, such as for example changes in glycosylation pattern (e.g. by addition or deletion of N- or O-linked glycosylation sites). Depending on the intended use of the antibody, it may be desirable to modify the antibody of the invention with respect to its binding properties to Fc receptors, for example to modulate effector function. For example cysteine residue(s) may be introduced in the Fc region, thereby allowing interchain disulfide bond formation in this region. The homodimeric antibody thus generated may have improved effector function. See Caron et al., J. Exp. Med. 176: 1191-1195 (1992) and Shopes, B. J. Immunol. 148:2918-2922 (1992).

Another object of the invention is an isolated nucleic sequence encoding the heavy chain variable region of sequence SEQ ID NO: 7. Preferably, said nucleic sequence is SEQ ID NO: 10:

```
                                              (SEQ ID NO: 10)
CAGGTTCAGCTGGTTCAGTCAGGGGCTGAGGTGAAGAAGCCTGGAGCCTC

AGTGAAGGTGTCCTGCAAGGCTTCTGGCTACACATTTACCAGTTACAATA

TGCACTGGGTAAGACAGGCTCCTGGACAGGGCCTGGAATGGATGGGAGGT

ATTTATCCAGGAAATGGTGATACTTCCTACAATCAGAAGTTCCAGGGCCG

AGTTACTATGACTCGGGACACTTCCACCTCTACAGTGTACATGGAGCTCA

GCAGCCTGAGATCTGAGGACACCGCGGTCTATTACTGTGCAAGAGGCACC

GTGGTCGGCGACTGGTACTTCGATGTGTGGGGCCAAGGCACCCTGGTCAC

CGTGAGCAGT
```

Another object of the invention is an isolated nucleic sequence encoding the light chain variable region of sequence SEQ ID NO: 8. Preferably, said nucleic sequence is SEQ ID NO: 11:

```
                                              (SEQ ID NO: 11)
GACATCCAGATGACCCAGAGCCCAAGCAGCCTGAGCGCCAGCGTGGGTGA

CAGAGTGACCATCACCTGTAGAAGTAGTCAGAGCCTTGAGAACAGCAACG

GAAACACCTACCTGAATTGGTACCAGCAGAAGCCAGGTAAGGCTCCAAAG

CTGCTGATCTACAGAGTTTCCAACCGATTCTCTGGTGTGCCAAGCAGATT

CAGCGGTAGCGGTAGCGGTACCGACTTCACCTTCACCATCAGCAGCCTCC

AGCCAGAGGACATCGCCACCTACTACTGCCTCCAGCTGACTCATGTCCCA

TGGACCTTCGGTCAGGGCACCAAGGTGGAGATCACCCGG
```

Another object of the invention is an isolated nucleic sequence encoding the light chain variable region of sequence SEQ ID NO: 9. Preferably, said nucleic sequence is SEQ ID NO: 12

```
                                              (SEQ ID NO: 12)
GACATCCAGATGACCCAGAGCCCAAGCAGCCTGAGCGCCAGCGTGGGTGA

CAGAGTGACCATCACCTGTAGTGCCAGTCAGAGCCTTGAGAACAGCAACG

GAAACACCTACCTGAATTGGTACCAGCAGAAGCCAGGTAAGGCTCCAAAG

CTGCTGATCTACAGAGTTTCCAACCGATTCTCTGGTGTGCCAAGCAGATT

CAGCGGTAGCGGTAGCGGTACCGACTTCACCCTCACCATCAGCAGCCTCC

AGCCAGAGGACTTCGCCACCTACTACTGCCTCCAGCTGACTCATGTCCCA

TGGACCTTCGGTCAGGGCACCAAGGTGGAGATCAAACGC
```

Another object of the invention is an expression vector comprising the nucleic sequences encoding the anti-GPVI antibody of the invention. In one embodiment, the expression vector of the invention comprises at least one of SEQ ID NO: 10, SEQ ID NO: 11 and SEQ ID NO: 12 or any sequence having a nucleic acid sequence that shares at least 60%, 70%, 75%, 80%, 90%, 95%, 96%, 97%, 98%, 99% of identity with said SEQ ID NO: 10-12.

In one embodiment, the vector of the invention comprises the sequence SEQ ID NO: 10 and a sequence encoding a constant region of a heavy chain. A non-limiting example of a sequence encoding a constant region of a heavy chain is SEQ ID NO: 14.

(SEQ ID NO: 14)
GCCTCCACCAAGGGTCCCTCAGTCTTCCCACTGGCACCCTCCTCCAAGAG

CACCTCTGGTGGCACAGCTGCCCTGGGCTGCCTGGTCAAGGACTACTTCC

CAGAACCAGTGACTGTGTCATGGAACTCAGGCGCCCTGACCAGCGGCGTG

CACACCTTCCCTGCTGTCTTGCAGTCCTCAGGACTCTACTCCCTCAGCAG

CGTGGTGACCGTGCCCTCCAGCAGCTTGGGCACCCAGACCTACATCTGCA

ACGTGAATCACAAGCCCAGCAACACCAAGGTGGACAAGAAAGTCGAGCCT

AAGTCATGCGACAAGACTCAC

In one embodiment, the vector of the invention comprises the sequence SEQ ID NO: 11 or SEQ ID NO: 12 and a sequence encoding a constant region of a light chain. A non-limiting example of a sequence encoding a constant region of a light chain is SEQ ID NO: 15.

(SEQ ID NO: 15)
ACTGTGGCTGCACCAAGTGTGTTCATCTTCCCACCTAGCGATGAGCAGTT

GAAATCTGGAACTGCCTCTGTCGTGTGCCTCCTGAACAACTTCTACCCAC

GGGAGGCCAAGGTACAGTGGAAGGTGGATAACGCCCTCCAATCCGGTAAC

TCCCAGGAGAGTGTCACAGAGCAAGATAGCAAGGACAGCACCTACAGCCT

CAGCAGCACCCTGACTCTGAGCAAAGCAGACTACGAGAAGCACAAGGTCT

ACGCCTGCGAAGTCACCCATCAGGGCCTGAGTTCCCCTGTCACAAAGAGC

TTCAACCGGGGAGAGTGT

In one embodiment, the vector of the invention comprises a sequence encoding a signal peptide. Non-limiting examples of signal peptides sequences include, but are not limited to, SEQ ID NO: 16 and SEQ ID NO: 17.

(SEQ ID NO: 16)
ATGGATATGCGTGTACCAGCTCAACTACTTGGACTTCTATTGCTTTGGCT

TCGTGGTGCTAGATGT (SEQ ID NO: 17)
ATGGACTGGACTTGGAGAATCCTATTCTTGGTTGCTGCAGCTACAGGTGC

TCATTCA

In one embodiment, the vector of the invention comprises SEQ ID NO: 10, and a sequence encoding a constant region of a heavy chain (such as, for example, SEQ ID NO: 14), and a signal peptide sequence. An example of such a vector is a vector comprising SEQ ID NO: 18. SEQ ID NO: 18 further comprises cloning sites.

(SEQ ID NO: 18)
GCGGCCGCCACCATGGACTGGACTTGGAGAATCCTATTCTTGGTTGCTGC

AGCTACAGGTGCTCATTCACAGGTTCAGCTGGTTCAGTCAGGGGCTGAGG

TGAAGAAGCCTGGAGCCTCAGTGAAGGTGTCCTGCAAGGCTTCTGGCTAC

ACATTTACCAGTTACAATATGCACTGGGTAAGACAGGCTCCTGGACAGGG

CCTGGAATGGATGGGAGGTATTTATCCAGGAAATGGTGATACTTCCTACA

ATCAGAAGTTCCAGGGCCGAGTTACTATGACTCGGGACACTTCCACCTCT

ACAGTGTACATGGAGCTCAGCAGCCTGAGATCTGAGGACACCGCGGTCTA

TTACTGTGCAAGAGGCACCGTGGTCGGCGACTGGTACTTCGATGTGTGGG

GCCAAGGCACCCTGGTCACCGTGAGCAGTGCCTCCACCAAGGGTCCCTCA

GTCTTCCCACTGGCACCCTCCTCCAAGAGCACCTCTGGTGGCACAGCTGC

CCTGGGCTGCCTGGTCAAGGACTACTTCCCAGAACCAGTGACTGTGTCAT

GGAACTCAGGCGCCCTGACCAGCGGCGTGCACACCTTCCCTGCTGTCTTG

CAGTCCTCAGGACTCTACTCCCTCAGCAGCGTGGTGACCGTGCCCTCCAG

CAGCTTGGGCACCCAGACCTACATCTGCAACGTGAATCACAAGCCCAGCA

ACACCAAGGTGGACAAGAAAGTCGAGCCTAAGTCATGCGACAAGACTCAC

TGATGAGGATCC

In one embodiment, the vector of the invention comprises SEQ ID NO: 8, and a sequence encoding a constant region of a light chain (such as, for example, SEQ ID NO: 15), and a signal peptide sequence. An example of such a vector is a vector comprising SEQ ID NO: 19. SEQ ID NO: 19 further comprises cloning sites.

(SEQ ID NO: 19)
GACGTCACCATGGATATGCGTGTACCAGCTCAACTACTTGGACTTCTATT

GCTTTGGCTTCGTGGTGCTAGATGTGACATCCAGATGACCCAGAGCCCAA

GCAGCCTGAGCGCCAGCGTGGGTGACAGAGTGACCATCACCTGTAGAAGT

AGTCAGAGCCTTGAGAACAGCAACGGAAACACCTACCTGAATTGGTACCA

GCAGAAGCCAGGTAAGGCTCCAAAGCTGCTGATCTACAGAGTTTCCAACC

GATTCTCTGGTGTGCCAAGCAGATTCAGCGGTAGCGGTAGCGGTACCGAC

TTCACCTTCACCATCAGCAGCCTCCAGCCAGAGGACATCGCCACCTACTA

CTGCCTCCAGCTGACTCATGTCCCATGGACCTTCGGTCAGGGCACCAAGG

TGGAGATCACCCGGACTGTGGCTGCACCAAGTGTGTTCATCTTCCCACCT

AGCGATGAGCAGTTGAAATCTGGAACTGCCTCTGTCGTGTGCCTCCTGAA

CAACTTCTACCCACGGGAGGCCAAGGTACAGTGGAAGGTGGATAACGCCC

TCCAATCCGGTAACTCCCAGGAGAGTGTCACAGAGCAAGATAGCAAGGAC

AGCACCTACAGCCTCAGCAGCACCCTGACTCTGAGCAAAGCAGACTACGA

GAAGCACAAGGTCTACGCCTGCGAAGTCACCCATCAGGGCCTGAGTTCCC

CTGTCACAAAGAGCTTCAACCGGGGAGAGTGTTGATGATATC

In one embodiment, the vector of the invention comprises SEQ ID NO: 9, and a sequence encoding a constant region of a light chain (such as, for example, SEQ ID NO: 15), and a signal peptide sequence. An example of such a vector is a vector comprising SEQ ID NO: 20. SEQ ID NO: 20 further comprises cloning sites.

(SEQ ID NO: 20)
GACGTCACCATGGATATGCGTGTACCAGCTCAACTACTTGGACTTCTATT

GCTTTGGCTTCGTGGTGCTAGATGTGACATCCAGATGACCCAGAGCCCAA

GCAGCCTGAGCGCCAGCGTGGGTGACAGAGTGACCATCACCTGTAGTGCC

AGTCAGAGCCTTGAGAACAGCAACGGAAACACCTACCTGAATTGGTACCA

GCAGAAGCCAGGTAAGGCTCCAAAGCTGCTGATCTACAGAGTTTCCAACC

GATTCTCTGGTGTGCCAAGCAGATTCAGCGGTAGCGGTAGCGGTACCGAC

-continued
TTCACCCTCACCATCAGCAGCCTCCAGCCAGAGGACTTCGCCACCTACTA

CTGCCTCCAGCTGACTCATGTCCCATGGACCTTCGGTCAGGGCACCAAGG

TGGAGATCAAACGCACTGTGGCTGCACCAAGTGTGTTCATCTTCCCACCT

AGCGATGAGCAGTTGAAATCTGGAACTGCCTCTGTCGTGTGCCTCCTGAA

CAACTTCTACCCACGGGAGGCCAAGGTACAGTGGAAGGTGGATAACGCCC

TCCAATCCGGTAACTCCCAGGAGAGTGTCACAGAGCAAGATAGCAAGGAC

AGCACCTACAGCCTCAGCAGCACCCTGACTCTGAGCAAAGCAGACTACGA

GAAGCACAAGGTCTACGCCTGCGAAGTCACCCATCAGGGCCTGAGTTCCC

CTGTCACAAAGAGCTTCAACCGGGGAGAGTGTTGATGATATC

Another object of the invention is an isolated host cell comprising said vector. Said host cell may be used for the recombinant production of the antibodies of the invention. In an embodiment, host cells may be prokaryote, yeast, or eukaryote cells preferably mammalian cells, such as, for example: monkey kidney CV1 line transformed by SV40 (COS-7, ATCC CRL 1651); human embryonic kidney line (293 or 293 cells subcloned for growth in suspension culture, Graham et al., J. Gen. Virol. 36:59 (1977)); baby hamster kidney cells (BHK, ATCC CCL 10); Chinese hamster ovary cells/–DHFR (CHO, Urlaub et al., Proc. Natl. Acad. Sci. USA 77:4216 (1980)); mouse Sertoli cells (TM4, Mather, Biol. Reprod. 23:243-251 (1980)); mouse myeloma cells SP2/0-AG14 (ATCC CRL 1581; ATCC CRL 8287) or NSO (HPA culture collections no. 85110503); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2), as well as DSM's PERC-6 cell line. Expression vectors suitable for use in each of these host cells are also generally known in the art. It should be noted that the term "host cell" generally refers to a cultured cell line. Whole human beings into which an expression vector encoding an antigen binding protein according to the invention has been introduced are explicitly excluded from the definition of a "host cell".

Another objet of the invention is a method of producing an anti-hGPVI antibody or antigen binding fragment thereof which comprises culturing host cells containing the isolated polynucleotide sequence encoding the anti-hGPVI antibody under conditions suitable for expression of the anti-hGPVI antibody, and recovering the expressed anti-hGPVI antibody. This recombinant process can be used for large scale production of anti-hGPVI antibodies according to the invention, including monoclonal antibodies intended for in vitro, ex vivo, in vivo therapeutic, diagnostic uses. These processes are available in the art and will be known by the skilled person.

In one embodiment, the protein of the invention may be purified by chromatography, preferably by affinity chromatography, more preferably by affinity chromatography on protein L agarose.

Therefore, in one embodiment, the protein of the invention comprises a domain for binding protein L (PpL). Methods for transferring PpL-binding activity onto proteins of the invention are described in Muzard et al., Analytical Biochemistry 388, 331-338, 2009 and in Lakhrif et al., MAbs. 2016; 8(2):379-88, which are incorporated herein by reference.

Fragments and derivatives of antibodies of this invention (which are encompassed by the term "antibody" or "antibodies" as used in this application, unless otherwise stated or clearly contradicted by context), preferably a ACT017-like or ACT006-like antibody, can be produced by techniques that are known in the art. "Fragments" comprise a portion of the intact antibody, generally the antigen binding site or variable region. Examples of antibody fragments include Fab, Fab', Fab'-SH, F (ab')2, and Fv fragments; diabodies; any antibody fragment that is a protein having a primary structure consisting of one uninterrupted sequence of contiguous amino acid residues (referred to herein as a "single-chain antibody fragment" or "single chain protein"), including without limitation (1) single-chain Fv molecules (2) single chain proteins containing only one light chain variable domain, or a fragment thereof that contains the three CDRs of the light chain variable domain, without an associated heavy chain moiety and (3) single chain proteins containing only one heavy chain variable region, or a fragment thereof containing the three CDRs of the heavy chain variable region, without an associated light chain moiety; and multispecific antibodies formed from antibody fragments. Fragments of the present antibodies can be obtained using standard methods. For instance, Fab or F(ab')2 fragments may be produced by protease digestion of the isolated antibodies, according to conventional techniques. It will be appreciated that immunoreactive fragments can be modified using known methods, for example to slow clearance in vivo and obtain a more desirable pharmacokinetic profile the fragment may be modified with polyethylene glycol (PEG). Methods for coupling and site-specifically conjugating PEG to a Fab' fragment are described in, for example, Leong et al., Cytokines 16 (3): 106-119 (2001) and Delgado et al., Br. J. Cancer 73 (2): 175-182 (1996), the disclosures of which are incorporated herein by reference.

Alternatively, the DNA encoding an antibody of the invention, preferably an ACT017-like or ACT006-like antibody, may be modified so as to encode a fragment of the invention. The modified DNA is then inserted into an expression vector and used to transform or transfect an appropriate cell, which then expresses the desired fragment.

An object of the invention is a composition comprising at least one of the protein of the invention as described here above.

Another object of the invention is a pharmaceutical composition comprising at least one of the protein of the invention as described here above and at least one pharmaceutically acceptable excipient.

Pharmaceutically acceptable excipients that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (for example sodium carboxymethylcellulose), polyethylene glycol, polyacrylates, waxes, polyethylene-polyoxypropylene-block polymers, polyethylene glycol and wool fat.

Another object of the invention is a medicament comprising at least one of the protein of the invention as described here above.

In an embodiment, said protein is an anti-hGPVI antibody or antigen binding fragment thereof that inhibits GPVI signaling and/or signaling of a ligand of GPVI. As used herein, the term "inhibit" means that the protein is capable of blocking, reducing, preventing or neutralizing GPVI interaction with its ligands, GPVI signaling and/or the activation of molecules from the GPVI signaling pathway.

Examples of ligands of GPVI include, but are not limited to, collagen, fibrin, fibronectin, vitronectin and laminins.

In an embodiment, said protein is a neutralizing anti-hGPVI antibody.

In an embodiment, said protein inhibits the binding of GPVI to a ligand thereof (such as, for example, collagen, fibrin or any other GPVI ligand capable of inducing downstream signaling and platelet activation).

In an embodiment, said protein inhibits and/or prevents platelet aggregation in response to a ligand of GPVI, such as, for example, collagen. In an embodiment, said protein inhibits and/or prevents platelet adhesion to a ligand of GPVI, such as, for example, collagen.

In an embodiment, said protein inhibits and/or prevents GPVI-dependent thrombin production in response to a ligand of GPVI, such as, for example, fibrin. In an embodiment, said protein inhibits and/or prevent platelet-catalyzed thrombin production in response to collagen and/or to tissue factor.

In an embodiment, said protein inhibits and/or prevents platelet recruitment by a ligand of GPVI (such as, for example, fibrin) via GPVI.

In one embodiment, the protein of the invention induces saturation of platelets in whole blood or in platelet rich plasma when present at a concentration ranging from about 0.1 to about 10 µg/mL, preferably from about 0.5 to about 5 µg/mL, and more preferably from about 1 to about 2 µg/mL (corresponding to about 2 to about 200 nM, preferably from about 10 to about 100 nM, and more preferably from about 20 to about 40 nM).

In one embodiment, the protein of the invention inhibits collagen-induced platelet aggregation when used at a concentration of at least about 15 µg/mL, preferably of at least about 10 µg/mL, and more preferably of at least about 5 µg/mL. Preferably, the protein of the invention fully inhibits collagen-induced platelet aggregation when used at such concentrations.

In one embodiment, the IC50 of the protein of the invention for inhibiting collagen-induced platelet aggregation ranges from about 0.5 to about 10 µg/mL, preferably from about 1 to about 6 µg/mL, more preferably from about 2 to about 3.2 µg/mL.

In one embodiment, the concentration of the protein of the invention reducing by 50% the velocity of collagen-induced platelet aggregation ranges from about 0.5 to about 5 µg/mL, preferably from about 1 to about 3 µg/mL, more preferably of about 2 µg/mL.

In one embodiment, the concentration of the protein of the invention reducing the intensity of collagen-induced platelet aggregation ranges from about 0.5 to about 10 µg/mL, preferably from about 1 to about 6 µg/mL, more preferably of about 3.2 µg/mL.

In one embodiment, the protein of the invention does not induce depletion of GPVI when administered in vivo, such as, for example, when administered at a dose ranging from 0.01 to 500 mg.

In one embodiment, the protein of the invention does not induce a decrease in platelet count, i.e., thrombocytopenia, when administered in vivo, such as, for example, when administered at a dose ranging from 0.01 to 500 mg.

The present invention also relates to a protein, a composition, pharmaceutical composition or medicament as described hereinabove for treating or for use in treating a disease, disorder or condition related to GPVI.

In another embodiment, the protein, composition, pharmaceutical composition or medicament as described hereinabove is used to modulate leukocyte-platelet and platelet-endothelium interactions in inflammation and/or thrombosis. Therefore, according to an embodiment, the protein, composition, pharmaceutical composition or medicament as described hereinabove is used to treat inflammation and/or thrombosis.

In another embodiment, the protein, composition, pharmaceutical composition or medicament as described hereinabove is used to modulate, preferably to prevent, platelet aggregation and degranulation.

In another embodiment, the protein, composition, pharmaceutical composition or medicament as described hereinabove is used to treat disorders associated with abnormal or aberrant megakaryocyte and/or platelet proliferation, differentiation, morphology, migration, aggregation, degranulation and/or function. Examples of these disorders include, but are not limited to, bleeding disorders (such as, for example, bleeding tendency and/or prolonged bleeding time) such as thrombocytopenia such as, for example, idiopathic thrombocytopenic purpura (ITP) or immune thrombocytopenia.

In another embodiment, the protein, composition, pharmaceutical composition or medicament as described hereinabove is used to treat thrombotic disorders (such as, for example, thrombotic occlusion of coronary arteries), hemorrhagic disorders, diseases exhibiting quantitative or qualitative platelet dysfunction and diseases displaying endothelial dysfunction. These diseases include, but are not limited to, coronary artery and cerebral artery diseases.

In another embodiment, the protein, composition, pharmaceutical composition or medicament as described hereinabove is used to treat cerebral vascular diseases, including stroke and ischemia, venous thromboembolism diseases (such as, for example, diseases involving leg swelling, pain and ulceration, pulmonary embolism, abdominal venous thrombosis), thrombotic microangiopathies, vascular purpura.

In another embodiment, the protein, composition, pharmaceutical composition or medicament as described hereinabove is used to treat symptoms associated with platelet disorders and/or diseases (such as, for example, bleeding disorders). In particular, the protein, composition, pharmaceutical composition or medicament as described hereinabove can be used to modulate symptoms associated with ITP such as purpura and severe bleeding problems.

In another embodiment, the protein, composition, pharmaceutical composition or medicament as described hereinabove is used to treat coronary diseases (such as, for example, cardiovascular diseases including unstable angina pectoris, myocardial infarction, acute myocardial infarction, coronary artery disease, coronary revascularization, coronary restenosis, ventricular thromboembolism, atherosclerosis, coronary artery disease (e. g., arterial occlusive disorders), plaque formation, cardiac ischemia, including complications related to coronary procedures, such as percutaneous coronary artery angioplasty (balloon angioplasty) procedures). With respect to coronary procedures, such treatment can be achieved via administration of a protein of the invention prior to, during, or subsequent to the procedure. In a preferred embodiment, such administration can be utilized to prevent acute cardiac ischemia following angioplasty.

In another embodiment, the protein, composition, pharmaceutical composition or medicament as described hereinabove is used to treat disorders resulting from any blood vessel insult that can result in platelet aggregation. Such blood vessel insults include, but are not limited to, vessel wall injury, such as vessel injuries that result in a highly thrombogenic surface exposed within an otherwise intact blood vessel e. g., vessel wall injuries that result in release of ADP, thrombin and/or epinephrine, fluid shear stress that occurs at the site of vessel narrowing, ruptures and/or tears at the sites of atherosclerotic plaques, and injury resulting from balloon angioplasty or atherectomy.

Further, in certain embodiments, it is preferred that the protein of the invention does not affect other platelet attributes or functions, such as agonist-induced platelet shape change (e.g., GPIb-vWF-mediated platelet activation), release of internal platelet granule components, activation of signal transduction pathways or induction of calcium mobilization upon platelet activation by agonists that do not interact with GPVI.

In another embodiment, the protein, composition, pharmaceutical composition or medicament as described hereinabove is used to treat disorders associated with aberrant signal transduction in response to ligands of GPVI (including, without limitation, collagen, fibrin, fibronectin, vitronectin and laminins) or to other extracellular matrix proteins.

In another embodiment, the protein, composition, pharmaceutical composition or medicament as described hereinabove is used to treat disorders associated with aberrant levels of GPVI expression and/or activity either in cells that normally express GPVI or in cells that do not express GPVI. For example, the protein of the invention can be used to modulate disorders associated with aberrant expression of GPVI in cancerous (e. g., tumor) cells that do not normally express GPVI. Such disorders can include, for example, ones associated with tumor cell migration and progression to metastasis.

In another embodiment, the protein, composition, pharmaceutical composition or medicament as described hereinabove is used to modulate immunoregulatory functions of platelets.

In another embodiment, the protein, composition, pharmaceutical composition or medicament as described hereinabove is used to treat disorders of liver, bone marrow and peripheral blood.

In another embodiment, the protein, composition, pharmaceutical composition or medicament as described hereinabove is used to treat disorders in which platelets contribute by modulating inflammatory responses including, without limitation, sustained or prolonged inflammation associated with infection, arthritis, fibrosis or disorders in which platelets modulate cell functions including, without limitation, cancer cells proliferation and/or dissemination.

Further examples of diseases, disorders or conditions related to GPVI include, but are not limited to, cardiovascular diseases and/or cardiovascular events, such as, for example, arterial thrombosis including atherothrombosis, ischemic events, acute coronary artery syndrome, myocardial infarction (heart attack), acute cerebrovascular ischemia (stroke), percutaneous coronary intervention, stenting thrombosis, ischemic, restenosis, ischemia, (acute and chronic), diseases of the aorta and its branches (such as aortic aneurysm, thrombosis), peripheral artery disease, venous thrombosis, acute phlebitis and pulmonary embolism, cancer-associated thrombosis (Trousseau syndrome), inflammatory thrombosis and thrombosis associated to infection.

In one embodiment, the pharmaceutical composition or medicament of the invention is for treating or for use in treating arterial or venous thrombosis, restenosis, acute coronary syndrome or cerebrovascular accidents due to atherosclerosis, preferably thrombosis.

Another object of the invention is a method of treating a disease, disorder or condition related to GPVI, wherein said method comprises administering to a subject in need thereof a protein, a composition, a pharmaceutical composition or a medicament of the present invention.

Preferably, a therapeutically effective amount of the protein of the invention is administered to the subject in need thereof.

It will be understood that the total daily usage of the protein of the invention, composition, pharmaceutical composition or medicament of the present invention will be decided by the attending physician within the scope of sound medical judgment. The specific therapeutically effective dose level for any particular patient will depend upon a variety of factors including the disease being treated and the severity of the disease; activity of the specific protein employed; the specific composition employed, the age, body weight, general health, sex and diet of the subject; the time of administration, route of administration, and rate of excretion of the specific protein employed; the duration of the treatment; drugs used in combination or coincidental with the specific protein employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the protein may be varied over a wide range from about 0.01 to 500 mg per adult per day. Preferably, the compositions contain about 1.0, 2.5, 5.0, 10.0, 15.0, 25.0, 50.0, 100, 150, 200, 250, 300, 350, 400, 450 or 500 mg of the active ingredient for the symptomatic adjustment of the dosage to the patient to be treated. A medication typically contains from about 0.01 mg to about 1000 mg of the active ingredient, preferably from 1 mg to about 500 mg of the active ingredient.

In one embodiment, the subject is affected by, preferably is diagnosed with a disease, disorder or condition related to GPVI, preferably a cardiovascular disease and/or event.

In another embodiment, the subject is at risk of developing a disease, disorder or condition related to GPVI, preferably a cardiovascular disease and/or event. Examples of risk include, but are not limited to, family history (such as, for example, genetic predisposition), ethnicity, age, tobacco exposure, high blood pressure (hypertension), high cholesterol, obesity, physical inactivity, diabetes (in particular type 2 diabetes), unhealthy diets, and harmful use of alcohol.

For use in administration to a subject, the composition will be formulated for administration to the subject. The compositions of the present invention may be administered parenterally, by inhalation spray, rectally, nasally, or via an implanted reservoir. The term administration used herein includes subcutaneous, intravenous, intramuscular, intra-articular, intra-synovial, intrasternal, intrathecal, intrahepatic, intralesional and intracranial injection or infusion techniques.

Examples of forms adapted for injection include, but are not limited to, solutions, such as, for example, sterile aqueous solutions, gels, dispersions, emulsions, suspensions, solid forms suitable for using to prepare solutions or suspensions upon the addition of a liquid prior to use, such as, for example, powder, liposomal forms and the like.

Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Schedules and dosages for administration of the protein in the pharmaceutical compositions of the present invention can be determined in accordance with known methods for these products, for example using the manufacturers' instructions. For example, a protein present in a pharmaceutical composition of this invention can be supplied at a concentration ranging from about 1 to about 100 mg/mL, such as, for example, at a concentration of 1 mg/mL, 5 mg/mL, 10 mg/mL, 50 mg/mL or 100 mg/mL. In one embodiment, the protein is supplied at a concentration of about 10 mg/mL in either 100 mg (10 mL) or 500 mg (50 mL) single-use vials. In one embodiment, the pharmaceutical composition of the invention may comprise a protein of the invention in PBS pH 7.2-7.7. It will be appreciated that these schedules are exemplary and that an optimal schedule and regimen can be adapted taking into account the affinity and tolerability of the particular antibody in the pharmaceutical composition that must be determined in clinical trials.

In an embodiment, the protein of the invention may be used in vitro or in vivo to identify samples, tissues, organs or cells that express GPVI.

Examples of assays in which the protein of the invention may be used, include, but are not limited to, ELISA, sandwich ELISA, RIA, FACS, tissue immunohistochemistry, Western-blot, and immunoprecipitation.

In an embodiment of the invention, the sample is a biological sample. Examples of biological samples include, but are not limited to, bodily fluids, preferably blood, more preferably blood serum, plasma, synovial fluid, bronchoalveolar lavage fluid, sputum, lymph, ascitic fluids, urine, amniotic fluid, peritoneal fluid, cerebrospinal fluid, pleural fluid, pericardial fluid, and alveolar macrophages, tissue lysates, biopsies and extracts prepared from diseased tissues.

In an embodiment of the invention, the term "sample" is intended to mean a sample taken from an individual prior to any analysis.

In another embodiment, the protein of the invention may be labeled for diagnostic or detection purposes. By labeled herein is meant that a compound has at least one element, isotope or chemical compound attached to enable the detection of the compound. Examples of labels include, but are not limited to, isotopic labels such as radioactive or heavy isotopes; magnetic, electric or thermal labels and colored or luminescent dyes. Examples of luminescent dyes include, but are not limited to, lanthanide complexes, quantum dots, fluorescein, rhodamine, tetramethylrhodamine, eosin, erythrosin, coumarin, methyl-coumarins, pyrene, malachite green, stilbene, *Lucifer* yellow, cascade blue, texas red, alexa dyes, and cy dyes.

Another object of the invention is a kit comprising at least one protein of the invention.

By "kit" is intended any manufacture (e.g., a package or a container) comprising at least one reagent, i.e. for example an antibody, for specifically detecting the expression of GPVI. The kit may be promoted, distributed, or sold as a unit for performing the methods of the present invention. Furthermore, any or all of the kit reagents may be provided within containers that protect them from the external environment, such as in sealed containers. The kits may also contain a package insert describing the kit and methods for its use.

The present invention further relates to a method for inhibiting GPVI receptor function and downstream signalling, thereby treating a GPVI related condition, wherein said method comprises administering a protein of the invention to a subject.

In one embodiment, the method for inhibiting GPVI receptor function and downstream signalling does not impact platelet count, expression of GPVI at the platelet surface nor bleeding time.

In one embodiment, the method for inhibiting GPVI receptor function and downstream signalling is efficient and reversible.

The present invention further relates to a method for inhibiting the binding of GPVI to its ligands (preferably, but not exclusively, collagen), thereby treating a GPVI related condition, wherein said method comprises administering a protein of the invention to a subject.

In one embodiment, the method for inhibiting the binding of GPVI to its ligands does not impact platelet count, expression of GPVI at the platelet surface nor bleeding time.

In one embodiment, the method for inhibiting the binding of GPVI to its ligands is efficient and reversible.

The present invention further relates to a method for inhibiting and/or preventing platelet adhesion to collagen, thereby treating a GPVI related condition, wherein said method comprises administering a protein of the invention to a subject.

The present invention further relates to a method for inhibiting and/or preventing collagen-induced platelet aggregation, thereby treating a GPVI related condition, wherein said method comprises administering a protein of the invention to a subject.

The present invention further relates to a method for inhibiting and/or preventing platelet activation, in particular platelet aggregation, in response to collagen, thereby treating a GPVI related condition, wherein said method comprises administering a protein of the invention to a subject.

The present invention further relates to a method for inhibiting and/or preventing thrombin production in response to collagen and/or to tissue factor, thereby treating a GPVI related condition, wherein said method comprises administering a protein of the invention to a subject.

The present invention further relates to a method for inhibiting the binding of GPVI to fibrin, thereby treating a GPVI related condition, wherein said method comprises administering a protein of the invention to a subject.

The present invention further relates to a method for inhibiting and/or preventing platelet recruitment by fibrin via GPVI, thereby treating a GPVI related condition, wherein said method comprises administering a protein of the invention to a subject.

The present invention further relates to a method for inhibiting and/or preventing GPVI-dependent thrombin production in response to fibrin, thereby treating a GPVI related condition, wherein said method comprises administering a protein of the invention to a subject.

In one embodiment, administering a protein of the invention to a subject does not induce depletion of GPVI in vivo.

In one embodiment, administering a protein of the invention to a subject does not induce a decrease in platelet count. Thus, in one embodiment, administering a protein of the invention to a subject does not induce thrombocytopenia.

In one embodiment, administering a protein of the invention to a subject does not induce an increase in bleeding time.

In one embodiment, the method of the invention comprises administering a therapeutically effective amount of the protein of the invention to the subject.

BRIEF DESCRIPTION OF THE DRAWINGS

FIGS. 13A-3B are a combination of graphs showing the mean±SD intensity (FIG. 13A) and velocity (FIG. 13B) of collagen-induced platelet aggregation measured at different time after the beginning of a one-hour infusion of two doses of ACT017 (2 and 8 mg/kg) to cynomolgus monkeys (n=8).

EXAMPLES

The present invention is further illustrated by the following examples.

Example 1: Production of ACT017 and ACT006

Antibodies ACT017 and ACT006 (Fab fragments) were produced in CHO-S cells (Invitrogen) by transient transfection, using standard conditions according to the manufacturer instructions.

In brief, immediately before transfection, CHO-S cells were splitted and seeded in 10 mL of serum-free growth medium at a density of 0.5-1.0×10$^6$ cells/mL. Cells were then transfected with a vector comprising a sequence encoding a light chain and a heavy chain of an antibody of the invention. Culture supernatants were recovered 4 to 5 days after transfection, when cell viability was lower than 80%.

For ACT017, cells were transfected using a vector comprising SEQ ID NO: 19 and SEQ ID NO: 18, wherein SEQ ID NO: 19 comprises sequences encoding the constant and variable regions of the light chain of ACT017 fused to a signal peptide sequence, and cloning sites, and wherein SEQ ID NO: 18 comprises sequences encoding the constant and variable regions of the heavy chain of ACT017 fused to a signal peptide sequence, and cloning sites.

For ACT006, cells were transfected using a vector comprising SEQ ID NO: 20 and SEQ ID NO: 18, wherein SEQ ID NO: 20 comprises sequences encoding the constant and variable regions of the light chain of ACT006 fused to a signal peptide sequence, and cloning sites, and wherein SEQ ID NO: 18 comprises sequences encoding the constant and variable regions of the heavy chain of ACT006 fused to a signal peptide sequence, and cloning sites.

For purification, the conditioned media of cells transiently transfected with the cDNA of the humanized Fab was applied on a Protein L agarose column (PIERCE protein L Agarose cat n° 20510017) according the manufacturer instructions. The Fab was eluted using Glycine 0.1 M pH 2.5 and fractions collected on Tris 1 M pH 11 to neutralize the pH. After dialysis against PBS, the concentration of the Fab was determined by measuring absorbance at 280 nm and 320 nm for light scattering correction and using an absorbance value for 0.1% solutions ($A_{280\ nm}^{0.1\%}$) of 1.5 as determined from the sequence. The protein concentration was confirmed by a BCA assay. The purity of the Fab was assessed by SDS-PAGE and Coomassie Blue staining.

Figure 1:
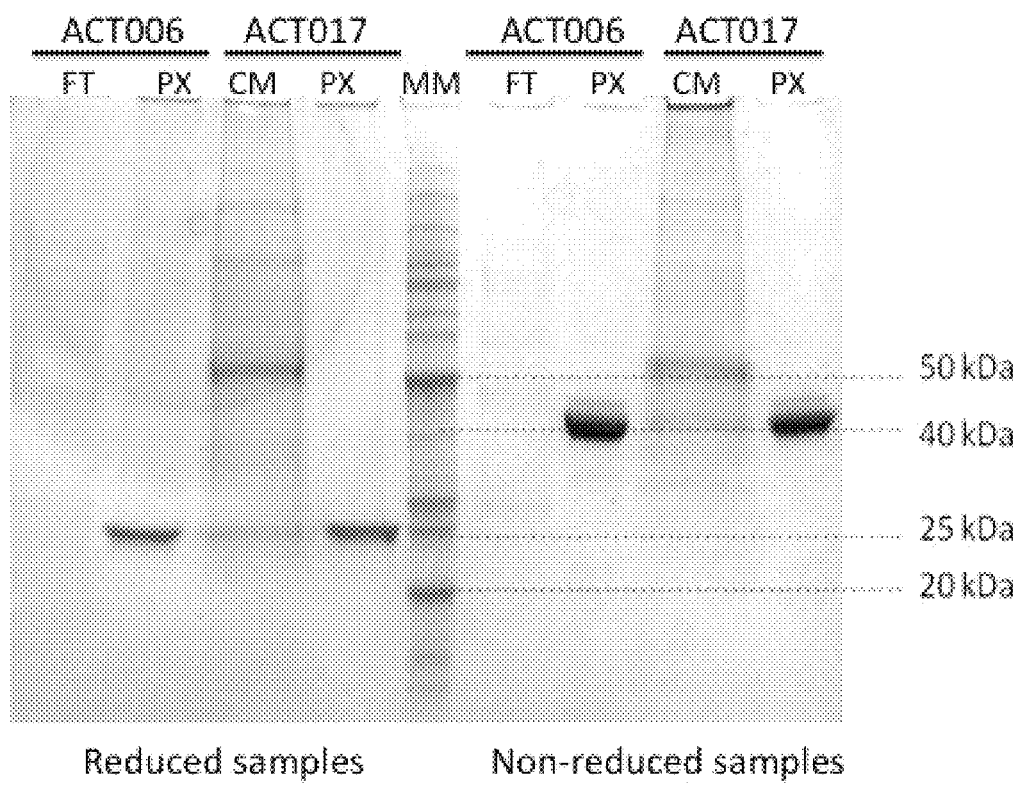
FIG. 1 is a photograph of a gel stained with Coomassie Blue, showing the protein of the invention. MM: molecular weight marker, FT: flow through fraction, PX: protein purified (eluted from the Protein-L agarose column). CM cell culture conditioned media

As shown in FIG. 1, in non-reducing conditions, the purified humanized Fab migrated as a major band of 42 kDa in agreement with its amino-acid sequence. After disulfide bridge reduction, a doublet at 23-24 kDa was observed corresponding to the heavy and light chains.

Example 2: Binding to GPVI-Fc

Soluble GPVI-Fc was produced as follows: the open-reading frame of the predicted extracellular domain of GPVI was PCR-amplified from the Kozak sequence before the first methionine to asparagine 269, immediately prior to the predicted transmembrane sequence. The PCR fragment was ligated into a pCDM8 host vector containing the genomic sequence of the human IgG1 Fc domain, such that the extracellular part of the hGPVI cDNA was fused at its C-terminus via a 3 alanine linker to the hFc sequence. The sequenced DNA construct was transfected into HEK 293T cells. GPVI-Fc was purified from the conditioned media of the cells by affinity chromatography on Protein A agarose according to manufacturer recommendations.

Microtitration plates were coated with GPVI-Fc in PBS (2 μg/mL, 100 μL per well) overnight at 4° C. Nonspecific binding sites were saturated with 100 μL of 1% BSA in PBS for 120 min. The plates were then incubated with increasing concentrations of the antibody preparations (100 μL in PBS containing 0.1% BSA and 0.1% Tween 20) for 120 min. After 4 washing rounds plates were incubated with an alkaline phosphatase-coupled mouse antibody against human Fab (100 μL, in PBS containing 0.1% BSA and 0.1% Tween 20) for 120 min. Finally, 100 μL of the substrate solution (paranitrophenylphosphate) were added to each well for 5 min, and the colorimetric reaction stopped by 25 μL NaOH 3 M before reading the absorbance at 405 nm.

Alternatively, GPVI bound antibodies were detected using peroxidase-coupled protein L and O-Phenylenediamine Dihydrochloride (OPD) as substrate, reading being then performed at 485 nm.

Figure 2:
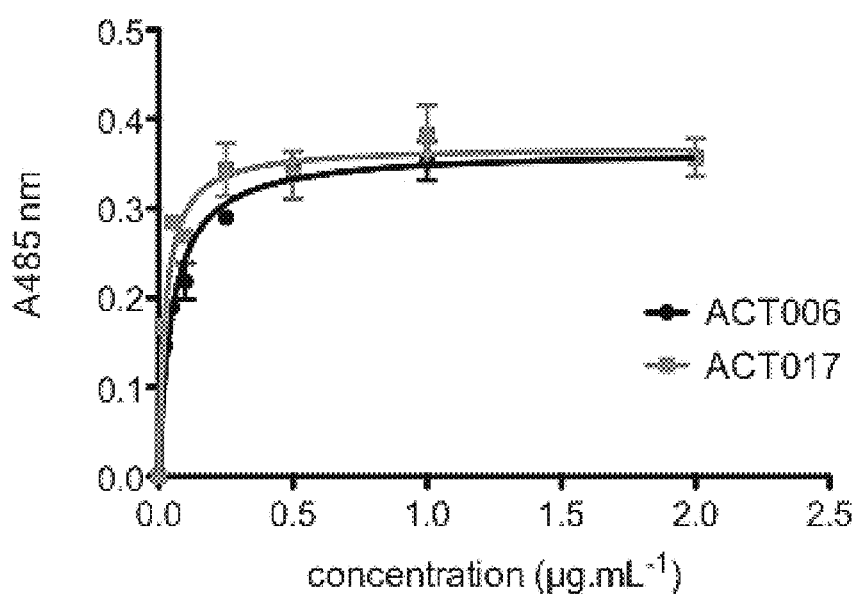
FIG. 2 is a graph showing the isotherm binding curves of two humanized Fab of the invention. Purified GPVI-Fc was coated onto microtitration plates and the purified proteins added at increasing concentrations. After washing, bound proteins were revealed using an alkaline phosphatase coupled-specific antibody to human Fab fragment and hydrolysis of the alkaline phosphatase substrate was measured at 485 nm.

FIG. 2 shows isotherm binding curves of two humanized Fab of the invention on immobilized GPVI-Fc. Analysis of the curves allowed calculating a half-saturation constant of 1 nM for ACT006 and 0.5 nM for ACT017.

Example 3: Surface Plasmon Resonance (BIAcore)

Binding of ACT017, ACT006 and Fab 9012 to soluble human GPVI were analyzed with surface plasmon resonance using a BIAcore 2000 system (Uppsala, Sweden).

Soluble GPVI-Fc (produced as described in Example 2) was immobilized in acetate buffer 10 mM pH 6 at a dose ranging from 960 to 1071 RU (corresponding about 6.4 to 7.15 fmol/mm$^2$) onto a Carboxy-Methyl Dextran CMS sensor chip using the amine coupling method (Wizard procedure). The protein is then passed over the immobilized GPVI-Fc in PBS pH 7.4 (10 mM phosphate, 138 mM NaCl, 2.7 mM KCl, pH 7.42 at 25.4° C.) at a flow rate of 20 μL/min at 25° C. Kinetic constants ($K_A$, $K_D$, $k_{on}$, $k_{off}$) and affinity are determined using BIAevaluation version 3.0 software, by fitting data to binding model. PBS pH 7.4 is the running buffer.

Results are shown in the Table 1 below:

TABLE 1

|  | ACT017 | ACT006 | mFab 9012 |
| --- | --- | --- | --- |
| $k_{on}$ (M$^{-1}$·sec$^{-1}$) | 5.97·10$^4$ | 6.65·10$^4$ | 4.96·10$^4$ |
| $k_{off}$ (sec$^{-1}$) | 2.32·10$^{-4}$ | 4.76·10$^{-4}$ | 8.58·10$^{-4}$ |
| $K_A$ (M$^{-1}$) | 2.57·10$^7$ | 1.4·10$^7$ | 5.8·10$^7$ |
| $K_D$ (nM) | 4.1 (±0.28) | 7.3 (±0.24) | 17.03 (±0.73) |

Antibodies of the invention (ACT017 and ACT006) thus present an enhanced affinity for soluble GPVI as compared to monoclonal Fab 9012 described in the prior art and studied in the same experimental condition.

Example 4: Biologic Data

Materials and Methods

Human platelets: Blood was collected from healthy volunteers who had not taken medication since 10 days by venipuncture onto citrate de sodium 3.2% (Vacutainer Beckton Dickinson, Le Pont-de-Clais, France). All blood donors were volunteers who gave their free and informed written consent to this research study, which conforms to the ethical standards of the Declaration of Helsinki.

Flow cytometry: The humanized Fab ACT017 was coupled to Alexa488 (Molecular Probes) according to the manufacturer recommendation. Separation was performed using an antibody conjugate purification kit (Molecular Probes) and concentration determined at 280 and 494 nm. The A488-coupled humanized Fab at different concentrations was incubated with human platelets in whole blood or platelet rich plasma for 20 min at room temperature in the dark. After dilution in PBS, the cells were analyzed by a fluorescence-activated cell sorter (FACS LSR II BD) flow cytometer.

Platelet aggregation: Human platelet rich plasma (PRP) was obtained after centrifugation (120×g; 15 min; 20° C.) and immediately used. Platelet aggregation was measured using the APACT® aggregometer and initiated by the addition of 1 μg·mL$^{-1}$ type I collagen (Horm collagen, Nycomed, DE) to the PRP containing various concentration of the humanized Fab and continuously recorded. The velocity and intensity of the aggregation were measured.

GPVI-humanized mice: The gp6 knock-in mutant mouse line was established as previously reported by introducing the sequence of the human gp6 gene into exon 1 at ATG of mouse gp6 gene (Mangin P et al., A Humanized Glycoprotein VI (GPVI) Mouse Model to Assess the Antithrombotic Efficacies of Anti-GPVI Agents. J Pharmacol Exp Ther. 2012; 341(1):156-63. doi: 10.1124/jpet.111.189050. Epub 2012 Jan. 11). The mice were viable and fertile and did not present any hematological defects. Approximately 3700 copies of human GPVI were detected at the platelet surface.

Platelet count: Whole blood was collected into EDTA (6 mM) after severing the mouse tail. The platelet count was determined in a scil Vet abc automatic cell counter (Scil Animal Care Company, Holtzheim, France) set to murine parameters.

Ex vivo platelet aggregation: Blood collected onto trisodium citrate before injection and 30 minutes post injection of increasing doses of ACT017 or an equivalent volume of vehicle and PRP obtained by centrifugation. Platelet count was adjusted at 300 $10^9 \cdot L^{-1}$ and platelet aggregation triggered by 1 $\mu g \cdot mL^{-1}$ type I collagen was continuously recorded in four-channel CARAT TX4 aggregometer.

GPVI expression: Blood samples were collected onto EDTA before injection and 30 minutes post injection of increasing doses of ACT017 or an equivalent volume of vehicle and were incubated with the FITC-coupled anti-GPVI monoclonal antibody 3J24 (10 $\mu g \cdot mL^{-1}$) that recognizes human GPVI at an epitope different from the epitope of ACT017, and fluorescence was measured on a Beckman Coulter Gallios Flow cytometer.

Tail bleeding time and blood lost: The extremity of the tail of anesthetized mice was cut transversally with a scalpel (3 mm) and immediately immersed in tube containing 13 mL of 0.9% isotonic saline at 37° C. The bleeding was observed and measured during 30 min, and when necessary bleeding was stopped manually at the 10-minute time point to prevent death. The volume of lost blood was measured based on the hemoglobin content.

Cynomolgus monkeys: 8 cynomolgus monkeys free of any previous treatment were used in the study. Platelet aggregation measurements were performed mostly as described for human platelets and using a collagen concentration of 2.5 $mg \cdot mL^{-1}$. Platelet count was measured in EDTA anticoagulated blood. The bleeding time was measured on vigil monkeys at the surface of the forearm, according to standard clinical procedure and using 0.5 cm Surgicutt™ bleeding time device. GPVI expression was measured mostly as described above using a commercial FITC coupled anti-human GPVI monoclonal antibody (clone 1G5, Biocytex) that cross react with cynomolgus GPVI.

Results

Figure 3:
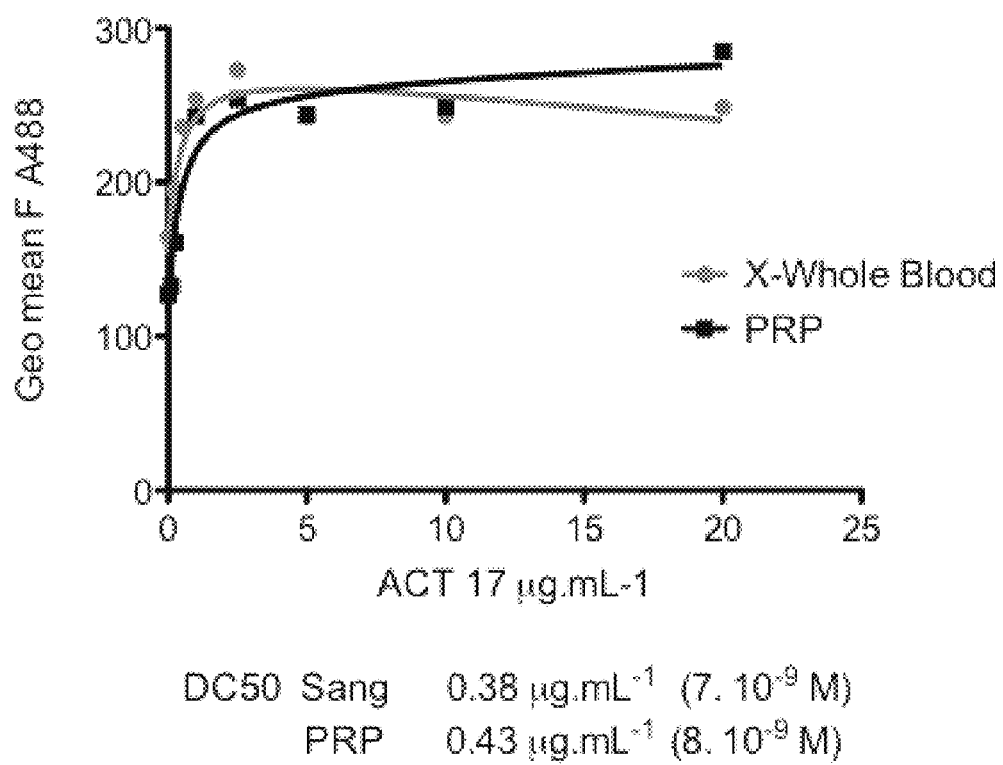
FIG. 3 is a curve obtained by flow cytometry with Alexa488-coupled ACT017. ACT017 was coupled to A488 according to the manufacturer's instructions. A488-ACT0017 was added at increasing concentrations to human whole anticoagulated blood or platelet rich plasma from a healthy volunteer. After 20 min at room temperature, samples were diluted and immediately analyzed by flow cytometry. The mean fluorescence of platelets is represented as function of A488-coupled ACT017 concentration. Data from one representative experiment out of 3.

In vitro binding of ACT017 to human platelets—A typical curve of Alexa488-coupled ACT017 binding to human platelets as determined by flow cytometry is shown on FIG. 3. Saturation of platelets is obtained in whole blood and PRP for an antibody concentration of 1 to 2 μg/mL (20 to 40 nM).

Figure 4:
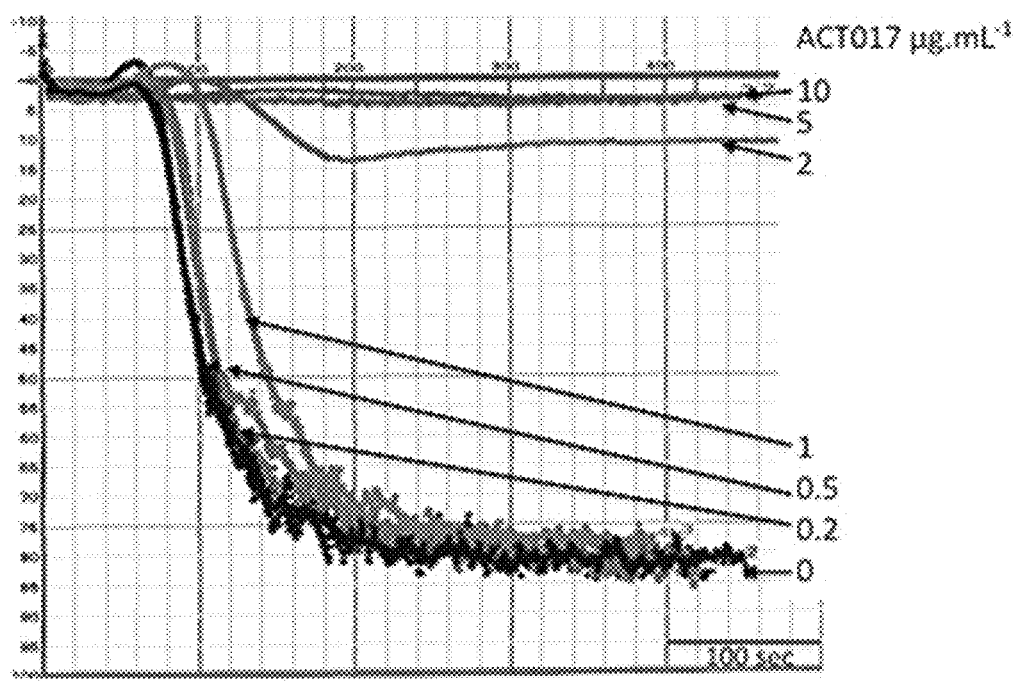
FIG. 4 is a curve showing aggregation of platelets as measured in human platelet-rich plasma (PRP). PRP was pre-incubated with increasing concentrations of purified ACT017 for 10 min at 37° C. without stirring before platelet aggregation was triggered by collagen (1 μg·mL$^{-1}$). Incubation was prolonged at 37° C. with stirring and continuous registration of changes in light transmission. Data from one representative experiment out of 3.

Inhibition, in vitro, of collagen-induced aggregation of human platelets—Typical aggregation curves obtained after preincubation of human PRP with increasing concentrations of ACT017 are shown on FIG. 4. In these conditions ACT017 fully inhibited collagen-induced platelet aggregation for concentration≥5 μg/mL.

Figure 5:
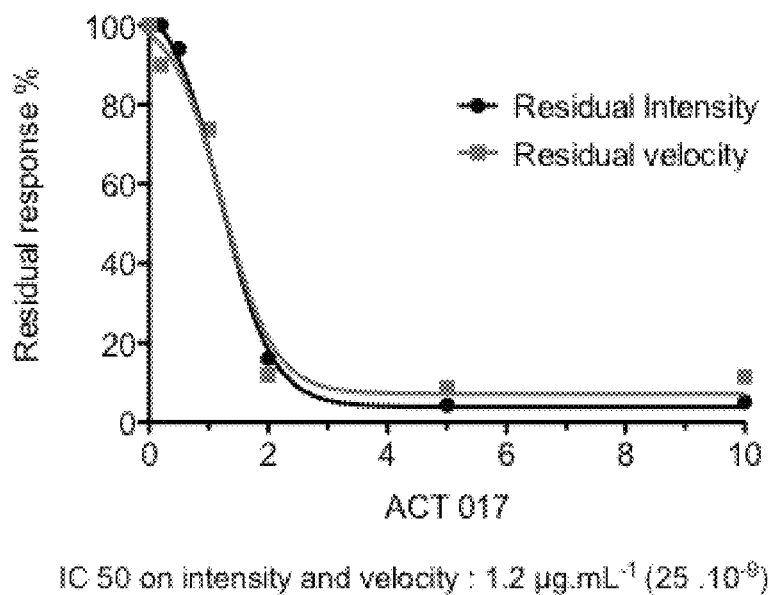
FIG. 5 is a graph showing the capacity of ACT017 to inhibit collagen-induced platelet aggregation quantified on the velocity and intensity of the response. The intensity and velocity of platelet aggregation were measured at each concentration of ACT017. The residual responses were calculated as the ratio of the response in the presence of ACT017 to the response in the absence of ACT017×100 and are plotted as a function of ACT017 concentration using the non-linear regression competition curve (log (inhibitor) vs response) (three parameters) from Graph Pad Prism (5.0) software. Curves are from one representative experiment out of 3.

The capacity of ACT017 to inhibit collagen-induced platelet aggregation was quantified on the velocity and intensity of the response as shown on FIG. 5. On three different donors, the mean IC50 was of 3.2±2.5 and 2±0.7 $\mu g \cdot mL^{-1}$ for the intensity and velocity respectively, while a total inhibition was observed for a concentration of 6.7±2.9 $\mu g \cdot mL^{-1}$ in both cases that is in good agreement with the results of binding to platelets.

These results thus demonstrate that the proteins of the invention are potent inhibitors of collagen-induced platelet aggregation.

Willing to analyze ex vivo the effect of ACT017 on collagen induced platelet aggregation, platelet count and GPVI expression, GPVI-humanized mice received an intravenous injection of ACT017 (1, 2 or 4 mg/kg) or of vehicle. 30 minutes after injection, blood was collected for analysis of collagen induced platelet aggregation, platelet count and GPVI expression.

Figure 6:
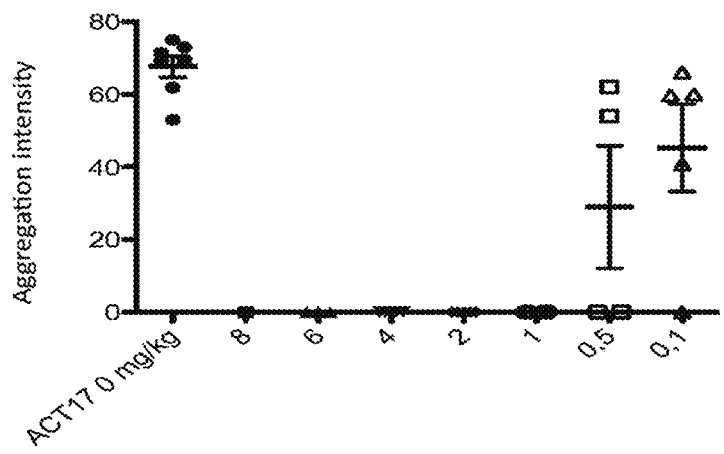
FIG. 6 is a combination of graphs showing collagen induced platelet aggregation. The maximal extent of platelet aggregation triggered by the addition of collagen (1 μg/mL) to the platelet rich plasma (PRP) of mice having received a vehicle or increasing doses of ACT017 is reported.

As shown in FIG. 6, a complete inhibition of collagen-induced platelet aggregation is observed when mice received ACT017 at a dose≥0.5 mg/kg.

Figure 7:
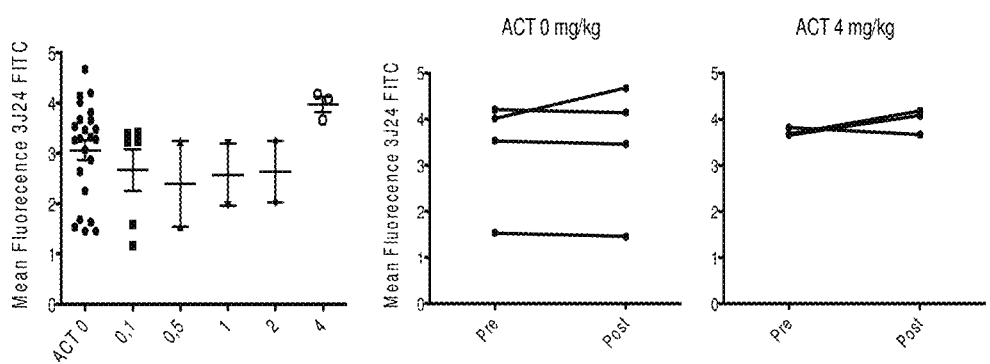
FIG. 7 is a combination of graphs showing the expression of GPVI on platelets. Blood obtained before injection and 30 min after injection of vehicle or of increasing doses of ACT017 was incubated with a FITC-coupled anti-GPVI monoclonal antibody 3J24. Left panel: mean fluorescence of platelets of mice treated by vehicle (ACT17 0 mg/kg) or ACT017 at different doses. Middle and right panels: Evolution of GPVI expression between the pre-injection time and 30 min post injection is reported for individual animals treated with the vehicle or with ACT017 (4 mg/kg).

Regarding the expression of GPVI, there was no statistical difference in the mean fluorescence of platelets in samples recovered pre and post treatment as well as between the samples from mice treated by vehicle (ACT017 0 mg/kg) or ACT017 at different doses (FIG. 7, left panel). Middle and right panels of FIG. 7 show the evolution of GPVI expression between the preinjection time and 30 min post injection in individual animals treated with the vehicle or ACT017 4 mg/kg.

These results demonstrate that ACT017 does not induce GPVI depletion in vivo.

Figure 8:
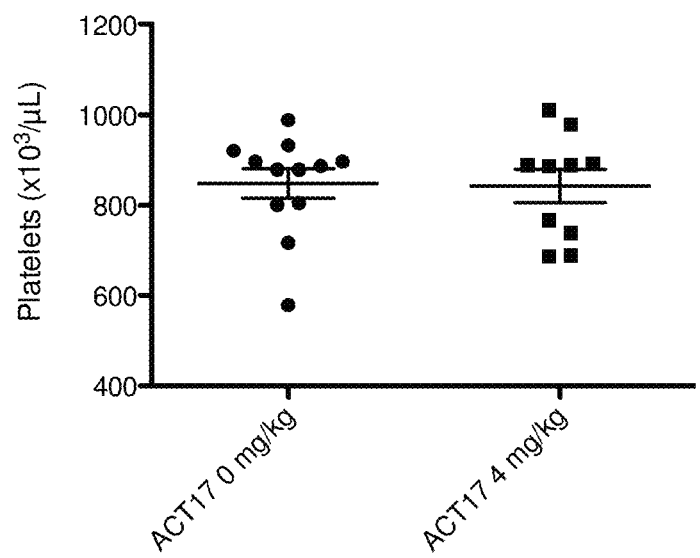
FIG. 8 is a graph showing the number of platelets in blood of mice after administration of ACT017 (4 mg/kg) or of the vehicle (ACT17 0 mg/kg).

Moreover, the platelet counts of mice having received vehicle (ACT017 0 mg/kg) or ACT017 (4 mg/kg) were measured. As shown in FIG. 8, no statistical difference between the two groups was evidenced (mean±SD: 847.7±110.5 vs 842±115.5).

Figures 9A, 9B:
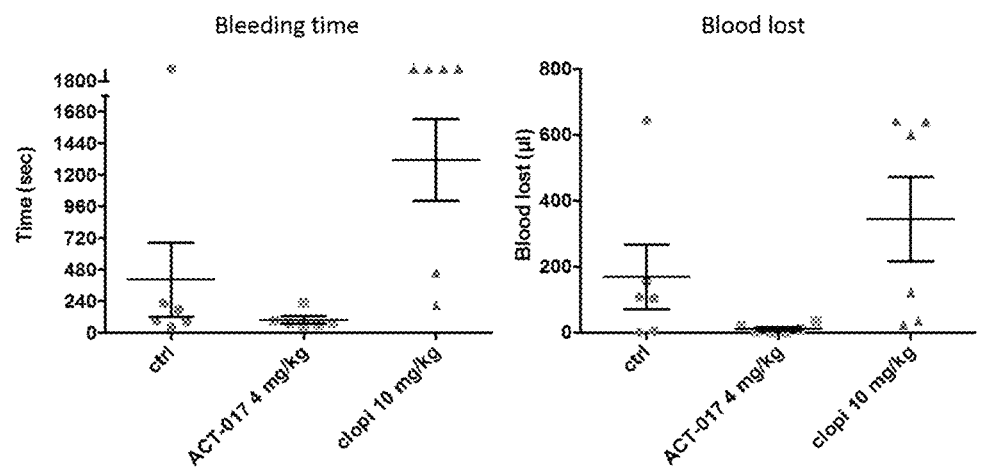
FIGS. 9A-9B are a combination of graphs showing the bleeding time (FIG. 9A) and the blood loss (FIG. 9B) of mice 30 min after administration of vehicle (Ctrl), ACT017 (4 mg/kg) or clopidogrel, an antagonist of the P2Y12 ADP receptor on platelets (10 mg/kg).

The bleeding time and blood loss measured by transection of the tail of mice 30 min after the administration of ACT017 (4 mg/kg) were unmodified as compared to values obtained in control mice (vehicle injection) (FIGS. 9A-9B). For comparison, the bleeding time of clopidogrel treated mice (10 mg/kg the day before and two hours before experiment) was significantly increased as well as the blood loss.

This result demonstrates that ACT017 does not induce a decrease in platelet count, i.e., thrombocytopenia in vivo.

Figure 10A:
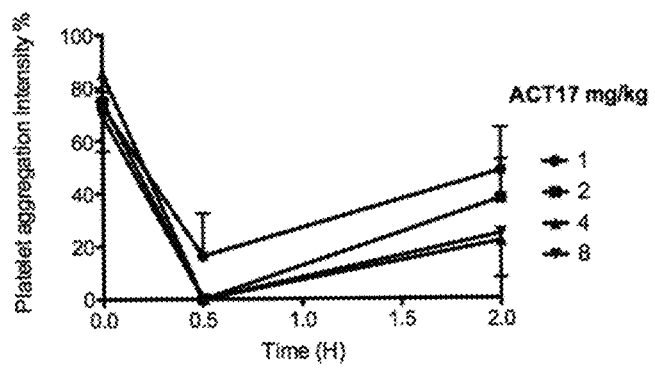
FIGS. 10A-10B are a combination of graphs showing the mean±SEM intensity (FIG. 10A) and velocity (FIG. 10B) of collagen-induced platelet aggregation measured 30 minutes and 2 hours after the end of a 15 minutes' infusion of increasing doses of ACT017 (1, 2, 4, 8 mg/kg) to cynomolgus monkeys (n=4).
Figure 10B:
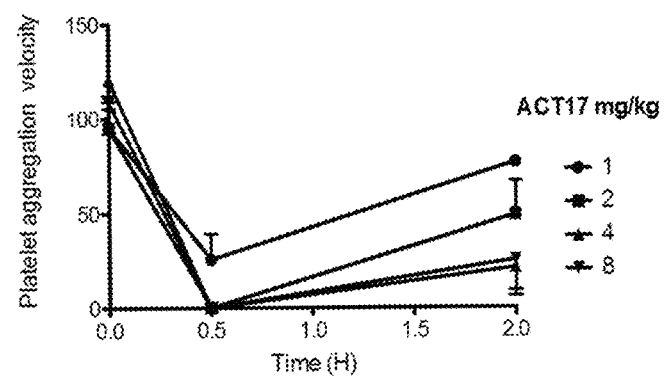
Figure 11:
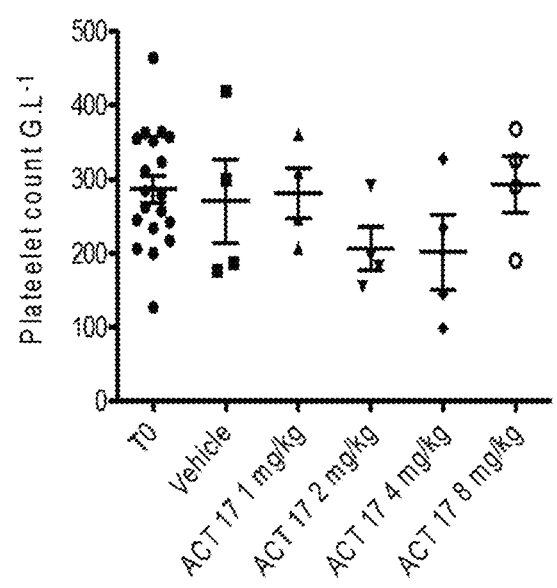
FIG. 11 is showing the blood platelet count of cynomolgus measured before any treatment (TO) or 24 hours after the infusion of vehicle or ACT017 at increasing doses (1, 2, 4, 8 mg/kg).
Figure 12:
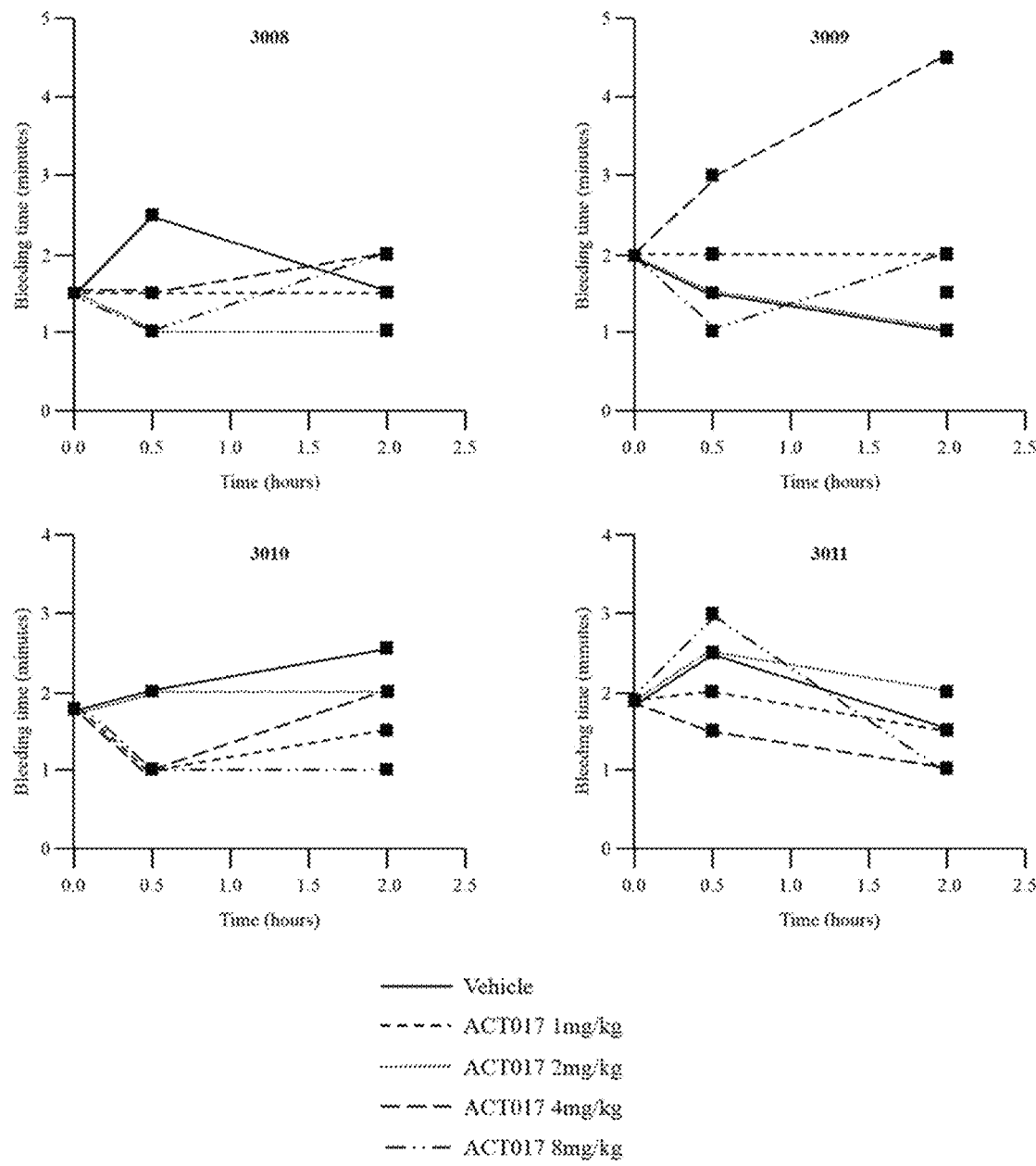
FIG. 12 is a combination of graphs showing the bleeding time measured in 4 subjects, before treatment (Time=0) and 30 min and 2 hours after the infusion of ACT017 (1, 2, 4, 8 mg/kg) or vehicle to cynomolgus monkeys.
Figure 13A:
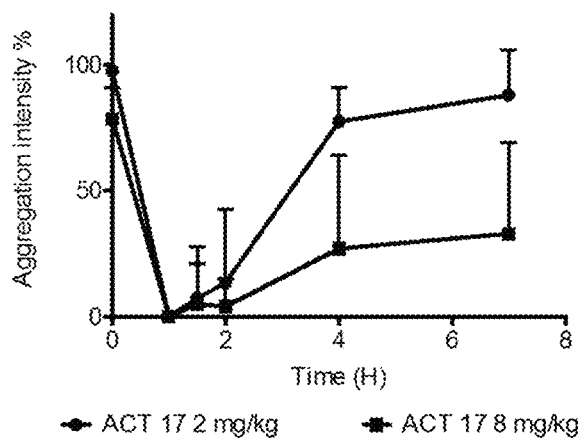
Figure 13B:
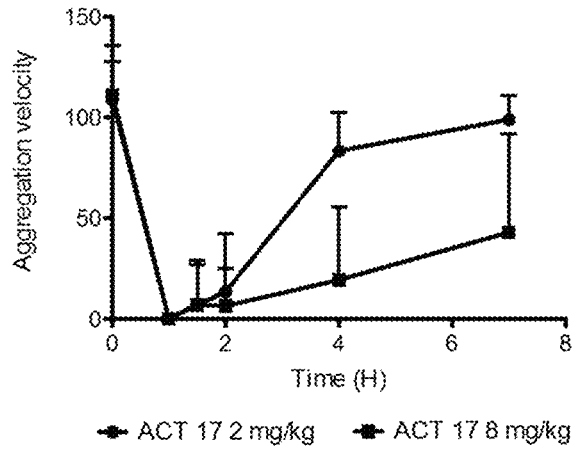
Figure 14:
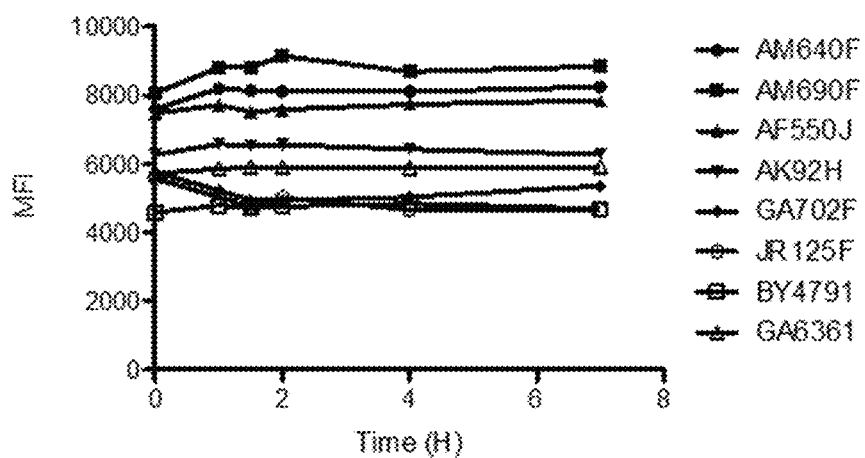
FIG. 14 is a graph showing the level of GPVI expression measured by flow cytometry on the platelets of cynomolgus monkeys (n=8) at different times after the beginning of a one-hour infusion of ACT017 at 2 mg/kg (MFI: Mean Fluorescence Intensity).

The effect of ACT017 administration was further characterized in non-human primates. Eight cynomolgus monkeys were enrolled in the study. First, increasing doses of ACT017 (1, 2, 4, 8 mg/kg) were intravenously administered over 15 minutes. At time 30 minutes and 2 hours after administration, blood was collected. Platelet aggregation was reversibly inhibited in a dose dependent manner (FIGS. 10A-10B). Increasing the dose from 1 to 2 and from 2 to 4 mg/kg increased the effect whereas 8 mg/kg had no additional effect as compared to 4 mg/kg. The platelet count measured 24 hours after the injection was not modified as compared to the values obtained before injection (FIG. 11). No significant increase in the bleeding time was observed after treatment with vehicle or 2, 4 or 8 mg/kg ACT017 (FIG. 12). Next, after a washing out period, the cynomolgus received ACT017 (2 or 8 mg/kg) administered as a one-hour perfusion. Platelet aggregation and GPVI expression were measured at different time after the beginning of the treatment: (1, 1.5, 2, 4 and 7 hours) (FIGS. 13 and 14). Collagen-induced platelet aggregation was reversibly inhibited and the duration of the effect was prolonged in cynomolgus treated with 8 mg/kg compared to 2 mg/kg (FIGS. 13A-13B). GPVI expression on platelets remained stable at the different time after the beginning of the treatment as compared to the pretreatment values (FIG. 14).

Together, these results confirm in non-human primates that administration of ACT017 efficiently and reversibly inhibits GPVI function without impact on the platelet count, on expression of GPVI at the platelet surface nor on bleeding time.

Example 5: Epitope Mapping

Materials and Methods

To reconstruct epitopes of the target molecule, i.e., human GPVI, a library of peptides was synthetized. An amino functionalized polypropylene support was obtained by grafting with a proprietary hydrophilic polymer formulation, followed by reaction with t-butyloxycarbonyl-hexamethylenediamine (BocHMDA) using dicyclohexylcarbodiimide (DCC) with N-hydroxybenzotriazole (HOBt) and subsequent cleavage of the Boc-groups using trifluoroacetic acid (TFA). Standard Fmoc-peptide synthesis was used to synthesize peptides on the amino-functionalized solid support by custom modified JANUS liquid handling stations (Perkin Elmer).

Synthesis of structural mimics was done using Pepscan's proprietary Chemically Linked Peptides on Scaffolds (CLIPS) technology. CLIPS technology allows to structure peptides into single loops, double-loops, triple loops, sheet-like folds, helix-like folds and combinations thereof. CLIPS templates are coupled to cysteine residues. The side-chains of multiple cysteines in the peptides are coupled to one or two CLIPS templates. For example, a 0.5 mM solution of the P2 CLIPS (2,6-bis(bromomethyl)pyridine) is dissolved in ammonium bicarbonate (20 mM, pH 7.8)/acetonitrile (1:3 (v/v)). This solution is added onto the peptide arrays. The CLIPS template bind to side-chains of two cysteines as present in the solid-phase bound peptides of the peptide-arrays (455 wells plate with 3 µL wells). The peptide arrays are gently shaken in the solution for 30 to 60 minutes while completely covered in solution. Finally, the peptide arrays are washed extensively with excess of $H_2O$ and sonicated in disrupt-buffer containing 1% SDS/0.1% beta-mercaptoethanol in PBS (pH 7.2) at 70° C. for 30 minutes, followed by sonication in $H_2O$ for another 45 minutes. The T3 CLIPS carrying peptides were made in a similar way but with three cysteines.

The binding of ACT017 to each of the synthesized peptides was tested in a PEPSCAN-based ELISA. The peptide arrays were incubated with primary antibody solution (overnight at 4° C.). After washing, the peptide arrays were incubated with a 1/1000 dilution of an appropriate antibody peroxidase conjugate (SBA; goat anti-human HRP conjugate, Southern Biotech, 2010-05) for one hour at 25° C. After washing, the peroxidase substrate 2,2'-azino-di-3-ethylbenzthiazoline sulfonate (ABTS) and 20 µl/mL of 3 percent $H_2O_2$ were added. After one hour, the color development was measured. The color development was quantified with a charge coupled device (CCD)-camera and an image processing system.

The values obtained from the CCD-camera range from 0 to 3000 mAU, similar to a standard 96-well plate ELISA-reader. The results are quantified and stored into the Peplab database.

To verify the quality of the synthesized peptides, a separate set of positive and negative control peptides was synthesized in parallel. These were screened with antibody 57.9 (Posthumus et al., J. Virology, 1990, 64:3304-3309).

Intensity profiles for each set of peptides (linear, helical, looped, discontinuous) were analyzed and systematic binding was evaluated.

Results

After several rounds of condition optimization, it was shown that ACT017 systematically recognizes a discontinuous epitope composed of peptide stretches GPAVSSGGD-VTLQCQ and TVTAAHSGTYRCYSF, where GPAVSSGGDVTLQCQ is the dominant part of the recognition site, since CLIPS constrained peptides containing this sequence can also be bound by ACT017; however, there is no detectable binding with linear peptides containing this sequence.

Without willing to be bound by any theory, it is hypothesized that peptide stretch TVTAAHSGTYRCYSF probably provides additional structural context for the binding.

The peptide stretch GPAVSSGGDVTLQCQ is significantly modified in the mouse GPVI, with several non-synonymous mutations; in contrast, it is highly conserved in non-human primates. Without willing to be bound by any theory, it is suggested that this explains why ACT017 binds to human GPVI and non-human primates GPVI, but not to murine GPVI.

Without willing to be bound by any theory, it is suggested that the binding of ACT17 to the identified epitope should impair the binding of collagen to the GPVI Ig-like C2-type domain 1 (D1) and/or GPVI dimerization and subsequent high affinity binding to collagen.

---

The invention claimed is:

1. An isolated humanized protein binding to human Glycoprotein VI (hGPVI) wherein said protein is an antibody molecule, or an antibody fragment,
wherein the variable region of the heavy chain comprises the following CDRs:

```
                         (SEQ ID NO: 1)
VH-CDR1: GYTFTSYNMH;

(SEQ ID NO: 2)
VH-CDR2: GIYPGNGDTSYNQKFQG;
and (SEQ ID NO: 3)
VH-CDR3: GTVVGDWYFDV,
``` and
wherein the variable region of the light chain comprises the following CDRs:

```
                         (SEQ ID NO: 4)
VL-CDR1: RSSQSLENSNGNTYLN;

(SEQ ID NO: 5)
VL-CDR2: RVSNRFS;
and (SEQ ID NO: 6)
VL-CDR3: LQLTHVPWT.
```

2. The isolated humanized protein binding to human Glycoprotein VI (hGPVI) according to claim 1, wherein said protein binds to a conformational epitope comprising:
at least one amino acid residue from a sequence sharing at least 60% of identity over amino acid residues 114 to 142 of hGPVI (SEQ ID NO: 13); and
at least one amino acid residue from a sequence sharing at least 60% of identity over amino acid residues 165 to 187 of hGPVI (SEQ ID NO: 13).

3. The isolated humanized protein binding to human Glycoprotein VI (hGPVI) according to claim 1, wherein said protein binds to a conformational epitope comprising:
at least one amino acid residue from amino acid residues 114 to 142 of hGPVI (SEQ ID NO: 13); and
at least one amino acid residue from amino acid residues 165 to 187 of hGPVI (SEQ ID NO: 13).

4. The isolated humanized protein binding to human Glycoprotein VI (hGPVI) according to claim 2, wherein said conformational epitope comprises:
at least one amino acid residue from a sequence sharing at least 60% of identity over amino acid residues 121 to 135 of hGPVI (SEQ ID NO: 13); and
at least one amino acid residue from a sequence sharing at least 60% of identity over amino acid residues 169 to 183 of hGPVI (SEQ ID NO: 13).

5. The isolated humanized protein binding to human Glycoprotein VI (hGPVI) according to claim 2, wherein said conformational epitope comprises:
at least one amino acid residue from amino acid residues 121 to 135 of hGPVI (SEQ ID NO: 13); and
at least one amino acid residue from amino acid residues 169 to 183 of hGPVI (SEQ ID NO: 13).

6. The isolated humanized protein binding to human Glycoprotein VI (hGPVI) according to claim 1, wherein said protein has a $K_D$ for binding to hGPVI less than 15 nM, wherein said $K_D$ is measured by surface plasmon resonance using 960 to 1071 RU of soluble human GPVI and using PBS pH 7.4 as running buffer, and wherein said isolated humanized protein does not induce a GPVI depletion phenotype in vivo.

7. The isolated humanized protein binding to human Glycoprotein VI (hGPVI) according to claim 1, comprising an antibody molecule selected from the group consisting of a whole antibody, a humanized antibody, a single chain antibody, a Fv, and a Fab.

8. The isolated humanized protein binding to human Glycoprotein VI (hGPVI) according to claim 1, comprising a unibody.

9. The isolated humanized protein binding to human Glycoprotein VI (hGPVI) according to claim 1, comprising a monovalent antibody.

10. The isolated humanized protein binding to human Glycoprotein VI (hGPVI) according to claim 1, comprising an antibody wherein the amino acid sequence encoding the heavy chain variable region is at least 60% identical to SEQ ID NO: 7 and the amino acid sequence encoding the light chain variable region is at least 60% identical to SEQ ID NO: 8.

11. The isolated humanized protein binding to human Glycoprotein VI (hGPVI) according to claim 1, comprising an antibody wherein the amino acid sequence encoding the heavy chain variable region is at least 60% identical to SEQ ID NO: 7 and the amino acid sequence encoding the light chain variable region is at least 60% identical to SEQ ID NO: 9.

12. The isolated humanized protein binding to human Glycoprotein VI (hGPVI) according to claim 1, comprising an antibody wherein the amino acid sequence encoding the heavy chain variable region is SEQ ID NO: 7 and the amino acid sequence encoding the light chain variable region is SEQ ID NO: 8.

13. The isolated humanized protein binding to human Glycoprotein VI (hGPVI) according to claim 1, comprising an antibody wherein the amino acid sequence encoding the heavy chain variable region is SEQ ID NO: 7 and the amino acid sequence encoding the light chain variable region is SEQ ID NO: 9.

14. A method for treating a cardiovascular disease, wherein said method comprises administering an isolated humanized protein binding to human Glycoprotein VI (hGPVI), wherein said protein is an antibody molecule, or an antibody fragment,
wherein the variable region of the heavy chain comprises the following CDRs:

```
                         (SEQ ID NO: 1)
VH-CDR1: GYTFTSYNMH;

(SEQ ID NO: 2)
VH-CDR2: GIYPGNGDTSYNQKFQG;
and (SEQ ID NO: 3)
VH-CDR3: GTVVGDWYFDV,
``` and
   wherein the variable region of the light chain comprises the following CDRs:

```
                                    (SEQ ID NO: 4)
VL-CDR1: RSSQSLENSNGNTYLN;

(SEQ ID NO: 5)
VL-CDR2: RVSNRFS;
and (SEQ ID NO: 6)
VL-CDR3: LQLTHVPWT.
```

15. The method according to claim 14, wherein said cardiovascular disease is selected from the group consisting of arterial and venous thrombosis, restenosis and thromboembolic diseases.

16. The method according to claim 14, wherein said cardiovascular disease is selected from coronary artery diseases, cerebral artery diseases, peripheral artery diseases, and venous thrombosis.

17. The method according to claim 14, wherein said cardiovascular disease is selected from acute coronary syndrome, ischemic cerebrovascular accidents, myocardial infarction, stroke, acute phlebitis, and pulmonary embolism.

* * * * *